US011351246B2

(12) United States Patent
Langlade Demoyen et al.

(10) Patent No.: US 11,351,246 B2
(45) Date of Patent: Jun. 7, 2022

(54) RECOMBINANT MEASLES VACCINE EXPRESSING HTERT

(71) Applicants: INVECTYS SAS, Paris (FR); INSTITUT PASTEUR, Paris (FR); CENTRE NATIONAL DE LA RECHERCHE SCIENTIFIQUE, Paris (FR)

(72) Inventors: Pierre Langlade Demoyen, Neuilly-sur-Seine (FR); Frédéric Tangy, Les Lilas (FR); Elodie Pliquet, Gentilly (FR)

(73) Assignees: INVECTYS SAS, Paris (FR); INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 45 days.

(21) Appl. No.: 16/611,786

(22) PCT Filed: May 7, 2018

(86) PCT No.: PCT/EP2018/061733
§ 371 (c)(1),
(2) Date: Nov. 7, 2019

(87) PCT Pub. No.: WO2018/206512
PCT Pub. Date: Nov. 15, 2018

(65) Prior Publication Data
US 2021/0077613 A1 Mar. 18, 2021

(30) Foreign Application Priority Data
May 9, 2017 (EP) .................................... 17305522

(51) Int. Cl.
*A61K 39/165* (2006.01)
*A61K 39/00* (2006.01)

(52) U.S. Cl.
CPC .... *A61K 39/165* (2013.01); *A61K 2039/5256* (2013.01); *A61K 2039/53* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 5,539,084 A | 7/1996 | Geysen et al. | |
| 5,840,839 A | 11/1998 | Wang et al. | |
| 8,003,773 B2 | 8/2011 | Langlade-Demoyen et al. | |
| 8,222,392 B2 | 7/2012 | Cech et al. | |
| 9,005,925 B2 * | 4/2015 | Tangy | C12N 7/00 435/70.3 |
| 9,931,387 B2 | 4/2018 | Langlade Demoyen et al. | |
| 10,138,488 B2 | 11/2018 | Langlade Demoyen et al. | |
| 10,183,065 B2 | 1/2019 | Langlade Demoyen et al. | |
| 10,675,337 B2 | 6/2020 | Langlade Demoyen et al. | |
| 2003/0143228 A1 | 7/2003 | Chen et al. | |
| 2004/0106128 A1 | 6/2004 | Majumdar | |
| 2008/0090778 A1 | 4/2008 | Scarselli et al. | |
| 2009/0162405 A1 | 6/2009 | Qian | |
| 2009/0175892 A1 | 7/2009 | Langlade-Demoyen et al. | |
| 2009/0269739 A1 | 10/2009 | Cech et al. | |
| 2011/0318380 A1 | 12/2011 | Brix et al. | |
| 2016/0046950 A1 | 2/2016 | Langlade Demoyen et al. | |
| 2016/0051650 A1 | 2/2016 | Langlade Demoyen | |
| 2016/0347798 A1 | 12/2016 | Poma et al. | |
| 2019/0000946 A1 | 1/2019 | Langlade Demoyen et al. | |

FOREIGN PATENT DOCUMENTS

| | | |
|---|---|---|
| EP | 1375512 A1 | 1/2004 |
| JP | 2012-039877 A | 3/2012 |
| WO | WO 1998014593 A2 | 4/1998 |
| WO | WO 2011/073796 A2 | 6/2001 |
| WO | WO 2003038047 A2 | 5/2003 |
| WO | WO 2008043760 A2 | 4/2008 |
| WO | 2015063117 A1 | 5/2015 |

OTHER PUBLICATIONS

Shan Lu, Current Opinion in Immunology, 2009, 21:346-351. (Year: 2009).*
Pliquet et al., Cancer Immunology, Immunotherapy, 2019, 68:533-544. (Year: 2019).*
Adoté, O. et al., "Targeting Human Telomerase Reverse Transcriptase with Recombinant Lentivector is Highly Effective to Stimulate Antitumor CD8 T-Cell Immunity In Vivo" Blood (2010) vol. 115, No. 15, pp. 3025-3032.
Calvet, C.Y. et al., "Optimization of a Gene Electrotransfer Procedure for Efficient Intradermal Immunization with an hTERT-based DNA Vaccine in Mice" Molecular Therapy—Methods and Clinical Development (2014) vol. 1, No. 14045, 10 pages total.
Combredet, C. et al., "A Molecularly Clones Schwarz Strain of Measles Virus Vaccine Induces Strong Immune Responses in Macaques and Transgenic Mice" Journal of Virology, The American Society for Microbiology (2003) vol. 77, No. 21, pp. 11546-11554.
Radecke, F. et al., "Rescue of Measles Viruses from Cloned DNA" European Molecular Biology Organization (1995) vol. 14, No. 23, pp. 5773-5784.

(Continued)

Primary Examiner — Stacy B Chen
(74) Attorney, Agent, or Firm — Cooley LLP; Ivor R. Elrifi

(57) ABSTRACT

The invention relates a recombinant measles virus plasmid capable of expressing a human telomerase reverse transcriptase (hTERT) protein fused at N-terminus with a protein enhancing addressing of the hTERT protein to proteasome. The invention further relates to a vaccine comprising said plasmid or particles rescued therefrom, and uses thereof, especially in preventing or treating a tumor in a patient.

Figure 2A:
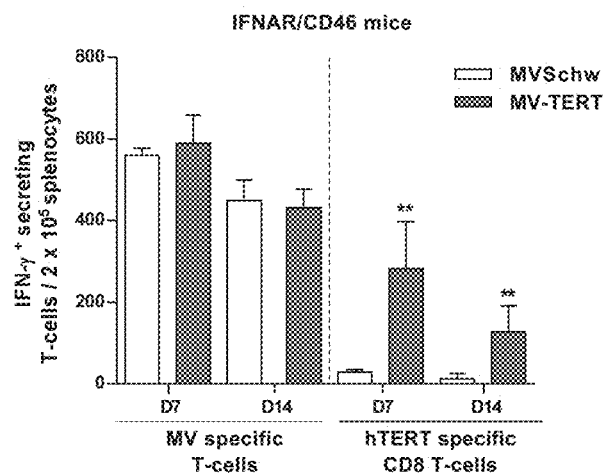

26 Claims, 5 Drawing Sheets
Specification includes a Sequence Listing.

(56) References Cited

OTHER PUBLICATIONS

Communication (International Search Report) issued by the International Searching Authority in International Application No. PCT/EP2018/061733 dated Aug. 2, 2018, 7 pages total.
Communication (Written Opinion) issued by the International Searching Authority in International Application No. PCT/EP2018/061733 dated Aug. 2, 2018, 7 pages total.
Adotevi, O. et al. "Immunogenic HLA-B*0702-Restricted Epitopes Derived from Human Telomerase Reverse Transcriptase that Elicit Antitumor Cytotoxic T-Cell Responses" Clin Cancer Res, 2006, 12(10), 3158-3167.
Andersson, H.A. et al., "Maximizing Antigen Targeting to the Proteasome for Gene-Based Vaccines" Molecular Therapy, 2004, 10(3), 432-446.
Armbruster, B.N. et al., "N-Terminal Domains of the Human Telomerase Catalytic Subunit Required for Enzyme Activity in Vivo" Molecular and Cellular Biology, 2001, 21(22), 7775-7786.
Artandi, S. E. et al., "Telomeres and telomerase in cancer" Carcinogenesis, 2010, 31(1), 9-18.
Bevan, M. J., "Helping the CD8+ T-Cell Response" Nature Reviews Immunology, 2004, 4, 595-602.
Bolonaki, I. et al., "Vaccination of Patients with Advanced Non-Small-Cell Lung Cancer With an Optimized Cryptic Human Telomerase Reverse Transcriptase Peptide" Journal of Clinical Oncology: Official Journal of the American Society of Clinical Oncology, 2007, 25(19), 2727-2734.
Cadile, C.D. et al., "Telomerase activity as a marker for malignancy in feline tissues" American Journal of Veterinary Research, 2001, 62(10), 1578-1581.
Chou, B. et al., "Antiangiogenic Tumor Therapy by DNA Vaccine Inducing Aquaporin-1-Specific CTL Based on Ubiquitin-Proteasome System in Mice" Journal of Immunology, 2012, 189(4), 1618-1626.
Delogu, G. et al., "DNA Vaccine Combinations Expressing Either Tissue Plasminogen Activator Signal Sequence Fusion Proteins or Ubiquitin-Conjugated Antigens Induce Sustained Protective Immunity in a Mouse Model of Pulmonary Tuberculosis" Infection and Immunity, 2002, 70(1), 292-302.
Drosopoulos, W.C. et al., "The active site residue Valine 867 in human telomerase reverse transcriptase influences nucleotide incorporation and fidelity" Nucleic Acids Research, 2007, 35(4), pp. 1155-1168.
Duan, X. et al., "The Ubiquitin-Proteasome System Plays Essential Roles in Presenting an 8-Mer CTL Epitope Expressed in APC to Corresponding CD8+ T Cells" International Immunology, 2006, 18(5), 679-687.
English Translation of Japanese Office Action Issued in JP2016-504709, dated Oct. 10, 2017, 1-5.
English Translation of Japanese Office Action issued in JP2016-504710, dated Oct. 10, 2017, 1-6.
Eslami, N. S. et al., "Simultaneous Immunisation with a Wilms' Tumour 1 Epitope and its Ubiquitin Fusions Results in Enhanced Cell Mediated Immunity and Tumour Rejection in C57BL/6 Mice" Molecular Immunology, 2012, 51(3-4), 325-331.
European Communication Pursuant to Article 94(3) EPC issued in EP14716530.2 and dated Jan. 17, 2017, 1-5.
European Communication Pursuant to Article 94(3) EPC issued in EP14790592.1 and dated May 30, 2017, 1-4.
European Communication Pursuant to Rule 114(2) EPC issued in EP 14790592.1 and dated Jul. 6, 2018, 1-3.
European Search Report and Opinion dated Sep. 24, 2012, which issued during prosecution of European Application No. 12305319.1, 1-7.
GenBank databases, NCBI. Accession No. AAD30037.1, May 11, 1999, [online], searched on May 30, 2018, <URL: https://www.ncbi.nlm.nih.gov/protein/4808973?sat=4&satkey=35386002>, 3 pages total.
Godet, Y. et al. "Analysis of Spontaneous Tumor-Specific CD4 T-cell immunity in Lung Cancer Using Promiscuous HLA-DR Telomerase-Derived Epitopes: Potential Synergistic Effect with Chemotherapy Response" Clinical Cancer Research: An Official Journal of the American Association for Cancer Research, 2012, 18(10), 2943-2953.
Hanahan, D. et al., "Hallmarks of Cancer: The Next Generation" Cell, 2014, 144, 646-674.
Huang, J.J. et al., "Ectopic Expression of a COOH-terminal Fragment of the Human Telomerase Reverse Transcriptase Leads to Telomere Dysfunction and Reduction of Growth and Tumorigenicity in HeLa Cells" Cancer Research, 2002, 62(11), 3226-3232.
Huo, L. et al., "Cancer Immunotherapy Targeting the Telomerase Reverse Transcriptase" Cellular and Molecular Immunology, 2006, 3(1), 1-9.
Impellizeri, J. A. et al., "Electro-gene-transfer as a new tool for cancer immunotherapy in animals" Veterinary and Comparative Oncology, Short Communication, 2012, 12(4), 1-9, DOI: 10.1111/vco.12006.
International Preliminary Report on Patentability dated Sep. 29, 2015 during prosecution of International Patent Application No. PCT/EP2014/056381, 1-8.
International Preliminary Report on Patentability issued in International Application No. PCT/EP2013/054592 dated Sep. 16, 2014, 1-5.
International Preliminary Report on Patentability Issued in International Application No. PCT/EP2014/073164 Issued May 3, 2016, 1-6.
International Search Report and Written Opinion of the International Searching Authority dated Apr. 12, 2013, which issued during prosecution of International Application No. PCT/EP2013/054592, 1-13.
International Search Report and Written Opinion of the International Searching Authority dated Feb. 4, 2015, which issued during prosecution of international Application No. POT/EP2014/073164, 1-10.
International Search Report and Written Opinion of the International Searching Authority dated Jul. 2, 2014, which issued during prosecution of International Application No. PCT/EP2014/056381.
International Search Report and Written Opinion of the International Searching Authority issued in POT/EP2014/056380, dated Jul. 23, 2014, 1-14.
Kiecker, F. et al., "Analysis of Antigen-Specific T-Cell Responses With Synthetic Peptides—What Kind of Peptide for Which Purpose?" Human Immunology, 2004, 65, 523-536.
Klebanoff, C.A. et al., "Therapeutic cancer vaccines: are we there yet?" Immunology Reviews, 2011, 239, 27-44.
Kyte, J.A. et al., "Telomerase Peptide Vaccination Combined with Temozolomide: A Clinical Trial in Stage IV Melanoma Patients" Clinical Cancer Research, 2011, 7(13), 4568-4580.
Martinez, Paula et al., "Telomeric and extra-telomeric roles for telomerase and the telomere-binding proteins" Reviews Cancer, 2011, 11, 161-176.
Muller S., "Ubiquitin," Manual of Biological Markers of Disease, 1994, B2(3), 1-11.
NCBI Reference Sequence AAC51724.1, Telomerase catalytic subunit [Homo sapiens], dated Aug. 28, 1997, 2 pages.
NCBI Reference Sequence NM_198253.2, Homo sapiens telomerase reverse transcriptase (TERT), transcript variant 1, mRNA, dated Oct. 27, 2012, 8 pages.
NCBI Reference Sequence XP_019669508.1, Predicted: Low Quality Protein: telomerase reverse transcriptase, partial [Felis catus], dated Dec. 29, 2016, 2 pages.
NG, SSM et al., "A novel glioblastoma cancer gene therapy using AAV-mediated long-term expression of human TERT-terminal polypeptide" Cancer Gene Therapy, 2007, 14, 561-572.
Osen, W. et al., "Screening of Human Tumor Antigens for CD4+ T Cell Epitopes by Combination of HLA-Transgenic Mice, Recombinant Adenovirus and Antigen Peptide Libraries" PLoS ONE, 2010, 5(11), p. e14137.
Peruzzi, D. et al., "A Vaccine Targeting Telomerase Enhances Survival of Dogs Affected by B-cell Lymphoma" Therapy, 2010, 18(8), 1559-1567.
Peruzzi, D., et al., "Telomerase and HER-2/neu as targets of genetic cancer vaccines in dogs" Vaccine, 2010, 28(5), 1201-1208.

(56) References Cited

OTHER PUBLICATIONS

Reay, P. et al., "Use of Global Amino Replacements to Define the Requirements for MHC Binding and T Cell of Moth Cytochrome, c (93-103)" Journal of Immunology, 1994, 152, 3946-3957.

Ruden, M. et al., "Novel anticancer therapeutics targeting telomerase" Cancer Treatment Reviews 2013, 39(5), 444-456.

Scardino, A. et al., "HER-2/neu and hTERT Cryptic Epitopes as Novel Targets for Broad Spectrum Tumor Immunotherapy" The Journal of Immunology, 2002, 168, 5900-5906.

Schlapbach, C. et al., "Telomerase-specific GV1001 peptide vaccination fails to induce objective tumor response in patients with cutaneous 1 cell lymphoma" Journal of Dermatological Science, 2011, 62(2), 75-83.

Schroers, R. et at. "Identification of HLA DR7-restricted Epitopes from Human Telomerase Reverse Transcriptase Recognized by CD4+ T-Helper Cells" Cancer Research, American Association for Cancer Research, 2002, 629, 2600-2605.

Schroers, R. et at., "Human Telomerase Reverse Transcriptase-Specific T-Helper Responses Induced by Promiscuous Major Histocompatibility Complex Class II-Restricted Epitopes" Clinical Cancer Research: An Official Journal of the American Association for Cancer Research, 2003, 9(13), 4743-4755.

Velders, M. P. et al., "Defined Flanking Spacers and Enhanced Proteolysis Is Essential for Eradication of Established Tumors by an Epitope String DNA Vaccine" Journal Immunology, 2001, 166, 5366-5373.

Wang, Q. et al., "Improved Cellular Immune Response Elicited by a Ubiquitin-Fused DNA Vaccine Against *Mycobacterium tuberculosis*" DNA and Cell Biology, 2012, 31(4), 489-495.

Yamano, T. et al., "Immunity Against Breast Cancer by TERT DNA Vaccine Primed with Chemokine CCL21" Cancer Gene Therapy, 2007, 14, 451-459.

Yang, Y. et al., "Nucleolar Localization of hTERT Protein is Associated with Telomerase Function" Experimental Research, 2002, 277(2), 201-209.

Zhang, M. et al., "A Novel DNA Vaccine Based on Ubiquitin-Proteasome Pathway Targeting 'Self'-Antigens Expressed in Melanoma/Melanocyte" Gene Therapy, 2005, 12(13), 1049-1057.

\* cited by examiner

FIG. 1A

FIG. 1B

SEQUENCE LISTING

```
<160> NUMBER OF SEQ ID NOS: 32

<210> SEQ ID NO 1
<211> LENGTH: 4018
<212> TYPE: DNA
<213> ORGANISM: Homo sapiens
<220> FEATURE:
<221> NAME/KEY: CDS
<222> LOCATION: (59)..(3457)

<400> SEQUENCE: 1
caggcagcgc tgcgtcctgc tgcgcacgtg ggaagccctg gccccggcca ccccgcg         58 atg ccg cgc gct ccc cgc tgc cga gcc gtg cgc tcc ctg ctg cgc agc      106
Met Pro Arg Ala Pro Arg Cys Arg Ala Val Arg Ser Leu Leu Arg Ser
1               5                   10                  15 cac tac cgc gag gtg ctc ccg ctg gcc acg ttc gtg cgg cgc ctg ggg      154
His Tyr Arg Glu Val Leu Pro Leu Ala Thr Phe Val Arg Arg Leu Gly
            20                  25                  30 ccc cag ggc tgg cgg ctg gtg cag cgc ggg gac ccg gcg gct ttc cgc      202
Pro Gln Gly Trp Arg Leu Val Gln Arg Gly Asp Pro Ala Ala Phe Arg
        35                  40                  45 gcg ctg gtg gcc cag tgc ctg gtg tgc gtg ccc tgg gac gca cgg ccg      250
Ala Leu Val Ala Gln Cys Leu Val Cys Val Pro Trp Asp Ala Arg Pro
    50                  55                  60 ccc ccc gcc gcc ccc tcc ttc cgc cag gtg tcc tgc ctg aag gag ctg      298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg      346
Val Ala Arg Val Leu Gln Arg Leu Cys Glu Arg Gly Ala Lys Asn Val
                85                  90                  95 ctg gcc ttc ggc ttc gcg ctg ctg gac ggg gcc cgc ggg ggc ccc ccc      394
Leu Ala Phe Gly Phe Ala Leu Leu Asp Gly Ala Arg Gly Gly Pro Pro
            100                 105                 110 gag gcc ttc acc acc agc gtg cgc agc tac ctg ccc aac acg gtg acc      442
Glu Ala Phe Thr Thr Ser Val Arg Ser Tyr Leu Pro Asn Thr Val Thr
        115                 120                 125 gac gca ctg cgg ggg agc ggg gcg tgg ggg ctg ctg ctg cgc cgc gtg      490
Asp Ala Leu Arg Gly Ser Gly Ala Trp Gly Leu Leu Leu Arg Arg Val
    130                 135                 140 ggc gac gac gtg ctg gtt cac ctg ctg gca cgc tgc gcg ctc ttt gtg      538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac      586
Leu Val Ala Pro Ser Cys Ala Tyr Gln Val Cys Gly Pro Pro Leu Tyr
                165                 170                 175
```

-continued

| | | |
|---|---|---|
| cag ctc ggc gct gcc act cag gcc cgg ccc ccg cca cac gct agt gga<br>Gln Leu Gly Ala Ala Thr Gln Ala Arg Pro Pro Pro His Ala Ser Gly<br>180 185 190 | | 634 |
| ccc cga agg cgt ctg gga tgc gaa cgg gcc tgg aac cat agc gtc agg<br>Pro Arg Arg Arg Leu Gly Cys Glu Arg Ala Trp Asn His Ser Val Arg<br>195 200 205 | | 682 |
| gag gcc ggg gtc ccc ctg ggc ctg cca gcc ccg ggt gcg agg agg cgc<br>Glu Ala Gly Val Pro Leu Gly Leu Pro Ala Pro Gly Ala Arg Arg Arg<br>210 215 220 | | 730 |
| ggg ggc agt gcc agc cga agt ctg ccg ttg ccc aag agg ccc agg cgt<br>Gly Gly Ser Ala Ser Arg Ser Leu Pro Leu Pro Lys Arg Pro Arg Arg<br>225 230 235 240 | | 778 |
| ggc gct gcc cct gag ccg gag cgg acg ccc gtt ggg cag ggg tcc tgg<br>Gly Ala Ala Pro Glu Pro Glu Arg Thr Pro Val Gly Gln Gly Ser Trp<br>245 250 255 | | 826 |
| gcc cac ccg ggc agg acg cgt gga ccg agt gac cgt ggt ttc tgt gtg<br>Ala His Pro Gly Arg Thr Arg Gly Pro Ser Asp Arg Gly Phe Cys Val<br>260 265 270 | | 874 |
| gtg tca cct gcc aga ccc gcc gaa gaa gcc acc tct ttg gag ggt gcg<br>Val Ser Pro Ala Arg Pro Ala Glu Glu Ala Thr Ser Leu Glu Gly Ala<br>275 280 285 | | 922 |
| ctc tct ggc acg cgc cac tcc cac cca tcc gtg ggc cgc cag cac cac<br>Leu Ser Gly Thr Arg His Ser His Pro Ser Val Gly Arg Gln His His<br>290 295 300 | | 970 |
| gcg ggc ccc cca tcc aca tcg cgg cca cca cgt ccc tgg gac acg cct<br>Ala Gly Pro Pro Ser Thr Ser Arg Pro Pro Arg Pro Trp Asp Thr Pro<br>305 310 315 320 | | 1018 |
| tgt ccc ccg gtg tac gcc gag acc aag cac ttc ctc tac tcc tca ggc<br>Cys Pro Pro Val Tyr Ala Glu Thr Lys His Phe Leu Tyr Ser Ser Gly<br>325 330 335 | | 1066 |
| gac aag gag cag ctg cgg ccc tcc ttc cta ctc agc tct ctg agg ccc<br>Asp Lys Glu Gln Leu Arg Pro Ser Phe Leu Leu Ser Ser Leu Arg Pro<br>340 345 350 | | 1114 |
| agc ctg act ggc gct cgg agg ctc gtg gag acc atc ttt ctg ggt tcc<br>Ser Leu Thr Gly Ala Arg Arg Leu Val Glu Thr Ile Phe Leu Gly Ser<br>355 360 365 | | 1162 |
| agg ccc tgg atg cca ggg act ccc cgc agg ttg ccc cgc ctg ccc cag<br>Arg Pro Trp Met Pro Gly Thr Pro Arg Arg Leu Pro Arg Leu Pro Gln<br>370 375 380 | | 1210 |
| cgc tac tgg caa atg cgg ccc ctg ttt ctg gag ctg ctt ggg aac cac<br>Arg Tyr Trp Gln Met Arg Pro Leu Phe Leu Glu Leu Leu Gly Asn His<br>385 390 395 400 | | 1258 |
| gcg cag tgc ccc tac ggg gtg ctc ctc aag acg cac tgc ccg ctg cga<br>Ala Gln Cys Pro Tyr Gly Val Leu Leu Lys Thr His Cys Pro Leu Arg<br>405 410 415 | | 1306 |
| gct gcg gtc acc cca gca gcc ggt gtc tgt gcc cgg gag aag ccc cag<br>Ala Ala Val Thr Pro Ala Ala Gly Val Cys Ala Arg Glu Lys Pro Gln<br>420 425 430 | | 1354 |
| ggc tct gtg gcg gcc ccc gag gag gag gac aca gac ccc cgt cgc ctg<br>Gly Ser Val Ala Ala Pro Glu Glu Glu Asp Thr Asp Pro Arg Arg Leu<br>435 440 445 | | 1402 |
| gtg cag ctg ctc cgc cag cac agc agc ccc tgg cag gtg tac ggc ttc<br>Val Gln Leu Leu Arg Gln His Ser Ser Pro Trp Gln Val Tyr Gly Phe<br>450 455 460 | | 1450 |
| gtg cgg gcc tgc ctg cgc cgg ctg gtg ccc cca ggc ctc tgg ggc tcc<br>Val Arg Ala Cys Leu Arg Arg Leu Val Pro Pro Gly Leu Trp Gly Ser<br>465 470 475 480 | | 1498 |
| agg cac aac gaa cgc cgc ttc ctc agg aac acc aag aag ttc atc tcc<br>Arg His Asn Glu Arg Arg Phe Leu Arg Asn Thr Lys Lys Phe Ile Ser<br>485 490 495 | | 1546 |

```
ctg ggg aag cat gcc aag ctc tcg ctg cag gag ctg acg tgg aag atg      1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt      1642
Ser Val Arg Asp Cys Ala Trp Leu Arg Arg Ser Pro Gly Val Gly Cys
        515                 520                 525 gtt ccg gcc gca gag cac cgt ctg cgt gag gag atc ctg gcc aag ttc      1690
Val Pro Ala Ala Glu His Arg Leu Arg Glu Glu Ile Leu Ala Lys Phe
    530                 535                 540 ctg cac tgg ctg atg agt gtg tac gtc gtc gag ctc ctc agg tct ttc      1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac      1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac      1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag      1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc      1930
His Arg Glu Ala Arg Pro Ala Leu Leu Thr Ser Arg Leu Arg Phe Ile
    610                 615                 620 ccc aag cct gac ggg ctg cgg ccg att gtg aac atg gac tac gtc gtg      1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg      2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc      2074
Arg Val Lys Ala Leu Phe Ser Val Leu Asn Tyr Glu Arg Ala Arg Arg
            660                 665                 670 ccc ggc ctc ctg ggc gcc tct gtg ctg ggc ctg gac gat atc cac agg      2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct      2170
Ala Trp Arg Thr Phe Val Leu Arg Val Arg Ala Gln Asp Pro Pro Pro
    690                 695                 700 gag ctg tac ttt gtc aag gtg gat gtg acg ggc gcg tac gac acc atc      2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag      2266
Pro Gln Asp Arg Leu Thr Glu Val Ile Ala Ser Ile Ile Lys Pro Gln
                725                 730                 735 aac acg tac tgc gtg cgt cgg tat gcc gtg gtc cag aag gcc gcc cat      2314
Asn Thr Tyr Cys Val Arg Arg Tyr Ala Val Val Gln Lys Ala Ala His
            740                 745                 750 ggg cac gtc cgc aag gcc ttc aag agc cac gtc tct acc ttg aca gac      2362
Gly His Val Arg Lys Ala Phe Lys Ser His Val Ser Thr Leu Thr Asp
        755                 760                 765 ctc cag ccg tac atg cga cag ttc gtg gct cac ctg cag gag acc agc      2410
Leu Gln Pro Tyr Met Arg Gln Phe Val Ala His Leu Gln Glu Thr Ser
    770                 775                 780 ccg ctg agg gat gcc gtc gtc atc gag cag agc tcc tcc ctg aat gag      2458
Pro Leu Arg Asp Ala Val Val Ile Glu Gln Ser Ser Ser Leu Asn Glu
785                 790                 795                 800 gcc agc agt ggc ctc ttc gac gtc ttc cta cgc ttc atg tgc cac cac      2506
Ala Ser Ser Gly Leu Phe Asp Val Phe Leu Arg Phe Met Cys His His
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     |     | 805 |     |     |     | 810 |     |     |     | 815 |     |     |      |
| gcc | gtg | cgc | atc | agg | ggc | aag | tcc | tac | gtc | cag | tgc | cag | ggg | atc | ccg | 2554 |
| Ala | Val | Arg | Ile | Arg | Gly | Lys | Ser | Tyr | Val | Gln | Cys | Gln | Gly | Ile | Pro |      |
|     |     |     | 820 |     |     |     |     | 825 |     |     |     | 830 |     |     |      |
| cag | ggc | tcc | atc | ctc | tcc | acg | ctg | ctc | tgc | agc | ctg | tgc | tac | ggc | gac | 2602 |
| Gln | Gly | Ser | Ile | Leu | Ser | Thr | Leu | Leu | Cys | Ser | Leu | Cys | Tyr | Gly | Asp |      |
|     |     | 835 |     |     |     |     | 840 |     |     |     |     | 845 |     |     |      |
| atg | gag | aac | aag | ctg | ttt | gcg | ggg | att | cgg | cgg | gac | ggg | ctg | ctc | ctg | 2650 |
| Met | Glu | Asn | Lys | Leu | Phe | Ala | Gly | Ile | Arg | Arg | Asp | Gly | Leu | Leu | Leu |      |
|     | 850 |     |     |     |     | 855 |     |     |     |     | 860 |     |     |     |      |
| cgt | ttg | gtg | gat | gat | ttc | ttg | ttg | gta | aca | cct | cac | ctc | acc | cac | gcg | 2698 |
| Arg | Leu | Val | Asp | Asp | Phe | Leu | Leu | Val | Thr | Pro | His | Leu | Thr | His | Ala |      |
| 865 |     |     |     |     | 870 |     |     |     |     | 875 |     |     |     |     | 880  |
| aaa | acc | ttc | ctc | agg | acc | ctg | gtc | cga | ggt | gtc | cct | gag | tat | ggc | tgc | 2746 |
| Lys | Thr | Phe | Leu | Arg | Thr | Leu | Val | Arg | Gly | Val | Pro | Glu | Tyr | Gly | Cys |      |
|     |     |     |     | 885 |     |     |     |     | 890 |     |     |     |     | 895 |      |
| gtg | gtg | aac | ttg | cgg | aag | aca | gtg | gtg | aac | ttc | cct | gta | gaa | gac | gag | 2794 |
| Val | Val | Asn | Leu | Arg | Lys | Thr | Val | Val | Asn | Phe | Pro | Val | Glu | Asp | Glu |      |
|     |     |     | 900 |     |     |     |     | 905 |     |     |     |     | 910 |     |      |
| gcc | ctg | ggt | ggc | acg | gct | ttt | gtt | cag | atg | ccg | gcc | cac | ggc | cta | ttc | 2842 |
| Ala | Leu | Gly | Gly | Thr | Ala | Phe | Val | Gln | Met | Pro | Ala | His | Gly | Leu | Phe |      |
|     |     | 915 |     |     |     |     | 920 |     |     |     |     | 925 |     |     |      |
| ccc | tgg | tgc | ggc | ctg | ctg | ctg | gat | acc | cgg | acc | ctg | gag | gtg | cag | agc | 2890 |
| Pro | Trp | Cys | Gly | Leu | Leu | Leu | Asp | Thr | Arg | Thr | Leu | Glu | Val | Gln | Ser |      |
|     | 930 |     |     |     |     | 935 |     |     |     |     | 940 |     |     |     |      |
| gac | tac | tcc | agc | tat | gcc | cgg | acc | tcc | atc | aga | gcc | agt | ctc | acc | ttc | 2938 |
| Asp | Tyr | Ser | Ser | Tyr | Ala | Arg | Thr | Ser | Ile | Arg | Ala | Ser | Leu | Thr | Phe |      |
| 945 |     |     |     |     | 950 |     |     |     |     | 955 |     |     |     |     | 960  |
| aac | cgc | ggc | ttc | aag | gct | ggg | agg | aac | atg | cgt | cgc | aaa | ctc | ttt | ggg | 2986 |
| Asn | Arg | Gly | Phe | Lys | Ala | Gly | Arg | Asn | Met | Arg | Arg | Lys | Leu | Phe | Gly |      |
|     |     |     |     | 965 |     |     |     |     | 970 |     |     |     |     | 975 |      |
| gtc | ttg | cgg | ctg | aag | tgt | cac | agc | ctg | ttt | ctg | gat | ttg | cag | gtg | aac | 3034 |
| Val | Leu | Arg | Leu | Lys | Cys | His | Ser | Leu | Phe | Leu | Asp | Leu | Gln | Val | Asn |      |
|     |     |     | 980 |     |     |     |     | 985 |     |     |     |     | 990 |     |      |
| agc | ctc | cag | acg | gtg | tgc | acc | aac | atc | tac | aag | atc | ctc | ctg | ctg | cag | 3082 |
| Ser | Leu | Gln | Thr | Val | Cys | Thr | Asn | Ile | Tyr | Lys | Ile | Leu | Leu | Leu | Gln |      |
|     |     | 995 |     |     |     |     | 1000|     |     |     |     | 1005|     |     |      |
| gcg | tac | agg | ttt | cac | gca | tgt | gtg | ctg | cag | ctc | cca | ttt | cat | cag |     | 3127 |
| Ala | Tyr | Arg | Phe | His | Ala | Cys | Val | Leu | Gln | Leu | Pro | Phe | His | Gln |     |      |
|     | 1010|     |     |     |     | 1015|     |     |     |     | 1020|     |     |     |      |
| caa | gtt | tgg | aag | aac | ccc | aca | ttt | ttc | ctg | cgc | gtc | atc | tct | gac |     | 3172 |
| Gln | Val | Trp | Lys | Asn | Pro | Thr | Phe | Phe | Leu | Arg | Val | Ile | Ser | Asp |     |      |
|     | 1025|     |     |     |     | 1030|     |     |     |     | 1035|     |     |     |      |
| acg | gcc | tcc | ctc | tgc | tac | tcc | atc | ctg | aaa | gcc | aag | aac | gca | ggg |     | 3217 |
| Thr | Ala | Ser | Leu | Cys | Tyr | Ser | Ile | Leu | Lys | Ala | Lys | Asn | Ala | Gly |     |      |
|     | 1040|     |     |     |     | 1045|     |     |     |     | 1050|     |     |     |      |
| atg | tcg | ctg | ggg | gcc | aag | ggc | gcc | gcc | ggc | cct | ctg | ccc | tcc | gag |     | 3262 |
| Met | Ser | Leu | Gly | Ala | Lys | Gly | Ala | Ala | Gly | Pro | Leu | Pro | Ser | Glu |     |      |
|     | 1055|     |     |     |     | 1060|     |     |     |     | 1065|     |     |     |      |
| gcc | gtg | cag | tgg | ctg | tgc | cac | caa | gca | ttc | ctg | ctc | aag | ctg | act |     | 3307 |
| Ala | Val | Gln | Trp | Leu | Cys | His | Gln | Ala | Phe | Leu | Leu | Lys | Leu | Thr |     |      |
|     | 1070|     |     |     |     | 1075|     |     |     |     | 1080|     |     |     |      |
| cga | cac | cgt | gtc | acc | tac | gtg | cca | ctc | ctg | ggg | tca | ctc | agg | aca |     | 3352 |
| Arg | His | Arg | Val | Thr | Tyr | Val | Pro | Leu | Leu | Gly | Ser | Leu | Arg | Thr |     |      |
|     | 1085|     |     |     |     | 1090|     |     |     |     | 1095|     |     |     |      |
| gcc | cag | acg | cag | ctg | agt | cgg | aag | ctc | ccg | ggg | acg | acg | ctg | act |     | 3397 |
| Ala | Gln | Thr | Gln | Leu | Ser | Arg | Lys | Leu | Pro | Gly | Thr | Thr | Leu | Thr |     |      |
|     | 1100|     |     |     |     | 1105|     |     |     |     | 1110|     |     |     |      |
| gcc | ctg | gag | gcc | gca | gcc | aac | ccg | gca | ctg | ccc | tca | gac | ttc | aag |     | 3442 |

```
Ala Leu Glu Ala Ala Ala Asn Pro Ala Leu Pro Ser Asp Phe Lys
    1115                1120                1125 acc atc ctg gac tga tggccacccg cccacagcca ggccgagagc agacaccagc      3497
Thr Ile Leu Asp
    1130 agccctgtca cgccgggctc tacgtcccag ggagggaggg gcggcccaca cccaggcccg    3557 caccgctggg agtctgaggc ctgagtgagt gtttggccga ggcctgcatg tccggctgaa    3617 ggctgagtgt ccggctgagg cctgagcgag tgtccagcca agggctgagt gtccagcaca    3677 cctgccgtct tcacttcccc acaggctggc gctcggctcc accccagggc cagcttttcc    3737 tcaccaggag cccggcttcc actccccaca taggaatagt ccatcccag attcgccatt     3797 gttcacccct cgccctgccc tcctttgcct tccaccccca ccatccaggt ggagaccctg    3857 agaaggaccc tgggagctct gggaatttgg agtgaccaaa ggtgtgccct gtacacaggc    3917 gaggaccctg cacctggatg ggggtccctg tgggtcaaat tgggggagg tgctgtggga     3977 gtaaaatact gaatatatga gttttcagt tttgaaaaaa a                         4018

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
```

```
                245                 250                 255
Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670
```

```
Pro Gly Leu Leu Gly Ala Ser Val Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
    835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
    915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
    995                 1000                1005

Ala Tyr Arg Phe His Ala Cys Val Leu Gln Leu Pro Phe His Gln
        1010                1015                1020

Gln Val Trp Lys Asn Pro Thr Phe Phe Leu Arg Val Ile Ser Asp
        1025                1030                1035

Thr Ala Ser Leu Cys Tyr Ser Ile Leu Lys Ala Lys Asn Ala Gly
        1040                1045                1050

Met Ser Leu Gly Ala Lys Gly Ala Ala Gly Pro Leu Pro Ser Glu
        1055                1060                1065

Ala Val Gln Trp Leu Cys His Gln Ala Phe Leu Leu Lys Leu Thr
        1070                1075                1080
```

Arg His Arg Val Thr Tyr Val Pro Leu Leu Gly Ser Leu Arg Thr
1085                1090                1095

Ala Gln Thr Gln Leu Ser Arg Lys Leu Pro Gly Thr Thr Leu Thr
1100                1105                1110

Ala Leu Glu Ala Ala Ala Asn Pro Ala Leu Pro Ser Asp Phe Lys
1115                1120                1125

Thr Ile Leu Asp
1130

```
<210> SEQ ID NO 3
<211> LENGTH: 22649
<212> TYPE: DNA
<213> ORGANISM: Artificial Sequence
<220> FEATURE:
<223> OTHER INFORMATION: pTM-MV-TERT
<220> FEATURE:
<221> NAME/KEY: misc_feature
<222> LOCATION: (1)..(8)
<223> OTHER INFORMATION: NotI restriction site
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammer head ribozyme
<220> FEATURE:
<221> NAME/KEY: misc_feature
<222> LOCATION: (83)..(3445)
<223> OTHER INFORMATION: MV Schwarz antigenome
<220> FEATURE:
<221> NAME/KEY: CDS
<222> LOCATION: (190)..(1767)
<223> OTHER INFORMATION: N protein nucleotidique sequence
<220> FEATURE:
<221> NAME/KEY: CDS
<222> LOCATION: (1889)..(3412)
<223> OTHER INFORMATION: P protein nucleotidique sequence
<220> FEATURE:
<221> NAME/KEY: misc_feature
<222> LOCATION: (2911)..(2922)
<223> OTHER INFORMATION: Factor Xa site
<220> FEATURE:
<221> NAME/KEY: misc_feature
<222> LOCATION: (3477)..(3489)
<223> OTHER INFORMATION: Cis-acting element
<220> FEATURE:
<221> NAME/KEY: CDS
<222> LOCATION: (3535)..(3762)
<223> OTHER INFORMATION: Human ubiquitin
<220> FEATURE:
<221> NAME/KEY: CDS
<222> LOCATION: (3763)..(7008)
<223> OTHER INFORMATION: delta hTERT
<220> FEATURE:
<221> NAME/KEY: CDS
<222> LOCATION: (7009)..(7062)
<223> OTHER INFORMATION: Flu HLA-A*0201
<220> FEATURE:
<221> NAME/KEY: CDS
<222> LOCATION: (7063)..(7107)
<223> OTHER INFORMATION: V5 tag
<220> FEATURE:
<221> NAME/KEY: misc_feature
<222> LOCATION: (7157)..(7169)
<223> OTHER INFORMATION: Cis-acting element
<220> FEATURE:
<221> NAME/KEY: CDS
<222> LOCATION: (7202)..(8209)
<223> OTHER INFORMATION: M protein nucleotidique sequence
<220> FEATURE:
<221> NAME/KEY: CDS
<222> LOCATION: (9213)..(10874)
<223> OTHER INFORMATION: F protein nucleotidique sequence
```

-continued

```
<220> FEATURE:
<221> NAME/KEY: misc_feature
<222> LOCATION: (10041)..(19658)
<223> OTHER INFORMATION: MV Schwarz antigenome
<220> FEATURE:
<221> NAME/KEY: CDS
<222> LOCATION: (11035)..(12888)
<223> OTHER INFORMATION: H protein nucleotidique sequence
<220> FEATURE:
<221> NAME/KEY: CDS
<222> LOCATION: (12998)..(19549)
<223> OTHER INFORMATION: L protein nucleotidique sequence
<220> FEATURE:
<221> NAME/KEY: misc_feature
<222> LOCATION: (13700)..(13711)
<223> OTHER INFORMATION: Factor Xa site
<220> FEATURE:
<221> NAME/KEY: misc_feature
<222> LOCATION: (19659)..(19742)
<223> OTHER INFORMATION: Hepatitis delta virus (HDV) ribozyme
<220> FEATURE:
<221> NAME/KEY: misc_feature
<222> LOCATION: (19813)..(19859)
<223> OTHER INFORMATION: T7 terminator

<400> SEQUENCE: 3
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180 atatccgag atg gcc aca ctt tta agg agc tta gca ttg ttc aaa aga aac     231
          Met Ala Thr Leu Leu Arg Ser Leu Ala Leu Phe Lys Arg Asn
          1               5                   10 aag gac aaa cca ccc att aca tca gga tcc ggt gga gcc atc aga gga       279
Lys Asp Lys Pro Pro Ile Thr Ser Gly Ser Gly Gly Ala Ile Arg Gly
15                  20                  25                  30 atc aaa cac att att ata gta cca atc cct gga gat tcc tca att acc       327
Ile Lys His Ile Ile Ile Val Pro Ile Pro Gly Asp Ser Ser Ile Thr
                35                  40                  45 act cga tcc aga ctt ctg gac cgg ttg gtg agg tta att gga aac ccg       375
Thr Arg Ser Arg Leu Leu Asp Arg Leu Val Arg Leu Ile Gly Asn Pro
            50                  55                  60 gat gtg agc ggg ccc aaa cta aca ggg gca cta ata ggt ata tta tcc       423
Asp Val Ser Gly Pro Lys Leu Thr Gly Ala Leu Ile Gly Ile Leu Ser
        65                  70                  75 tta ttt gtg gag tct cca ggt caa ttg att cag agg atc acc gat gac       471
Leu Phe Val Glu Ser Pro Gly Gln Leu Ile Gln Arg Ile Thr Asp Asp
    80                  85                  90 cct gac gtt agc ata agg ctg tta gag gtt gtc cag agt gac cag tca       519
Pro Asp Val Ser Ile Arg Leu Leu Glu Val Val Gln Ser Asp Gln Ser
95                  100                 105                 110 caa tct ggc ctt acc ttc gca tca aga ggt acc aac atg gag gat gag       567
Gln Ser Gly Leu Thr Phe Ala Ser Arg Gly Thr Asn Met Glu Asp Glu
                115                 120                 125 gcg gac caa tac ttt tca cat gat gat cca att agt agt gat caa tcc       615
Ala Asp Gln Tyr Phe Ser His Asp Asp Pro Ile Ser Ser Asp Gln Ser
            130                 135                 140 agg ttc gga tgg ttc ggg aac aag gaa atc tca gat att gaa gtg caa       663
Arg Phe Gly Trp Phe Gly Asn Lys Glu Ile Ser Asp Ile Glu Val Gln
        145                 150                 155 gac cct gag gga ttc aac atg att ctg ggt acc atc cta gcc caa att       711
Asp Pro Glu Gly Phe Asn Met Ile Leu Gly Thr Ile Leu Ala Gln Ile
    160                 165                 170 tgg gtc ttg ctc gca aag gcg gtt acg gcc cca gac acg gca gct gat       759
Trp Val Leu Leu Ala Lys Ala Val Thr Ala Pro Asp Thr Ala Ala Asp
```

```
                 175                 180                 185                 190
tcg gag cta aga agg tgg ata aag tac acc caa caa aga agg gta gtt        807
Ser Glu Leu Arg Arg Trp Ile Lys Tyr Thr Gln Gln Arg Arg Val Val
                     195                 200                 205 ggt gaa ttt aga ttg gag aga aaa tgg ttg gat gtg gtg agg aac agg        855
Gly Glu Phe Arg Leu Glu Arg Lys Trp Leu Asp Val Val Arg Asn Arg
             210                 215                 220 att gcc gag gac ctc tcc tta cgc cga ttc atg gtc gct cta atc ctg        903
Ile Ala Glu Asp Leu Ser Leu Arg Arg Phe Met Val Ala Leu Ile Leu
         225                 230                 235 gat atc aag aga aca ccc gga aac aaa ccc agg att gct gaa atg ata        951
Asp Ile Lys Arg Thr Pro Gly Asn Lys Pro Arg Ile Ala Glu Met Ile
     240                 245                 250 tgt gac att gat aca tat atc gta gag gca gga tta gcc agt ttt atc        999
Cys Asp Ile Asp Thr Tyr Ile Val Glu Ala Gly Leu Ala Ser Phe Ile
255                 260                 265                 270 ctg act att aag ttt ggg ata gaa act atg tat cct gct ctt gga ctg       1047
Leu Thr Ile Lys Phe Gly Ile Glu Thr Met Tyr Pro Ala Leu Gly Leu
                 275                 280                 285 cat gaa ttt gct ggt gag tta tcc aca ctt gag tcc ttg atg aac ctt       1095
His Glu Phe Ala Gly Glu Leu Ser Thr Leu Glu Ser Leu Met Asn Leu
             290                 295                 300 tac cag caa atg ggg gaa act gca ccc tac atg gta atc ctg gag aac       1143
Tyr Gln Gln Met Gly Glu Thr Ala Pro Tyr Met Val Ile Leu Glu Asn
         305                 310                 315 tca att cag aac aag ttc agt gca gga tca tac cct ctg ctc tgg agc       1191
Ser Ile Gln Asn Lys Phe Ser Ala Gly Ser Tyr Pro Leu Leu Trp Ser
     320                 325                 330 tat gcc atg gga gta gga gtg gaa ctt gaa aac tcc atg gga ggt ttg       1239
Tyr Ala Met Gly Val Gly Val Glu Leu Glu Asn Ser Met Gly Gly Leu
335                 340                 345                 350 aac ttt ggc cga tct tac ttt gat cca gca tat ttt aga tta ggg caa       1287
Asn Phe Gly Arg Ser Tyr Phe Asp Pro Ala Tyr Phe Arg Leu Gly Gln
                 355                 360                 365 gag atg gta agg agg tca gct gga aag gtc agt tcc aca ttg gca tct       1335
Glu Met Val Arg Arg Ser Ala Gly Lys Val Ser Ser Thr Leu Ala Ser
             370                 375                 380 gaa ctc ggt atc act gcc gag gat gca agg ctt gtt tca gag att gca       1383
Glu Leu Gly Ile Thr Ala Glu Asp Ala Arg Leu Val Ser Glu Ile Ala
         385                 390                 395 atg cat act act gag gac aag atc agt aga gcg gtt gga ccc aga caa       1431
Met His Thr Thr Glu Asp Lys Ile Ser Arg Ala Val Gly Pro Arg Gln
     400                 405                 410 gcc caa gta tca ttt cta cac ggt gat caa agt gag aat gag cta ccg       1479
Ala Gln Val Ser Phe Leu His Gly Asp Gln Ser Glu Asn Glu Leu Pro
415                 420                 425                 430 aga ttg ggg ggc aag gaa gat agg agg gtc aaa cag agt cga gga gaa       1527
Arg Leu Gly Gly Lys Glu Asp Arg Arg Val Lys Gln Ser Arg Gly Glu
                 435                 440                 445 gcc agg gag agc tac aga gaa acc ggg ccc agc aga gca agt gat gcg       1575
Ala Arg Glu Ser Tyr Arg Glu Thr Gly Pro Ser Arg Ala Ser Asp Ala
             450                 455                 460 aga gct gcc cat ctt cca acc ggc aca ccc cta gac att gac act gca       1623
Arg Ala Ala His Leu Pro Thr Gly Thr Pro Leu Asp Ile Asp Thr Ala
         465                 470                 475 acg gag tcc agc caa gat ccg cag gac agt cga agg tca gct gac gcc       1671
Thr Glu Ser Ser Gln Asp Pro Gln Asp Ser Arg Arg Ser Ala Asp Ala
     480                 485                 490 ctg ctt agg ctg caa gcc atg gca gga atc tcg gaa gaa caa ggc tca       1719
```

```
Leu Leu Arg Leu Gln Ala Met Ala Gly Ile Ser Glu Glu Gln Gly Ser
495                 500                 505                 510 gac acg gac acc cct ata gtg tac aat gac aga aat ctt cta gac tag     1767
Asp Thr Asp Thr Pro Ile Val Tyr Asn Asp Arg Asn Leu Leu Asp
                515                 520                 525 gtgcgagagg ccgagggcca gaacaacatc cgcctaccat ccatcattgt tataaaaaac   1827
ttaggaacca ggtccacaca gccgccagcc catcaaccat ccactcccac gattggagcc   1887 a atg gca gaa gag cag gca cgc cat gtc aaa aac gga ctg gaa tgc atc   1936
  Met Ala Glu Glu Gln Ala Arg His Val Lys Asn Gly Leu Glu Cys Ile
                      530                 535                 540 cgg gct ctc aag gcc gag ccc atc ggc tca ctg gcc atc gag gaa gct     1984
Arg Ala Leu Lys Ala Glu Pro Ile Gly Ser Leu Ala Ile Glu Glu Ala
            545                 550                 555 atg gca gca tgg tca gaa ata tca gac aac cca gga cag gag cga gcc     2032
Met Ala Ala Trp Ser Glu Ile Ser Asp Asn Pro Gly Gln Glu Arg Ala
        560                 565                 570 acc tgc agg gaa gag aag gca ggc agt tcg ggt ctc agc aaa cca tgc     2080
Thr Cys Arg Glu Glu Lys Ala Gly Ser Ser Gly Leu Ser Lys Pro Cys
    575                 580                 585 ctc tca gca att gga tca act gaa ggc ggt gca cct cgc atc cgc ggt     2128
Leu Ser Ala Ile Gly Ser Thr Glu Gly Gly Ala Pro Arg Ile Arg Gly
590                 595                 600                 605 cag gga cct gga gag agc gat gac gac gct gaa act ttg gga atc ccc     2176
Gln Gly Pro Gly Glu Ser Asp Asp Asp Ala Glu Thr Leu Gly Ile Pro
                610                 615                 620 cca aga aat ctc cag gca tca agc act ggg tta cag tgt tat tac gtt     2224
Pro Arg Asn Leu Gln Ala Ser Ser Thr Gly Leu Gln Cys Tyr Tyr Val
            625                 630                 635 tat gat cac agc ggt gaa gcg gtt aag gga atc caa gat gct gac tct     2272
Tyr Asp His Ser Gly Glu Ala Val Lys Gly Ile Gln Asp Ala Asp Ser
        640                 645                 650 atc atg gtt caa tca ggc ctt gat ggt gat agc acc ctc tca gga gga     2320
Ile Met Val Gln Ser Gly Leu Asp Gly Asp Ser Thr Leu Ser Gly Gly
    655                 660                 665 gac aat gaa tct gaa aac agc gat gtg gat att ggc gaa cct gat acc     2368
Asp Asn Glu Ser Glu Asn Ser Asp Val Asp Ile Gly Glu Pro Asp Thr
670                 675                 680                 685 gag gga tat gct atc act gac cgg gga tct gct ccc atc tct atg ggg     2416
Glu Gly Tyr Ala Ile Thr Asp Arg Gly Ser Ala Pro Ile Ser Met Gly
                690                 695                 700 ttc agg gct tct gat gtt gaa act gca gaa gga ggg gag atc cac gag     2464
Phe Arg Ala Ser Asp Val Glu Thr Ala Glu Gly Gly Glu Ile His Glu
            705                 710                 715 ctc ctg aga ctc caa tcc aga ggc aac aac ttt ccg aag ctt ggg aaa     2512
Leu Leu Arg Leu Gln Ser Arg Gly Asn Asn Phe Pro Lys Leu Gly Lys
        720                 725                 730 act ctc aat gtt cct ccg ccc ccg gac ccc ggt agg gcc agc act tcc     2560
Thr Leu Asn Val Pro Pro Pro Pro Asp Pro Gly Arg Ala Ser Thr Ser
    735                 740                 745 ggg aca ccc att aaa aag ggc aca gac gcg aga tta gcc tca ttt gga     2608
Gly Thr Pro Ile Lys Lys Gly Thr Asp Ala Arg Leu Ala Ser Phe Gly
750                 755                 760                 765 acg gag atc gcg tct tta ttg aca ggt ggt gca acc caa tgt gct cga     2656
Thr Glu Ile Ala Ser Leu Leu Thr Gly Gly Ala Thr Gln Cys Ala Arg
                770                 775                 780 aag tca ccc tcg gaa cca tca ggg cca ggt gca cct gcg ggg aat gtc     2704
Lys Ser Pro Ser Glu Pro Ser Gly Pro Gly Ala Pro Ala Gly Asn Val
            785                 790                 795
```

```
ccc gag tgt gtg agc aat gcc gca ctg ata cag gag tgg aca ccc gaa      2752
Pro Glu Cys Val Ser Asn Ala Ala Leu Ile Gln Glu Trp Thr Pro Glu
        800                 805                 810 tct ggt acc aca atc tcc ccg aga tcc cag aat aat gaa gaa ggg gga      2800
Ser Gly Thr Thr Ile Ser Pro Arg Ser Gln Asn Asn Glu Glu Gly Gly
    815                 820                 825 gac tat tat gat gat gag ctg ttc tct gat gtc caa gat att aaa aca      2848
Asp Tyr Tyr Asp Asp Glu Leu Phe Ser Asp Val Gln Asp Ile Lys Thr
830                 835                 840                 845 gcc ttg gcc aaa ata cac gag gat aat cag aag ata atc tcc aag cta      2896
Ala Leu Ala Lys Ile His Glu Asp Asn Gln Lys Ile Ile Ser Lys Leu
                850                 855                 860 gaa tca ctg ctg tta ttg aag gga gaa gtt gag tca att aag aag cag      2944
Glu Ser Leu Leu Leu Leu Lys Gly Glu Val Glu Ser Ile Lys Lys Gln
            865                 870                 875 atc aac agg caa aat atc agc ata tcc acc ctg gaa gga cac ctc tca      2992
Ile Asn Arg Gln Asn Ile Ser Ile Ser Thr Leu Glu Gly His Leu Ser
        880                 885                 890 agc atc atg atc gcc att cct gga ctt ggg aag gat ccc aac gac ccc      3040
Ser Ile Met Ile Ala Ile Pro Gly Leu Gly Lys Asp Pro Asn Asp Pro
    895                 900                 905 act gca gat gtc gaa atc aat ccc gac ttg aaa ccc atc ata ggc aga      3088
Thr Ala Asp Val Glu Ile Asn Pro Asp Leu Lys Pro Ile Ile Gly Arg
910                 915                 920                 925 gat tca ggc cga gca ctg gcc gaa gtt ctc aag aaa ccc gtt gcc agc      3136
Asp Ser Gly Arg Ala Leu Ala Glu Val Leu Lys Lys Pro Val Ala Ser
                930                 935                 940 cga caa ctc caa gga atg aca aat gga cgg acc agt tcc aga gga cag      3184
Arg Gln Leu Gln Gly Met Thr Asn Gly Arg Thr Ser Ser Arg Gly Gln
            945                 950                 955 ctg ctg aag gaa ttt cag cta aag ccg atc ggg aaa aag atg agc tca      3232
Leu Leu Lys Glu Phe Gln Leu Lys Pro Ile Gly Lys Lys Met Ser Ser
        960                 965                 970 gcc gtc ggg ttt gtt cct gac acc ggc cct gca tca cgc agt gta atc      3280
Ala Val Gly Phe Val Pro Asp Thr Gly Pro Ala Ser Arg Ser Val Ile
    975                 980                 985 cgc tcc att ata aaa tcc agc cgg cta gag gag  gat cgg aag cgt tac     3328
Arg Ser Ile Ile Lys Ser Ser Arg Leu Glu Glu  Asp Arg Lys Arg Tyr
990                 995                 1000                1005 ctg atg act ctc ctt  gat gat atc aaa gga  gcc aat gat ctt gcc        3373
Leu Met Thr Leu Leu  Asp Asp Ile Lys Gly  Ala Asn Asp Leu Ala
                1010                1015                1020 aag ttc cac cag atg  ctg atg aag ata ata  atg aag tag ctacagctca     3422
Lys Phe His Gln Met  Leu Met Lys Ile Ile  Met Lys
                1025                1030 acttacctgc caaccccatg ccagtcgacc caactagcct accctccatc attgttataa    3482
aaaacttagg aaccaggtcc acacagccgc cagcccatca acgcgtacga tg atg cag    3540
                                                        Met Gln att ttc gtc aaa aca ttg aca gga aag acc atc aca ctg gaa gtg          3585
Ile Phe Val Lys Thr Leu Thr Gly Lys Thr Ile Thr Leu Glu Val
1035                1040                1045 gag cca agc gac act att gag aac gtc aaa gcc aag att cag gac          3630
Glu Pro Ser Asp Thr Ile Glu Asn Val Lys Ala Lys Ile Gln Asp
1050                1055                1060 aag gag ggc atc cca cca gac cag cag agg ctg att ttt gcc gga          3675
Lys Glu Gly Ile Pro Pro Asp Gln Gln Arg Leu Ile Phe Ala Gly
1065                1070                1075 aag cag ctg gag gac gga cgc aca ctc agt gac tac aat atc cag          3720
Lys Gln Leu Glu Asp Gly Arg Thr Leu Ser Asp Tyr Asn Ile Gln
```

```
                    1080                1085                1090
aag  gaa  agt  act  ctg  cat  ctg  gtc  ctt  cgc  ctg  cgc  ggc  gga  aga         3765
Lys  Glu  Ser  Thr  Leu  His  Leu  Val  Leu  Arg  Leu  Arg  Gly  Gly  Arg
1095                1100                1105 gct  ctc  gtc  gcc  cag  tgt  ctg  gtc  tgc  gtt  cct  tgg  gac  gca  cgg         3810
Ala  Leu  Val  Ala  Gln  Cys  Leu  Val  Cys  Val  Pro  Trp  Asp  Ala  Arg
1110                1115                1120 ccc  cca  ccc  gcc  gcc  ccc  agt  ttc  cgg  cag  gtg  agt  tgt  ctc  aaa         3855
Pro  Pro  Pro  Ala  Ala  Pro  Ser  Phe  Arg  Gln  Val  Ser  Cys  Leu  Lys
1125                1130                1135 gag  ttg  gtt  gct  cgg  gtg  ttg  cag  cgg  ctt  tgt  gaa  cgc  gga  gca         3900
Glu  Leu  Val  Ala  Arg  Val  Leu  Gln  Arg  Leu  Cys  Glu  Arg  Gly  Ala
1140                1145                1150 aag  aac  gtc  ctt  gcc  ttt  ggc  ttc  gct  ttg  ctc  gat  gga  gca  cgc         3945
Lys  Asn  Val  Leu  Ala  Phe  Gly  Phe  Ala  Leu  Leu  Asp  Gly  Ala  Arg
1155                1160                1165 gga  ggc  cct  cct  gag  gca  ttc  act  act  agc  gtc  cgg  tcc  tac  ctg         3990
Gly  Gly  Pro  Pro  Glu  Ala  Phe  Thr  Thr  Ser  Val  Arg  Ser  Tyr  Leu
1170                1175                1180 ccc  aac  aca  gtg  acc  gac  gct  ctg  aga  ggt  tca  ggt  gcc  tgg  ggt         4035
Pro  Asn  Thr  Val  Thr  Asp  Ala  Leu  Arg  Gly  Ser  Gly  Ala  Trp  Gly
1185                1190                1195 ctg  ctg  ctg  cgg  agg  gtg  ggt  gat  gat  gtt  ctg  gtt  cac  ctc  ctg         4080
Leu  Leu  Leu  Arg  Arg  Val  Gly  Asp  Asp  Val  Leu  Val  His  Leu  Leu
1200                1205                1210 gcc  cgg  tgt  gcc  ctg  ttc  gtg  ctg  gtg  gct  ccc  tcc  tgc  gca  tac         4125
Ala  Arg  Cys  Ala  Leu  Phe  Val  Leu  Val  Ala  Pro  Ser  Cys  Ala  Tyr
1215                1220                1225 cag  gtc  tgc  gga  ccc  cca  ctt  tat  cag  ctc  ggc  gct  gct  act  cag         4170
Gln  Val  Cys  Gly  Pro  Pro  Leu  Tyr  Gln  Leu  Gly  Ala  Ala  Thr  Gln
1230                1235                1240 gcc  cgc  cca  cca  cca  cac  gcc  tca  ggt  cca  aga  cgc  cgg  ctg  ggc         4215
Ala  Arg  Pro  Pro  Pro  His  Ala  Ser  Gly  Pro  Arg  Arg  Arg  Leu  Gly
1245                1250                1255 tgc  gaa  cgg  gca  tgg  aat  cat  agc  gtg  cgg  gag  gca  ggt  gtg  cct         4260
Cys  Glu  Arg  Ala  Trp  Asn  His  Ser  Val  Arg  Glu  Ala  Gly  Val  Pro
1260                1265                1270 ctc  ggc  ctg  cca  gcc  ccc  gga  gca  agg  aga  cgc  ggt  gga  tcc  gcc         4305
Leu  Gly  Leu  Pro  Ala  Pro  Gly  Ala  Arg  Arg  Arg  Gly  Gly  Ser  Ala
1275                1280                1285 agt  cgc  tca  ctc  ccc  ttg  cct  aag  agg  cca  aga  aga  gga  gcc  gcc         4350
Ser  Arg  Ser  Leu  Pro  Leu  Pro  Lys  Arg  Pro  Arg  Arg  Gly  Ala  Ala
1290                1295                1300 cct  gaa  ccc  gag  aga  aca  cct  gtc  ggc  cag  ggc  tcc  tgg  gct  cac         4395
Pro  Glu  Pro  Glu  Arg  Thr  Pro  Val  Gly  Gln  Gly  Ser  Trp  Ala  His
1305                1310                1315 ccc  gga  agg  acc  agg  ggc  cca  agc  gat  agg  ggc  ttc  tgt  gtt  gtg         4440
Pro  Gly  Arg  Thr  Arg  Gly  Pro  Ser  Asp  Arg  Gly  Phe  Cys  Val  Val
1320                1325                1330 tca  cca  gcc  agg  cct  gcc  gaa  gag  gct  acc  tcc  ttg  gaa  gga  gcc         4485
Ser  Pro  Ala  Arg  Pro  Ala  Glu  Glu  Ala  Thr  Ser  Leu  Glu  Gly  Ala
1335                1340                1345 ctc  agt  ggc  acc  agg  cat  tct  cat  cca  tct  gtg  ggt  agg  cag  cat         4530
Leu  Ser  Gly  Thr  Arg  His  Ser  His  Pro  Ser  Val  Gly  Arg  Gln  His
1350                1355                1360 cat  gcc  ggc  ccc  ccc  tct  aca  agc  aga  cct  ccc  aga  cct  tgg  gac         4575
His  Ala  Gly  Pro  Pro  Ser  Thr  Ser  Arg  Pro  Pro  Arg  Pro  Trp  Asp
1365                1370                1375 aca  ccc  tgc  cca  cca  gtg  tat  gcc  gag  acc  aag  cac  ttt  ttg  tat         4620
```

```
Thr Pro Cys Pro Pro Val Tyr Ala Glu Thr Lys His Phe Leu Tyr
1380            1385                1390 tcc agt ggc gat aaa gag cag ctc cgg ccc tct ttt ctg ctc tca    4665
Ser Ser Gly Asp Lys Glu Gln Leu Arg Pro Ser Phe Leu Leu Ser
1395            1400                1405 agc ctc cgc ccc tct ctg acc gga gct cgc agg ctg gtg gag acc    4710
Ser Leu Arg Pro Ser Leu Thr Gly Ala Arg Arg Leu Val Glu Thr
1410            1415                1420 atc ttt ctg ggc tca aga cca tgg atg cca ggc acc ccc cgc aga    4755
Ile Phe Leu Gly Ser Arg Pro Trp Met Pro Gly Thr Pro Arg Arg
1425            1430                1435 ctg ccc agg ctc ccc cag cgg tac tgg cag atg cgc cct ctc ttt    4800
Leu Pro Arg Leu Pro Gln Arg Tyr Trp Gln Met Arg Pro Leu Phe
1440            1445                1450 ctg gaa ctt ctg ggt aac cac gcc cag tgc cca tat ggc gtc ctg    4845
Leu Glu Leu Leu Gly Asn His Ala Gln Cys Pro Tyr Gly Val Leu
1455            1460                1465 ctg aag acc cac tgt cct ctg agg gcc gcc gtg acc cca gcc gcc    4890
Leu Lys Thr His Cys Pro Leu Arg Ala Ala Val Thr Pro Ala Ala
1470            1475                1480 ggt gtg tgt gct aga gaa aaa ccc cag ggc tca gtg gct gca cct    4935
Gly Val Cys Ala Arg Glu Lys Pro Gln Gly Ser Val Ala Ala Pro
1485            1490                1495 gaa gag gag gac act gac cct cgc cgc ctt gtc cag ttg ctc agg    4980
Glu Glu Glu Asp Thr Asp Pro Arg Arg Leu Val Gln Leu Leu Arg
1500            1505                1510 cag cat tca tca cca tgg cag gtg tac ggc ttc gtg agg gct tgc    5025
Gln His Ser Ser Pro Trp Gln Val Tyr Gly Phe Val Arg Ala Cys
1515            1520                1525 ctg cgg aga ctg gtc ccc ccc gga ttg tgg gga tct cgg cac aac    5070
Leu Arg Arg Leu Val Pro Pro Gly Leu Trp Gly Ser Arg His Asn
1530            1535                1540 gaa cgg cgc ttt ctg agg aat aca aag aag ttt atc tcc ctg ggc    5115
Glu Arg Arg Phe Leu Arg Asn Thr Lys Lys Phe Ile Ser Leu Gly
1545            1550                1555 aag cat gca aag ctc agc ttg cag gag ctg aca tgg aag atg agc    5160
Lys His Ala Lys Leu Ser Leu Gln Glu Leu Thr Trp Lys Met Ser
1560            1565                1570 gtt aga gga tgc gca tgg ctc agg cgg tca cct gga gtt gga tgc    5205
Val Arg Gly Cys Ala Trp Leu Arg Arg Ser Pro Gly Val Gly Cys
1575            1580                1585 gtt cca gca gca gag cac agg ctg cgc gaa gag att ctc gca aag    5250
Val Pro Ala Ala Glu His Arg Leu Arg Glu Glu Ile Leu Ala Lys
1590            1595                1600 ttc ctg cac tgg ctt atg agc gtc tac gtg gtc gaa ctg ctg cgg    5295
Phe Leu His Trp Leu Met Ser Val Tyr Val Val Glu Leu Leu Arg
1605            1610                1615 tct ttc ttc tac gtg aca gag acc act ttt cag aag aac aga ctg    5340
Ser Phe Phe Tyr Val Thr Glu Thr Thr Phe Gln Lys Asn Arg Leu
1620            1625                1630 ttc ttc tac agg aag tcc gtc tgg agc aag ctc cag agt att ggt    5385
Phe Phe Tyr Arg Lys Ser Val Trp Ser Lys Leu Gln Ser Ile Gly
1635            1640                1645 att aga cag cac ctt aag aga gtt cag ctt aga gag ctg tcc gaa    5430
Ile Arg Gln His Leu Lys Arg Val Gln Leu Arg Glu Leu Ser Glu
1650            1655                1660 gct gaa gtc cgc cag cac cgc gaa gct cgc ccc gcc ctc ctg acc    5475
Ala Glu Val Arg Gln His Arg Glu Ala Arg Pro Ala Leu Leu Thr
1665            1670                1675
```

| | | | | | | | | | | | | | | |
|---|---|---|---|---|---|---|---|---|---|---|---|---|---|---|
| tct<br>Ser<br>1680 | cgg<br>Arg | ctg<br>Leu | cgg<br>Arg | ttt<br>Phe | att<br>Ile<br>1685 | ccc<br>Pro | aaa<br>Lys | ccc<br>Pro | gat<br>Asp | ggc<br>Gly<br>1690 | ctt<br>Leu | aga<br>Arg | cct<br>Pro | atc<br>Ile | 5520 |
| gtg<br>Val<br>1695 | aat<br>Asn | atg<br>Met | gat<br>Asp | tac<br>Tyr | gtc<br>Val<br>1700 | gtg<br>Val | ggt<br>Gly | gcc<br>Ala | cgc<br>Arg | act<br>Thr<br>1705 | ttc<br>Phe | aga<br>Arg | agg<br>Arg | gag<br>Glu | 5565 |
| aag<br>Lys<br>1710 | agg<br>Arg | gcc<br>Ala | gag<br>Glu | aga<br>Arg | ctg<br>Leu<br>1715 | aca<br>Thr | tct<br>Ser | cgc<br>Arg | gtg<br>Val | aag<br>Lys<br>1720 | gca<br>Ala | ctt<br>Leu | ttt<br>Phe | tct<br>Ser | 5610 |
| gtg<br>Val<br>1725 | ctt<br>Leu | aat<br>Asn | tat<br>Tyr | gaa<br>Glu | aga<br>Arg<br>1730 | gcc<br>Ala | cgc<br>Arg | aga<br>Arg | cct<br>Pro | ggt<br>Gly<br>1735 | ctt<br>Leu | ctc<br>Leu | gga<br>Gly | gcc<br>Ala | 5655 |
| agc<br>Ser<br>1740 | gtg<br>Val | ctc<br>Leu | ggc<br>Gly | ctg<br>Leu | gat<br>Asp<br>1745 | gat<br>Asp | atc<br>Ile | cat<br>His | cgg<br>Arg | gct<br>Ala<br>1750 | tgg<br>Trp | cgc<br>Arg | acc<br>Thr | ttt<br>Phe | 5700 |
| gtg<br>Val<br>1755 | ctt<br>Leu | cgg<br>Arg | gtg<br>Val | agg<br>Arg | gca<br>Ala<br>1760 | cag<br>Gln | gat<br>Asp | cct<br>Pro | cct<br>Pro | cct<br>Pro<br>1765 | gag<br>Glu | ctt<br>Leu | tat<br>Tyr | ttt<br>Phe | 5745 |
| gtg<br>Val<br>1770 | aaa<br>Lys | gtt<br>Val | gat<br>Asp | gtt<br>Val | act<br>Thr<br>1775 | ggt<br>Gly | gct<br>Ala | tac<br>Tyr | gat<br>Asp | aca<br>Thr<br>1780 | atc<br>Ile | cct<br>Pro | cag<br>Gln | gac<br>Asp | 5790 |
| cgg<br>Arg<br>1785 | ctc<br>Leu | acc<br>Thr | gag<br>Glu | gtg<br>Val | atc<br>Ile<br>1790 | gcc<br>Ala | tct<br>Ser | att<br>Ile | atc<br>Ile | aaa<br>Lys<br>1795 | ccc<br>Pro | cag<br>Gln | aac<br>Asn | acc<br>Thr | 5835 |
| tac<br>Tyr<br>1800 | tgc<br>Cys | gtg<br>Val | aga<br>Arg | agg<br>Arg | tac<br>Tyr<br>1805 | gcc<br>Ala | gtc<br>Val | gtt<br>Val | cag<br>Gln | aaa<br>Lys<br>1810 | gcc<br>Ala | gca<br>Ala | cac<br>His | gga<br>Gly | 5880 |
| cac<br>His<br>1815 | gtg<br>Val | cgc<br>Arg | aaa<br>Lys | gct<br>Ala | ttc<br>Phe<br>1820 | aaa<br>Lys | tcc<br>Ser | cac<br>His | gtg<br>Val | tct<br>Ser<br>1825 | acc<br>Thr | ttg<br>Leu | aca<br>Thr | gac<br>Asp | 5925 |
| ctc<br>Leu<br>1830 | cag<br>Gln | cct<br>Pro | tat<br>Tyr | atg<br>Met | cgg<br>Arg<br>1835 | cag<br>Gln | ttt<br>Phe | gtc<br>Val | gca<br>Ala | cac<br>His<br>1840 | ctg<br>Leu | cag<br>Gln | gag<br>Glu | act<br>Thr | 5970 |
| agc<br>Ser<br>1845 | ccc<br>Pro | ttg<br>Leu | agg<br>Arg | gac<br>Asp | gct<br>Ala<br>1850 | gtg<br>Val | gtc<br>Val | atc<br>Ile | gaa<br>Glu | cag<br>Gln<br>1855 | tcc<br>Ser | agc<br>Ser | tct<br>Ser | ctc<br>Leu | 6015 |
| aat<br>Asn<br>1860 | gag<br>Glu | gca<br>Ala | tcc<br>Ser | tca<br>Ser | ggc<br>Gly<br>1865 | ctg<br>Leu | ttt<br>Phe | gat<br>Asp | gtg<br>Val | ttc<br>Phe<br>1870 | ctg<br>Leu | cgc<br>Arg | ttt<br>Phe | atg<br>Met | 6060 |
| tgc<br>Cys<br>1875 | cac<br>His | cac<br>His | gcc<br>Ala | gtg<br>Val | cgg<br>Arg<br>1880 | att<br>Ile | agg<br>Arg | ggc<br>Gly | aag<br>Lys | tct<br>Ser<br>1885 | tac<br>Tyr | gtg<br>Val | cag<br>Gln | tgc<br>Cys | 6105 |
| cag<br>Gln<br>1890 | ggc<br>Gly | atc<br>Ile | cca<br>Pro | cag<br>Gln | ggt<br>Gly<br>1895 | agc<br>Ser | atc<br>Ile | ctg<br>Leu | agc<br>Ser | aca<br>Thr<br>1900 | ctg<br>Leu | ctg<br>Leu | tgt<br>Cys | agc<br>Ser | 6150 |
| ctg<br>Leu<br>1905 | tgc<br>Cys | tat<br>Tyr | ggc<br>Gly | gat<br>Asp | atg<br>Met<br>1910 | gag<br>Glu | aat<br>Asn | aaa<br>Lys | ttg<br>Leu | ttc<br>Phe<br>1915 | gcc<br>Ala | ggt<br>Gly | atc<br>Ile | aga<br>Arg | 6195 |
| aga<br>Arg<br>1920 | gac<br>Asp | ggt<br>Gly | ttg<br>Leu | ctc<br>Leu | ctg<br>Leu<br>1925 | agg<br>Arg | ctg<br>Leu | ttc<br>Phe | ctg<br>Leu | ctg<br>Leu<br>1930 | gtt<br>Val | acc<br>Thr | ccc<br>Pro | cat<br>His | 6240 |
| ctg<br>Leu<br>1935 | act<br>Thr | cat<br>His | gcc<br>Ala | aaa<br>Lys | aca<br>Thr<br>1940 | ttt<br>Phe | ttg<br>Leu | cgg<br>Arg | act<br>Thr | ctg<br>Leu<br>1945 | gtt<br>Val | agg<br>Arg | ggc<br>Gly | gtg<br>Val | 6285 |
| cca<br>Pro<br>1950 | gag<br>Glu | tat<br>Tyr | ggc<br>Gly | tgt<br>Cys | gtt<br>Val<br>1955 | gtg<br>Val | aat<br>Asn | ttg<br>Leu | cgg<br>Arg | aaa<br>Lys<br>1960 | act<br>Thr | gtg<br>Val | gtt<br>Val | aat<br>Asn | 6330 |
| ttc<br>Phe<br>1965 | cca<br>Pro | gtg<br>Val | gag<br>Glu | gac<br>Asp | gaa<br>Glu<br>1970 | gct<br>Ala | ctc<br>Leu | gga<br>Gly | ggc<br>Gly | aca<br>Thr<br>1975 | gct<br>Ala | ttt<br>Phe | gtt<br>Val | cag<br>Gln | 6375 |

```
atg  cct  gcc  cac  ggc  ctg  ttc  cca  tgg  tgc  gga  ctg  ctg  ctc  gat              6420
Met  Pro  Ala  His  Gly  Leu  Phe  Pro  Trp  Cys  Gly  Leu  Leu  Leu  Asp
1980                    1985                    1990 acc  cgg  acc  ctc  gag  gtg  cag  tcc  gat  tat  agt  tcc  tat  gca  aga              6465
Thr  Arg  Thr  Leu  Glu  Val  Gln  Ser  Asp  Tyr  Ser  Ser  Tyr  Ala  Arg
1995                    2000                    2005 aca  tca  att  cgg  gct  agc  ctg  act  ttc  aac  agg  ggc  ttc  aag  gcc              6510
Thr  Ser  Ile  Arg  Ala  Ser  Leu  Thr  Phe  Asn  Arg  Gly  Phe  Lys  Ala
2010                    2015                    2020 ggc  cgg  aat  atg  aga  agg  aaa  ctg  ttc  gga  gtg  ttg  aga  ctt  aag              6555
Gly  Arg  Asn  Met  Arg  Arg  Lys  Leu  Phe  Gly  Val  Leu  Arg  Leu  Lys
2025                    2030                    2035 tgt  cat  agt  ctt  ttt  ttg  gac  ttg  cag  gtc  aat  tct  ctc  cag  aca              6600
Cys  His  Ser  Leu  Phe  Leu  Asp  Leu  Gln  Val  Asn  Ser  Leu  Gln  Thr
2040                    2045                    2050 gtg  tgt  acc  aac  att  tat  aaa  atc  ctc  ttg  ctg  cag  gct  tac  aga              6645
Val  Cys  Thr  Asn  Ile  Tyr  Lys  Ile  Leu  Leu  Leu  Gln  Ala  Tyr  Arg
2055                    2060                    2065 ttc  cat  gcc  tgc  gtc  ctg  cag  ctg  cct  ttc  cac  cag  cag  gtg  tgg              6690
Phe  His  Ala  Cys  Val  Leu  Gln  Leu  Pro  Phe  His  Gln  Gln  Val  Trp
2070                    2075                    2080 aaa  aac  cct  acc  ttc  ttc  ctg  cgg  gtg  att  agc  gac  acc  gcc  agt              6735
Lys  Asn  Pro  Thr  Phe  Phe  Leu  Arg  Val  Ile  Ser  Asp  Thr  Ala  Ser
2085                    2090                    2095 ctt  tgc  tac  tcc  atc  ttg  aaa  gca  aaa  aac  gct  ggc  atg  agc  ttg              6780
Leu  Cys  Tyr  Ser  Ile  Leu  Lys  Ala  Lys  Asn  Ala  Gly  Met  Ser  Leu
2100                    2105                    2110 gga  gct  aag  ggc  gcc  gct  gga  cct  ctg  ccc  agt  gaa  gca  gtc  cag              6825
Gly  Ala  Lys  Gly  Ala  Ala  Gly  Pro  Leu  Pro  Ser  Glu  Ala  Val  Gln
2115                    2120                    2125 tgg  ctg  tgt  cat  cag  gct  ttc  ctc  ctt  aaa  ctg  aca  cgc  cac  cgc              6870
Trp  Leu  Cys  His  Gln  Ala  Phe  Leu  Leu  Lys  Leu  Thr  Arg  His  Arg
2130                    2135                    2140 gtg  act  tac  gtc  cca  ctc  ctg  ggc  tcc  ctg  aga  act  gct  cag  acc              6915
Val  Thr  Tyr  Val  Pro  Leu  Leu  Gly  Ser  Leu  Arg  Thr  Ala  Gln  Thr
2145                    2150                    2155 cag  ctt  tcc  cgg  aag  ctt  cca  ggc  act  acc  ctt  acc  gca  ctc  gaa              6960
Gln  Leu  Ser  Arg  Lys  Leu  Pro  Gly  Thr  Thr  Leu  Thr  Ala  Leu  Glu
2160                    2165                    2170 gca  gcc  gcc  aac  cct  gcc  ctg  ccc  tcc  gac  ttt  aag  act  atc  ctg              7005
Ala  Ala  Ala  Asn  Pro  Ala  Leu  Pro  Ser  Asp  Phe  Lys  Thr  Ile  Leu
2175                    2180                    2185 gac  aca  gag  ctg  aag  ttg  agc  gat  tac  gag  ggc  cgc  ctg  atc  cag              7050
Asp  Thr  Glu  Leu  Lys  Leu  Ser  Asp  Tyr  Glu  Gly  Arg  Leu  Ile  Gln
2190                    2195                    2200 aac  tcc  ttg  act  ggc  aag  cca  att  cct  aat  cca  ttg  ctg  ggc  ctg              7095
Asn  Ser  Leu  Thr  Gly  Lys  Pro  Ile  Pro  Asn  Pro  Leu  Leu  Gly  Leu
2205                    2210                    2215 gac  tca  act  tga  gcgcgcagcg  ctgacgtctc  gcgatcgata  ctagtacaac                      7147
Asp  Ser  Thr
2220 ctaaatccat  tataaaaaac  ttaggagcaa  agtgattgcc  tcccaaggtc  caca atg                     7204
                                                                 Met aca  gag  acc  tac  gac  ttc  gac  aag  tcg  gca  tgg  gac  atc  aaa  ggg              7249
Thr  Glu  Thr  Tyr  Asp  Phe  Asp  Lys  Ser  Ala  Trp  Asp  Ile  Lys  Gly
     2225                    2230                    2235 tcg  atc  gct  ccg  ata  caa  ccc  acc  acc  tac  agt  gat  ggc  agg  ctg              7294
Ser  Ile  Ala  Pro  Ile  Gln  Pro  Thr  Thr  Tyr  Ser  Asp  Gly  Arg  Leu
         2240                    2245                    2250
```

```
gtg ccc cag gtc aga gtc ata gat cct ggt cta ggc gac agg aag      7339
Val Pro Gln Val Arg Val Ile Asp Pro Gly Leu Gly Asp Arg Lys
    2255            2260                2265 gat gaa tgc ttt atg tac atg ttt ctg ctg ggg gtt gtt gag gac      7384
Asp Glu Cys Phe Met Tyr Met Phe Leu Leu Gly Val Val Glu Asp
2270            2275                2280 agc gat tcc cta ggg cct cca atc ggg cga gca ttt ggg ttc ctg      7429
Ser Asp Ser Leu Gly Pro Pro Ile Gly Arg Ala Phe Gly Phe Leu
    2285            2290                2295 ccc tta ggt gtt ggc aga tcc aca gca aag ccc gaa aaa ctc ctc      7474
Pro Leu Gly Val Gly Arg Ser Thr Ala Lys Pro Glu Lys Leu Leu
2300            2305                2310 aaa gag gcc act gag ctt gac ata gtt gtt aga cgt aca gca ggg      7519
Lys Glu Ala Thr Glu Leu Asp Ile Val Val Arg Arg Thr Ala Gly
    2315            2320                2325 ctc aat gaa aaa ctg gtg ttc tac aac aac acc cca cta act ctc      7564
Leu Asn Glu Lys Leu Val Phe Tyr Asn Asn Thr Pro Leu Thr Leu
2330            2335                2340 ctc aca cct tgg aga aag gtc cta aca aca ggg agt gtc ttc aac      7609
Leu Thr Pro Trp Arg Lys Val Leu Thr Thr Gly Ser Val Phe Asn
    2345            2350                2355 gca aac caa gtg tgc aat gcg gtt aat ctg ata ccg ctc gat acc      7654
Ala Asn Gln Val Cys Asn Ala Val Asn Leu Ile Pro Leu Asp Thr
2360            2365                2370 ccg cag agg ttc cgt gtt gtt tat atg agc atc acc cgt ctt tcg      7699
Pro Gln Arg Phe Arg Val Val Tyr Met Ser Ile Thr Arg Leu Ser
    2375            2380                2385 gat aac ggg tat tac acc gtt cct aga aga atg ctg gaa ttc aga      7744
Asp Asn Gly Tyr Tyr Thr Val Pro Arg Arg Met Leu Glu Phe Arg
2390            2395                2400 tcg gtc aat gca gtg gcc ttc aac ctg ctg gtg acc ctt agg att      7789
Ser Val Asn Ala Val Ala Phe Asn Leu Leu Val Thr Leu Arg Ile
    2405            2410                2415 gac aag gcg ata ggc cct ggg aag atc atc gac aat aca gag caa      7834
Asp Lys Ala Ile Gly Pro Gly Lys Ile Ile Asp Asn Thr Glu Gln
2420            2425                2430 ctt cct gag gca aca ttt atg gtc cac atc ggg aac ttc agg aga      7879
Leu Pro Glu Ala Thr Phe Met Val His Ile Gly Asn Phe Arg Arg
    2435            2440                2445 aag aag agt gaa gtc tac tct gcc gat tat tgc aaa atg aaa atc      7924
Lys Lys Ser Glu Val Tyr Ser Ala Asp Tyr Cys Lys Met Lys Ile
2450            2455                2460 gaa aag atg ggc ctg gtt ttt gca ctt ggt ggg ata ggg ggc acc      7969
Glu Lys Met Gly Leu Val Phe Ala Leu Gly Gly Ile Gly Gly Thr
    2465            2470                2475 agt ctt cac att aga agc aca ggc aaa atg agc aag act ctc cat      8014
Ser Leu His Ile Arg Ser Thr Gly Lys Met Ser Lys Thr Leu His
2480            2485                2490 gca caa ctc ggg ttc aag aag acc tta tgt tac ccg ctg atg gat      8059
Ala Gln Leu Gly Phe Lys Lys Thr Leu Cys Tyr Pro Leu Met Asp
    2495            2500                2505 atc aat gaa gac ctt aat cga tta ctc tgg agg agc aga tgc aag      8104
Ile Asn Glu Asp Leu Asn Arg Leu Leu Trp Arg Ser Arg Cys Lys
2510            2515                2520 ata gta aga atc cag gca gtt ttg cag cca tca gtt cct caa gaa      8149
Ile Val Arg Ile Gln Ala Val Leu Gln Pro Ser Val Pro Gln Glu
    2525            2530                2535 ttc cgc att tac gac gac gtg atc ata aat gat gac caa gga cta      8194
Phe Arg Ile Tyr Asp Asp Val Ile Ile Asn Asp Asp Gln Gly Leu
```

-continued

```
            2540                2545                2550
ttc aaa gtt ctg tag accgtagtgc ccagcaatgc ccgaaaacga ccccctcac    8249
Phe Lys Val Leu
    2555 aatgacagcc agaaggcccg acaaaaaag cccctccga aagactccac ggaccaagcg   8309
agaggccagc cagcagccga cggcaagcgc gaacaccagg cggcccagc acagaacagc   8369
cctgacacaa ggccaccacc agccaccca atctgcatcc tcctcgtggg accccgagg    8429
accaaccccc aaggctgccc ccgatccaaa ccaccaaccg catccccacc accccggga   8489
aagaaacccc cagcaattgg aaggcccctc cccctcttcc tcaacacaag aactccacaa   8549
ccgaaccgca caagcgaccg aggtgaccca accgcaggca tccgactccc tagacagatc   8609
ctctctcccc ggcaaactaa acaaaactta gggccaagga acatacacac ccaacagaac   8669
ccagaccccg gcccacggcg ccgcgccccc aaccccgac aaccagaggg agcccccaac    8729
caatcccgcc ggctcccccg gtgcccacag gcagggacac caaccccga acagacccag    8789
cacccaacca tcgacaatcc aagacggggg ggccccccca aaaaaggcc ccagggggcc    8849
gacagccagc accgcgagga agcccaccca ccccacacac gaccacggca accaaaccag   8909
aacccagacc accctgggcc accagctccc agactcggcc atcaccccgc agaaaggaaa   8969
ggccacaacc cgcgcacccc agccccgatc cggcggggag ccacccaacc cgaaccagca   9029
cccaagagcg atcccgaag gacccccgaa ccgcaaagga catcagtatc ccacagcctc   9089
tccaagtccc ccggtctcct cctcttctcg aagggaccaa aagatcaatc caccacaccc   9149
gacgacactc aactccccac ccctaaagga gacaccggga atcccagaat caagactcat   9209 cca atg tcc atc atg ggt ctc aag gtg aac gtc tct gcc ata ttc       9254
    Met Ser Ile Met Gly Leu Lys Val Asn Val Ser Ala Ile Phe
        2560                2565                2570 atg gca gta ctg tta act ctc caa aca ccc acc ggt caa atc cat       9299
Met Ala Val Leu Leu Thr Leu Gln Thr Pro Thr Gly Gln Ile His
    2575                2580                2585 tgg ggc aat ctc tct aag ata ggg gtg gta gga ata gga agt gca       9344
Trp Gly Asn Leu Ser Lys Ile Gly Val Val Gly Ile Gly Ser Ala
    2590                2595                2600 agc tac aaa gtt atg act cgt tcc agc cat caa tca tta gtc ata       9389
Ser Tyr Lys Val Met Thr Arg Ser Ser His Gln Ser Leu Val Ile
    2605                2610                2615 aaa tta atg ccc aat ata act ctc ctc aat aac tgc acg agg gta       9434
Lys Leu Met Pro Asn Ile Thr Leu Leu Asn Asn Cys Thr Arg Val
    2620                2625                2630 gag att gca gaa tac agg aga cta ctg aga aca gtt ttg gaa cca       9479
Glu Ile Ala Glu Tyr Arg Arg Leu Leu Arg Thr Val Leu Glu Pro
    2635                2640                2645 att aga gat gca ctt aat gca atg acc cag aat ata aga ccg gtt       9524
Ile Arg Asp Ala Leu Asn Ala Met Thr Gln Asn Ile Arg Pro Val
    2650                2655                2660 cag agt gta gct tca agt agg aga cac aag aga ttt gcg gga gta       9569
Gln Ser Val Ala Ser Ser Arg Arg His Lys Arg Phe Ala Gly Val
    2665                2670                2675 gtc ctg gca ggt gcg gcc cta ggc gtt gcc aca gct gct cag ata       9614
Val Leu Ala Gly Ala Ala Leu Gly Val Ala Thr Ala Ala Gln Ile
    2680                2685                2690 aca gcc ggc att gca ctt cac cag tcc atg ctg aac tct caa gcc       9659
Thr Ala Gly Ile Ala Leu His Gln Ser Met Leu Asn Ser Gln Ala
    2695                2700                2705 atc gac aat ctg aga gcg agc ctg gaa act act aat cag gca att       9704
```

|  |  |  |  |  |  |  |  |  |  |  |  |  |  |  |
|---|---|---|---|---|---|---|---|---|---|---|---|---|---|---|
|  | Ile | Asp | Asn | Leu | Arg | Ala | Ser | Leu | Glu | Thr | Thr | Asn | Gln | Ala | Ile |
|  |  | 2710 |  |  |  | 2715 |  |  |  | 2720 |  |  |  |  |  |

```
gag aca atc aga caa gca ggg cag gag atg ata ttg gct gtt cag         9749
Glu Thr Ile Arg Gln Ala Gly Gln Glu Met Ile Leu Ala Val Gln
            2725                2730                2735 ggt gtc caa gac tac atc aat aat gag ctg ata ccg tct atg aac         9794
Gly Val Gln Asp Tyr Ile Asn Asn Glu Leu Ile Pro Ser Met Asn
        2740                2745                2750 caa cta tct tgt gat tta atc ggc cag aag ctc ggg ctc aaa ttg         9839
Gln Leu Ser Cys Asp Leu Ile Gly Gln Lys Leu Gly Leu Lys Leu
    2755                2760                2765 ctc aga tac tat aca gaa atc ctg tca tta ttt ggc ccc agt tta         9884
Leu Arg Tyr Tyr Thr Glu Ile Leu Ser Leu Phe Gly Pro Ser Leu
2770                2775                2780 cgg gac ccc ata tct gcg gag ata tct atc cag gct ttg agc tat         9929
Arg Asp Pro Ile Ser Ala Glu Ile Ser Ile Gln Ala Leu Ser Tyr
            2785                2790                2795 gcg ctt gga gga gac atc aat aag gtg tta gaa aag ctc gga tac         9974
Ala Leu Gly Gly Asp Ile Asn Lys Val Leu Glu Lys Leu Gly Tyr
        2800                2805                2810 agt gga ggt gat tta ctg ggc atc tta gag agc gga gga ata aag        10019
Ser Gly Gly Asp Leu Leu Gly Ile Leu Glu Ser Gly Gly Ile Lys
    2815                2820                2825 gcc cgg ata act cac gtc gac aca gag tcc tac ttc att gtc ctc        10064
Ala Arg Ile Thr His Val Asp Thr Glu Ser Tyr Phe Ile Val Leu
2830                2835                2840 agt ata gcc tat ccg acg ctg tcc gag att aag ggg gtg att gtc        10109
Ser Ile Ala Tyr Pro Thr Leu Ser Glu Ile Lys Gly Val Ile Val
            2845                2850                2855 cac cgg cta gag ggg gtc tcg tac aac ata ggc tct caa gag tgg        10154
His Arg Leu Glu Gly Val Ser Tyr Asn Ile Gly Ser Gln Glu Trp
        2860                2865                2870 tat acc act gtg ccc aag tat gtt gca acc caa ggg tac ctt atc        10199
Tyr Thr Thr Val Pro Lys Tyr Val Ala Thr Gln Gly Tyr Leu Ile
    2875                2880                2885 tcg aat ttt gat gag tca tcg tgt act ttc atg cca gag ggg act        10244
Ser Asn Phe Asp Glu Ser Ser Cys Thr Phe Met Pro Glu Gly Thr
2890                2895                2900 gtg tgc agc caa aat gcc ttg tac ccg atg agt cct ctg ctc caa        10289
Val Cys Ser Gln Asn Ala Leu Tyr Pro Met Ser Pro Leu Leu Gln
            2905                2910                2915 gaa tgc ctc cgg ggg tac acc aag tcc tgt gct cgt aca ctc gta        10334
Glu Cys Leu Arg Gly Tyr Thr Lys Ser Cys Ala Arg Thr Leu Val
        2920                2925                2930 tcc ggg tct ttt ggg aac cgg ttc att tta tca caa ggg aac cta        10379
Ser Gly Ser Phe Gly Asn Arg Phe Ile Leu Ser Gln Gly Asn Leu
    2935                2940                2945 ata gcc aat tgt gca tca atc ctt tgc aag tgt tac aca aca gga        10424
Ile Ala Asn Cys Ala Ser Ile Leu Cys Lys Cys Tyr Thr Thr Gly
2950                2955                2960 acg atc att aat caa gac cct gac aag atc cta aca tac att gct        10469
Thr Ile Ile Asn Gln Asp Pro Asp Lys Ile Leu Thr Tyr Ile Ala
            2965                2970                2975 gcc gat cac tgc ccg gta gtc gag gtg aac ggc gtg acc atc caa        10514
Ala Asp His Cys Pro Val Val Glu Val Asn Gly Val Thr Ile Gln
        2980                2985                2990 gtc ggg agc agg agg tat cca gac gct gtg tac ttg cac aga att        10559
Val Gly Ser Arg Arg Tyr Pro Asp Ala Val Tyr Leu His Arg Ile
    2995                3000                3005
```

-continued

| | |
|---|---|
| gac ctc ggt cct ccc ata tca ttg gag agg ttg gac gta ggg aca<br>Asp Leu Gly Pro Pro Ile Ser Leu Glu Arg Leu Asp Val Gly Thr<br>          3010               3015               3020 | 10604 |
| aat ctg ggg aat gca att gct aag ttg gag gat gcc aag gaa ttg<br>Asn Leu Gly Asn Ala Ile Ala Lys Leu Glu Asp Ala Lys Glu Leu<br>          3025               3030               3035 | 10649 |
| ttg gag tca tcg gac cag ata ttg agg agt atg aaa ggt tta tcg<br>Leu Glu Ser Ser Asp Gln Ile Leu Arg Ser Met Lys Gly Leu Ser<br>          3040               3045               3050 | 10694 |
| agc act agc ata gtc tac atc ctg att gca gtg tgt ctt gga ggg<br>Ser Thr Ser Ile Val Tyr Ile Leu Ile Ala Val Cys Leu Gly Gly<br>          3055               3060               3065 | 10739 |
| ttg ata ggg atc ccc gct tta ata tgt tgc tgc agg ggg cgt tgt<br>Leu Ile Gly Ile Pro Ala Leu Ile Cys Cys Cys Arg Gly Arg Cys<br>          3070               3075               3080 | 10784 |
| aac aaa aag gga gaa caa gtt ggt atg tca aga cca ggc cta aag<br>Asn Lys Lys Gly Glu Gln Val Gly Met Ser Arg Pro Gly Leu Lys<br>          3085               3090               3095 | 10829 |
| cct gat ctt acg gga aca tca aaa tcc tat gta agg tcg ctc tga<br>Pro Asp Leu Thr Gly Thr Ser Lys Ser Tyr Val Arg Ser Leu<br>          3100               3105               3110 | 10874 |
| tcctctacaa ctcttgaaac acaaatgtcc cacaagtctc ctcttcgtca tcaagcaacc | 10934 |
| accgcaccca gcatcaagcc cacctgaaat tatctccggc ttccctctgg ccgaacaata | 10994 |
| tcggtagtta atcaaaactt agggtgcaag atcatccaca atg tca cca caa cga<br>                                                              Met Ser Pro Gln Arg<br>                                                                                     3115 | 11049 |
| gac cgg ata aat gcc ttc tac aaa gat aac ccc cat ccc aag gga<br>Asp Arg Ile Asn Ala Phe Tyr Lys Asp Asn Pro His Pro Lys Gly<br>          3120               3125               3130 | 11094 |
| agt agg ata gtc att aac aga gaa cat ctt atg att gat aga cct<br>Ser Arg Ile Val Ile Asn Arg Glu His Leu Met Ile Asp Arg Pro<br>          3135               3140               3145 | 11139 |
| tat gtt ttg ctg gct gtt ctg ttt gtc atg ttt ctg agc ttg atc<br>Tyr Val Leu Leu Ala Val Leu Phe Val Met Phe Leu Ser Leu Ile<br>          3150               3155               3160 | 11184 |
| ggg ttg cta gcc att gca ggc att aga ctt cat cgg gca gcc atc<br>Gly Leu Leu Ala Ile Ala Gly Ile Arg Leu His Arg Ala Ala Ile<br>          3165               3170               3175 | 11229 |
| tac acc gca gag atc cat aaa agc ctc agc acc aat cta gat gta<br>Tyr Thr Ala Glu Ile His Lys Ser Leu Ser Thr Asn Leu Asp Val<br>          3180               3185               3190 | 11274 |
| act aac tca atc gag cat cag gtc aag gac gtg ctg aca cca ctc<br>Thr Asn Ser Ile Glu His Gln Val Lys Asp Val Leu Thr Pro Leu<br>          3195               3200               3205 | 11319 |
| ttc aaa atc atc ggt gat gaa gtg ggc ctg agg aca cct cag aga<br>Phe Lys Ile Ile Gly Asp Glu Val Gly Leu Arg Thr Pro Gln Arg<br>          3210               3215               3220 | 11364 |
| ttc act gac cta gtg aaa tta atc tct gac aag att aaa ttc ctt<br>Phe Thr Asp Leu Val Lys Leu Ile Ser Asp Lys Ile Lys Phe Leu<br>          3225               3230               3235 | 11409 |
| aat ccg gat agg gag tac gac ttc aga gat ctc act tgg tgt atc<br>Asn Pro Asp Arg Glu Tyr Asp Phe Arg Asp Leu Thr Trp Cys Ile<br>          3240               3245               3250 | 11454 |
| aac ccg cca gag aga atc aaa ttg gat tat gat caa tac tgt gca<br>Asn Pro Pro Glu Arg Ile Lys Leu Asp Tyr Asp Gln Tyr Cys Ala<br>          3255               3260               3265 | 11499 |
| gat gtg gct gct gaa gag ctc atg aat gca ttg gtg aac tca act<br>Asp Val Ala Ala Glu Glu Leu Met Asn Ala Leu Val Asn Ser Thr<br>          3270               3275               3280 | 11544 |

-continued

| | | | | | | | | | | | | | | |
|---|---|---|---|---|---|---|---|---|---|---|---|---|---|---|
| cta | ctg | gag | acc | aga | aca | acc | aat | cag | ttc | cta | gct | gtc | tca | aag | 11589 |
| Leu | Leu | Glu | Thr | Arg | Thr | Thr | Asn | Gln | Phe | Leu | Ala | Val | Ser | Lys | |
| | | | 3285 | | | | 3290 | | | | | 3295 | | | |
| gga | aac | tgc | tca | ggg | ccc | act | aca | atc | aga | ggt | caa | ttc | tca | aac | 11634 |
| Gly | Asn | Cys | Ser | Gly | Pro | Thr | Thr | Ile | Arg | Gly | Gln | Phe | Ser | Asn | |
| | | | 3300 | | | | 3305 | | | | | 3310 | | | |
| atg | tcg | ctg | tcc | ctg | tta | gac | ttg | tat | tta | ggt | cga | ggt | tac | aat | 11679 |
| Met | Ser | Leu | Ser | Leu | Leu | Asp | Leu | Tyr | Leu | Gly | Arg | Gly | Tyr | Asn | |
| | | | 3315 | | | | 3320 | | | | | 3325 | | | |
| gtg | tca | tct | ata | gtc | act | atg | aca | tcc | cag | gga | atg | tat | ggg | gga | 11724 |
| Val | Ser | Ser | Ile | Val | Thr | Met | Thr | Ser | Gln | Gly | Met | Tyr | Gly | Gly | |
| | | | 3330 | | | | 3335 | | | | | 3340 | | | |
| act | tac | cta | gtg | gaa | aag | cct | aat | ctg | agc | agc | aaa | agg | tca | gag | 11769 |
| Thr | Tyr | Leu | Val | Glu | Lys | Pro | Asn | Leu | Ser | Ser | Lys | Arg | Ser | Glu | |
| | | | 3345 | | | | 3350 | | | | | 3355 | | | |
| ttg | tca | caa | ctg | agc | atg | tac | cga | gtg | ttt | gaa | gta | ggt | gtt | atc | 11814 |
| Leu | Ser | Gln | Leu | Ser | Met | Tyr | Arg | Val | Phe | Glu | Val | Gly | Val | Ile | |
| | | | 3360 | | | | 3365 | | | | | 3370 | | | |
| aga | aat | ccg | ggt | ttg | ggg | gct | ccg | gtg | ttc | cat | atg | aca | aac | tat | 11859 |
| Arg | Asn | Pro | Gly | Leu | Gly | Ala | Pro | Val | Phe | His | Met | Thr | Asn | Tyr | |
| | | | 3375 | | | | 3380 | | | | | 3385 | | | |
| ctt | gag | caa | cca | gtc | agt | aat | gat | ctc | agc | aac | tgt | atg | gtg | gct | 11904 |
| Leu | Glu | Gln | Pro | Val | Ser | Asn | Asp | Leu | Ser | Asn | Cys | Met | Val | Ala | |
| | | | 3390 | | | | 3395 | | | | | 3400 | | | |
| ttg | ggg | gag | ctc | aaa | ctc | gca | gcc | ctt | tgt | cac | ggg | gaa | gat | tct | 11949 |
| Leu | Gly | Glu | Leu | Lys | Leu | Ala | Ala | Leu | Cys | His | Gly | Glu | Asp | Ser | |
| | | | 3405 | | | | 3410 | | | | | 3415 | | | |
| atc | aca | att | ccc | tat | cag | gga | tca | ggg | aaa | ggt | gtc | agc | ttc | cag | 11994 |
| Ile | Thr | Ile | Pro | Tyr | Gln | Gly | Ser | Gly | Lys | Gly | Val | Ser | Phe | Gln | |
| | | | 3420 | | | | 3425 | | | | | 3430 | | | |
| ctc | gtc | aag | cta | ggt | gtc | tgg | aaa | tcc | cca | acc | gac | atg | caa | tcc | 12039 |
| Leu | Val | Lys | Leu | Gly | Val | Trp | Lys | Ser | Pro | Thr | Asp | Met | Gln | Ser | |
| | | | 3435 | | | | 3440 | | | | | 3445 | | | |
| tgg | gtc | ccc | tta | tca | acg | gat | gat | cca | gtg | ata | gac | agg | ctt | tac | 12084 |
| Trp | Val | Pro | Leu | Ser | Thr | Asp | Asp | Pro | Val | Ile | Asp | Arg | Leu | Tyr | |
| | | | 3450 | | | | 3455 | | | | | 3460 | | | |
| ctc | tca | tct | cac | aga | ggt | gtt | atc | gct | gac | aat | caa | gca | aaa | tgg | 12129 |
| Leu | Ser | Ser | His | Arg | Gly | Val | Ile | Ala | Asp | Asn | Gln | Ala | Lys | Trp | |
| | | | 3465 | | | | 3470 | | | | | 3475 | | | |
| gct | gtc | ccg | aca | aca | cga | aca | gat | gac | aag | ttg | cga | atg | gag | aca | 12174 |
| Ala | Val | Pro | Thr | Thr | Arg | Thr | Asp | Asp | Lys | Leu | Arg | Met | Glu | Thr | |
| | | | 3480 | | | | 3485 | | | | | 3490 | | | |
| tgc | ttc | caa | cag | gcg | tgt | aag | ggt | aaa | atc | caa | gca | ctc | tgc | gag | 12219 |
| Cys | Phe | Gln | Gln | Ala | Cys | Lys | Gly | Lys | Ile | Gln | Ala | Leu | Cys | Glu | |
| | | | 3495 | | | | 3500 | | | | | 3505 | | | |
| aat | ccc | gag | tgg | gca | cca | ttg | aag | gat | aac | agg | att | cct | tca | tac | 12264 |
| Asn | Pro | Glu | Trp | Ala | Pro | Leu | Lys | Asp | Asn | Arg | Ile | Pro | Ser | Tyr | |
| | | | 3510 | | | | 3515 | | | | | 3520 | | | |
| ggg | gtc | ttg | tct | gtt | gat | ctg | agt | ctg | aca | gtt | gag | ctt | aaa | atc | 12309 |
| Gly | Val | Leu | Ser | Val | Asp | Leu | Ser | Leu | Thr | Val | Glu | Leu | Lys | Ile | |
| | | | 3525 | | | | 3530 | | | | | 3535 | | | |
| aaa | att | gct | tcg | gga | ttc | ggg | cca | ttg | atc | aca | cac | ggt | tca | ggg | 12354 |
| Lys | Ile | Ala | Ser | Gly | Phe | Gly | Pro | Leu | Ile | Thr | His | Gly | Ser | Gly | |
| | | | 3540 | | | | 3545 | | | | | 3550 | | | |
| atg | gac | cta | tac | aaa | tcc | aac | cac | aac | aat | gtg | tat | tgg | ctg | act | 12399 |
| Met | Asp | Leu | Tyr | Lys | Ser | Asn | His | Asn | Asn | Val | Tyr | Trp | Leu | Thr | |
| | | | 3555 | | | | 3560 | | | | | 3565 | | | |
| atc | ccg | cca | atg | aag | aac | cta | gcc | tta | ggt | gta | atc | aac | aca | ttg | 12444 |
| Ile | Pro | Pro | Met | Lys | Asn | Leu | Ala | Leu | Gly | Val | Ile | Asn | Thr | Leu | |

```
                    3570                3575                3580
gag tgg ata ccg aga ttc aag gtt agt ccc tac ctc ttc act gtc     12489
Glu Trp Ile Pro Arg Phe Lys Val Ser Pro Tyr Leu Phe Thr Val
                3585                3590                3595 cca att aag gaa gca ggc gaa gac tgc cat gcc cca aca tac cta     12534
Pro Ile Lys Glu Ala Gly Glu Asp Cys His Ala Pro Thr Tyr Leu
                3600                3605                3610 cct gcg gag gtg gat ggt gat gtc aaa ctc agt tcc aat ctg gtg     12579
Pro Ala Glu Val Asp Gly Asp Val Lys Leu Ser Ser Asn Leu Val
                3615                3620                3625 att cta cct ggt caa gat ctc caa tat gtt ttg gca acc tac gat     12624
Ile Leu Pro Gly Gln Asp Leu Gln Tyr Val Leu Ala Thr Tyr Asp
                3630                3635                3640 act tcc agg gtt gaa cat gct gtg gtt tat tac gtt tac agc cca     12669
Thr Ser Arg Val Glu His Ala Val Val Tyr Tyr Val Tyr Ser Pro
                3645                3650                3655 agc cgc tca ttt tct tac ttt tat cct ttt agg ttg cct ata aag     12714
Ser Arg Ser Phe Ser Tyr Phe Tyr Pro Phe Arg Leu Pro Ile Lys
                3660                3665                3670 ggg gtc ccc atc gaa tta caa gtg gaa tgc ttc aca tgg gac caa     12759
Gly Val Pro Ile Glu Leu Gln Val Glu Cys Phe Thr Trp Asp Gln
                3675                3680                3685 aaa ctc tgg tgc cgt cac ttc tgt gtg ctt gcg gac tca gaa tct     12804
Lys Leu Trp Cys Arg His Phe Cys Val Leu Ala Asp Ser Glu Ser
                3690                3695                3700 ggt gga cat atc act cac tct ggg atg gtg ggc atg gga gtc agc     12849
Gly Gly His Ile Thr His Ser Gly Met Val Gly Met Gly Val Ser
                3705                3710                3715 tgc aca gtc acc cgg gaa gat gga acc aat cgc aga tag ggctgctagt  12898
Cys Thr Val Thr Arg Glu Asp Gly Thr Asn Arg Arg
                3720                3725 gaaccaatca catgatgtca cccagacatc aggcataccc actagtgtga aatagacatc 12958 agaattaaga aaacgtagg gtccaagtgg ttccccgtt atg gac tcg cta tct     13012
                                          Met Asp Ser Leu Ser
                                                         3730 gtc aac cag atc tta tac cct gaa gtt cac cta gat agc ccg ata     13057
Val Asn Gln Ile Leu Tyr Pro Glu Val His Leu Asp Ser Pro Ile
                3735                3740                3745 gtt acc aat aag ata gta gcc atc ctg gag tat gct cga gtc cct     13102
Val Thr Asn Lys Ile Val Ala Ile Leu Glu Tyr Ala Arg Val Pro
                3750                3755                3760 cac gct tac agc ctg gag gac cct aca ctg tgt cag aac atc aag     13147
His Ala Tyr Ser Leu Glu Asp Pro Thr Leu Cys Gln Asn Ile Lys
                3765                3770                3775 cac cgc cta aaa aac gga ttt tcc aac caa atg att ata aac aat     13192
His Arg Leu Lys Asn Gly Phe Ser Asn Gln Met Ile Ile Asn Asn
                3780                3785                3790 gtg gaa gtt ggg aat gtc atc aag tcc aag ctt agg agt tat ccg     13237
Val Glu Val Gly Asn Val Ile Lys Ser Lys Leu Arg Ser Tyr Pro
                3795                3800                3805 gcc cac tct cat att cca tat cca aat tgt aat cag gat tta ttt     13282
Ala His Ser His Ile Pro Tyr Pro Asn Cys Asn Gln Asp Leu Phe
                3810                3815                3820 aac ata gaa gac aaa gag tca acg agg aag atc cgt gaa ctc ctc     13327
Asn Ile Glu Asp Lys Glu Ser Thr Arg Lys Ile Arg Glu Leu Leu
                3825                3830                3835 aaa aag ggg aat tcg ctg tac tcc aaa gtc agt gat aag gtt ttc     13372
Lys Lys Gly Asn Ser Leu Tyr Ser Lys Val Ser Asp Lys Val Phe
                3840                3845                3850
```

| | | | | | | | | | | | | | | |
|---|---|---|---|---|---|---|---|---|---|---|---|---|---|---|
| caa | tgc | tta | agg | gac | act | aac | tca | cgg | ctt | ggc | cta | ggc | tcc | gaa | 13417 |
| Gln | Cys | Leu | Arg | Asp | Thr | Asn | Ser | Arg | Leu | Gly | Leu | Gly | Ser | Glu | |
| | | 3855 | | | | 3860 | | | | 3865 | | | | | |
| ttg | agg | gag | gac | atc | aag | gag | aaa | gtt | att | aac | ttg | gga | gtt | tac | 13462 |
| Leu | Arg | Glu | Asp | Ile | Lys | Glu | Lys | Val | Ile | Asn | Leu | Gly | Val | Tyr | |
| | | 3870 | | | | 3875 | | | | 3880 | | | | | |
| atg | cac | agc | tcc | cag | tgg | ttt | gag | ccc | ttt | ctg | ttt | tgg | ttt | aca | 13507 |
| Met | His | Ser | Ser | Gln | Trp | Phe | Glu | Pro | Phe | Leu | Phe | Trp | Phe | Thr | |
| | | 3885 | | | | 3890 | | | | 3895 | | | | | |
| gtc | aag | act | gag | atg | agg | tca | gtg | att | aaa | tca | caa | acc | cat | act | 13552 |
| Val | Lys | Thr | Glu | Met | Arg | Ser | Val | Ile | Lys | Ser | Gln | Thr | His | Thr | |
| | | 3900 | | | | 3905 | | | | 3910 | | | | | |
| tgc | cat | agg | agg | aga | cac | aca | cct | gta | ttc | ttc | act | ggt | agt | tca | 13597 |
| Cys | His | Arg | Arg | Arg | His | Thr | Pro | Val | Phe | Phe | Thr | Gly | Ser | Ser | |
| | | 3915 | | | | 3920 | | | | 3925 | | | | | |
| gtt | gag | ttg | cta | atc | tct | cgt | gac | ctt | gtt | gct | ata | atc | agt | aaa | 13642 |
| Val | Glu | Leu | Leu | Ile | Ser | Arg | Asp | Leu | Val | Ala | Ile | Ile | Ser | Lys | |
| | | 3930 | | | | 3935 | | | | 3940 | | | | | |
| gag | tct | caa | cat | gta | tat | tac | ctg | aca | ttt | gaa | ctg | gtt | ttg | atg | 13687 |
| Glu | Ser | Gln | His | Val | Tyr | Tyr | Leu | Thr | Phe | Glu | Leu | Val | Leu | Met | |
| | | 3945 | | | | 3950 | | | | 3955 | | | | | |
| tat | tgt | gat | gtc | ata | gag | ggg | agg | tta | atg | aca | gag | acc | gct | atg | 13732 |
| Tyr | Cys | Asp | Val | Ile | Glu | Gly | Arg | Leu | Met | Thr | Glu | Thr | Ala | Met | |
| | | 3960 | | | | 3965 | | | | 3970 | | | | | |
| act | att | gat | gct | agg | tat | aca | gag | ctt | cta | gga | aga | gtc | aga | tac | 13777 |
| Thr | Ile | Asp | Ala | Arg | Tyr | Thr | Glu | Leu | Leu | Gly | Arg | Val | Arg | Tyr | |
| | | 3975 | | | | 3980 | | | | 3985 | | | | | |
| atg | tgg | aaa | ctg | ata | gat | ggt | ttc | ttc | cct | gca | ctc | ggg | aat | cca | 13822 |
| Met | Trp | Lys | Leu | Ile | Asp | Gly | Phe | Phe | Pro | Ala | Leu | Gly | Asn | Pro | |
| | | 3990 | | | | 3995 | | | | 4000 | | | | | |
| act | tat | caa | att | gta | gcc | atg | ctg | gag | cct | ctt | tca | ctt | gct | tac | 13867 |
| Thr | Tyr | Gln | Ile | Val | Ala | Met | Leu | Glu | Pro | Leu | Ser | Leu | Ala | Tyr | |
| | | 4005 | | | | 4010 | | | | 4015 | | | | | |
| ctg | cag | ctg | agg | gat | ata | aca | gta | gaa | ctc | aga | ggt | gct | ttc | ctt | 13912 |
| Leu | Gln | Leu | Arg | Asp | Ile | Thr | Val | Glu | Leu | Arg | Gly | Ala | Phe | Leu | |
| | | 4020 | | | | 4025 | | | | 4030 | | | | | |
| aac | cac | tgc | ttt | act | gaa | ata | cat | gat | gtt | ctt | gac | caa | aac | ggg | 13957 |
| Asn | His | Cys | Phe | Thr | Glu | Ile | His | Asp | Val | Leu | Asp | Gln | Asn | Gly | |
| | | 4035 | | | | 4040 | | | | 4045 | | | | | |
| ttt | tct | gat | gaa | ggt | act | tat | cat | gag | tta | act | gaa | gct | cta | gat | 14002 |
| Phe | Ser | Asp | Glu | Gly | Thr | Tyr | His | Glu | Leu | Thr | Glu | Ala | Leu | Asp | |
| | | 4050 | | | | 4055 | | | | 4060 | | | | | |
| tac | att | ttc | ata | act | gat | gac | ata | cat | ctg | aca | ggg | gag | att | ttc | 14047 |
| Tyr | Ile | Phe | Ile | Thr | Asp | Asp | Ile | His | Leu | Thr | Gly | Glu | Ile | Phe | |
| | | 4065 | | | | 4070 | | | | 4075 | | | | | |
| tca | ttt | ttc | aga | agt | ttc | ggc | cac | ccc | aga | ctt | gaa | gca | gta | acg | 14092 |
| Ser | Phe | Phe | Arg | Ser | Phe | Gly | His | Pro | Arg | Leu | Glu | Ala | Val | Thr | |
| | | 4080 | | | | 4085 | | | | 4090 | | | | | |
| gct | gct | gaa | aat | gtt | agg | aaa | tac | atg | aat | cag | cct | aaa | gtc | att | 14137 |
| Ala | Ala | Glu | Asn | Val | Arg | Lys | Tyr | Met | Asn | Gln | Pro | Lys | Val | Ile | |
| | | 4095 | | | | 4100 | | | | 4105 | | | | | |
| gtg | tat | gag | act | ctg | atg | aaa | ggt | cat | gcc | ata | ttt | tgt | gga | atc | 14182 |
| Val | Tyr | Glu | Thr | Leu | Met | Lys | Gly | His | Ala | Ile | Phe | Cys | Gly | Ile | |
| | | 4110 | | | | 4115 | | | | 4120 | | | | | |
| ata | atc | aac | ggc | tat | cgt | gac | agg | cac | gga | ggc | agt | tgg | cca | ccg | 14227 |
| Ile | Ile | Asn | Gly | Tyr | Arg | Asp | Arg | His | Gly | Gly | Ser | Trp | Pro | Pro | |
| | | 4125 | | | | 4130 | | | | 4135 | | | | | |
| ctg | acc | ctc | ccc | ctg | cat | gct | gca | gac | aca | atc | cgg | aat | gct | caa | 14272 |
| Leu | Thr | Leu | Pro | Leu | His | Ala | Ala | Asp | Thr | Ile | Arg | Asn | Ala | Gln | |

-continued

```
            4140                4145                4150
gct tca ggt gaa ggg tta aca cat gag cag tgc gtt gat aac tgg     14317
Ala Ser Gly Glu Gly Leu Thr His Glu Gln Cys Val Asp Asn Trp
            4155                4160                4165 aaa tct ttt gct gga gtg aaa ttt ggc tgc ttt atg cct ctt agc     14362
Lys Ser Phe Ala Gly Val Lys Phe Gly Cys Phe Met Pro Leu Ser
            4170                4175                4180 ctg gat agt gat ctg aca atg tac cta aag gac aag gca ctt gct     14407
Leu Asp Ser Asp Leu Thr Met Tyr Leu Lys Asp Lys Ala Leu Ala
            4185                4190                4195 gct ctc caa agg gaa tgg gat tca gtt tac ccg aaa gag ttc ctg     14452
Ala Leu Gln Arg Glu Trp Asp Ser Val Tyr Pro Lys Glu Phe Leu
            4200                4205                4210 cgt tac gac cct ccc aag gga acc ggg tca cgg agg ctt gta gat     14497
Arg Tyr Asp Pro Pro Lys Gly Thr Gly Ser Arg Arg Leu Val Asp
            4215                4220                4225 gtt ttc ctt aat gat tcg agc ttt gac cca tat gat gtg ata atg     14542
Val Phe Leu Asn Asp Ser Ser Phe Asp Pro Tyr Asp Val Ile Met
            4230                4235                4240 tat gtt gta agt gga gct tac ctc cat gac cct gag ttc aac ctg     14587
Tyr Val Val Ser Gly Ala Tyr Leu His Asp Pro Glu Phe Asn Leu
            4245                4250                4255 tct tac agc ctg aaa gaa aag gag atc aag gaa aca ggt aga ctt     14632
Ser Tyr Ser Leu Lys Glu Lys Glu Ile Lys Glu Thr Gly Arg Leu
            4260                4265                4270 ttt gct aaa atg act tac aaa atg agg gca tgc caa gtg att gct     14677
Phe Ala Lys Met Thr Tyr Lys Met Arg Ala Cys Gln Val Ile Ala
            4275                4280                4285 gaa aat cta atc tca aac ggg att ggc aaa tat ttt aag gac aat     14722
Glu Asn Leu Ile Ser Asn Gly Ile Gly Lys Tyr Phe Lys Asp Asn
            4290                4295                4300 ggg atg gcc aag gat gag cac gat ttg act aag gca ctc cac act     14767
Gly Met Ala Lys Asp Glu His Asp Leu Thr Lys Ala Leu His Thr
            4305                4310                4315 cta gct gtc tca gga gtc ccc aaa gat ctc aaa gaa agt cac agg     14812
Leu Ala Val Ser Gly Val Pro Lys Asp Leu Lys Glu Ser His Arg
            4320                4325                4330 ggg ggg cca gtc tta aaa acc tac tcc cga agc cca gtc cac aca     14857
Gly Gly Pro Val Leu Lys Thr Tyr Ser Arg Ser Pro Val His Thr
            4335                4340                4345 agt acc agg aac gtg aga gca gca aaa ggg ttt ata ggg ttc cct     14902
Ser Thr Arg Asn Val Arg Ala Ala Lys Gly Phe Ile Gly Phe Pro
            4350                4355                4360 caa gta att cgg cag gac caa gac act gat cat ccg gag aat atg     14947
Gln Val Ile Arg Gln Asp Gln Asp Thr Asp His Pro Glu Asn Met
            4365                4370                4375 gaa gct tac gag aca gtc agt gca ttt atc acg act gat ctc aag     14992
Glu Ala Tyr Glu Thr Val Ser Ala Phe Ile Thr Thr Asp Leu Lys
            4380                4385                4390 aag tac tgc ctt aat tgg aga tat gag acc atc agc ttg ttt gca     15037
Lys Tyr Cys Leu Asn Trp Arg Tyr Glu Thr Ile Ser Leu Phe Ala
            4395                4400                4405 cag agg cta aat gag att tac gga ttg ccc tca ttt ttc cag tgg     15082
Gln Arg Leu Asn Glu Ile Tyr Gly Leu Pro Ser Phe Phe Gln Trp
            4410                4415                4420 ctg cat aag agg ctt gag acc tct gtc ctg tat gta agt gac cct     15127
Leu His Lys Arg Leu Glu Thr Ser Val Leu Tyr Val Ser Asp Pro
            4425                4430                4435 cat tgc ccc ccc gac ctt gac gcc cat atc ccg tta tat aaa gtc     15172
```

```
His Cys Pro Pro Asp Leu Asp Ala His Ile Pro Leu Tyr Lys Val
        4440                4445                4450 ccc aat gat caa atc ttc att aag tac cct atg gga ggt ata gaa        15217
Pro Asn Asp Gln Ile Phe Ile Lys Tyr Pro Met Gly Gly Ile Glu
        4455                4460                4465 ggg tat tgt cag aag ctg tgg acc atc agc acc att ccc tat cta        15262
Gly Tyr Cys Gln Lys Leu Trp Thr Ile Ser Thr Ile Pro Tyr Leu
        4470                4475                4480 tac ctg gct gct tat gag agc gga gta agg att gct tcg tta gtg        15307
Tyr Leu Ala Ala Tyr Glu Ser Gly Val Arg Ile Ala Ser Leu Val
        4485                4490                4495 caa ggg gac aat cag acc ata gcc gta aca aaa agg gta ccc agc        15352
Gln Gly Asp Asn Gln Thr Ile Ala Val Thr Lys Arg Val Pro Ser
        4500                4505                4510 aca tgg ccc tac aac ctt aag aaa cgg gaa gct gct aga gta act        15397
Thr Trp Pro Tyr Asn Leu Lys Lys Arg Glu Ala Ala Arg Val Thr
        4515                4520                4525 aga gat tac ttt gta att ctt agg caa agg cta cat gat att ggc        15442
Arg Asp Tyr Phe Val Ile Leu Arg Gln Arg Leu His Asp Ile Gly
        4530                4535                4540 cat cac ctc aag gca aat gag aca att gtt tca tca cat ttt ttt        15487
His His Leu Lys Ala Asn Glu Thr Ile Val Ser Ser His Phe Phe
        4545                4550                4555 gtc tat tca aaa gga ata tat tat gat ggg cta ctt gtg tcc caa        15532
Val Tyr Ser Lys Gly Ile Tyr Tyr Asp Gly Leu Leu Val Ser Gln
        4560                4565                4570 tca ctc aag agc atc gca aga tgt gta ttc tgg tca gag act ata        15577
Ser Leu Lys Ser Ile Ala Arg Cys Val Phe Trp Ser Glu Thr Ile
        4575                4580                4585 gtt gat gaa aca agg gca gca tgc agt aat att gct aca aca atg        15622
Val Asp Glu Thr Arg Ala Ala Cys Ser Asn Ile Ala Thr Thr Met
        4590                4595                4600 gct aaa agc atc gag aga ggt tat gac cgt tac ctt gca tat tcc        15667
Ala Lys Ser Ile Glu Arg Gly Tyr Asp Arg Tyr Leu Ala Tyr Ser
        4605                4610                4615 ctg aac gtc cta aaa gtg ata cag caa att ctg atc tct ctt ggc        15712
Leu Asn Val Leu Lys Val Ile Gln Gln Ile Leu Ile Ser Leu Gly
        4620                4625                4630 ttc aca atc aat tca acc atg acc cgg gat gta gtc atc ccc ctc        15757
Phe Thr Ile Asn Ser Thr Met Thr Arg Asp Val Val Ile Pro Leu
        4635                4640                4645 ctc aca aac aac gac ctc tta ata agg atg gca ctg ttg ccc gct        15802
Leu Thr Asn Asn Asp Leu Leu Ile Arg Met Ala Leu Leu Pro Ala
        4650                4655                4660 cct att ggg ggg atg aat tat ctg aat atg agc agg ctg ttt gtc        15847
Pro Ile Gly Gly Met Asn Tyr Leu Asn Met Ser Arg Leu Phe Val
        4665                4670                4675 aga aac atc ggt gat cca gta aca tca tca att gct gat ctc aag        15892
Arg Asn Ile Gly Asp Pro Val Thr Ser Ser Ile Ala Asp Leu Lys
        4680                4685                4690 aga atg att ctc gcc tca cta atg cct gaa gag acc ctc cat caa        15937
Arg Met Ile Leu Ala Ser Leu Met Pro Glu Glu Thr Leu His Gln
        4695                4700                4705 gta atg aca caa caa ccg ggg gac tct tca ttc cta gac tgg gct        15982
Val Met Thr Gln Gln Pro Gly Asp Ser Ser Phe Leu Asp Trp Ala
        4710                4715                4720 agc gac cct tac tca gca aat ctt gta tgt gtc cag agc atc act        16027
Ser Asp Pro Tyr Ser Ala Asn Leu Val Cys Val Gln Ser Ile Thr
        4725                4730                4735
```

```
aga ctc ctc aag aac ata act gca agg ttt gtc ctg atc cat agt    16072
Arg Leu Leu Lys Asn Ile Thr Ala Arg Phe Val Leu Ile His Ser
    4740            4745                4750 cca aac cca atg tta aaa gga tta ttc cat gat gac agt aaa gaa    16117
Pro Asn Pro Met Leu Lys Gly Leu Phe His Asp Asp Ser Lys Glu
    4755            4760                4765 gag gac gag gga ctg gcg gca ttc ctc atg gac agg cat att ata    16162
Glu Asp Glu Gly Leu Ala Ala Phe Leu Met Asp Arg His Ile Ile
    4770            4775                4780 gta cct agg gca gct cat gaa atc ctg gat cat agt gtc aca ggg    16207
Val Pro Arg Ala Ala His Glu Ile Leu Asp His Ser Val Thr Gly
    4785            4790                4795 gca aga gag tct att gca ggc atg ctg gat acc aca aaa ggc ttg    16252
Ala Arg Glu Ser Ile Ala Gly Met Leu Asp Thr Thr Lys Gly Leu
    4800            4805                4810 att cga gcc agc atg agg aag ggg gga tta acc tct cga gtg ata    16297
Ile Arg Ala Ser Met Arg Lys Gly Gly Leu Thr Ser Arg Val Ile
    4815            4820                4825 acc aga ttg tcc aat tat gac tat gaa caa ttc aga gca ggg atg    16342
Thr Arg Leu Ser Asn Tyr Asp Tyr Glu Gln Phe Arg Ala Gly Met
    4830            4835                4840 gtg cta ttg aca gga aga aag aga aat gtc ctc att gac aaa gag    16387
Val Leu Leu Thr Gly Arg Lys Arg Asn Val Leu Ile Asp Lys Glu
    4845            4850                4855 tca tgt tca gtg cag ctg gcg aga gct cta aga agc cat atg tgg    16432
Ser Cys Ser Val Gln Leu Ala Arg Ala Leu Arg Ser His Met Trp
    4860            4865                4870 gcg agg cta gct cga gga cgg cct att tac ggc ctt gag gtc cct    16477
Ala Arg Leu Ala Arg Gly Arg Pro Ile Tyr Gly Leu Glu Val Pro
    4875            4880                4885 gat gta cta gaa tct atg cga ggc cac ctt att cgg cgt cat gag    16522
Asp Val Leu Glu Ser Met Arg Gly His Leu Ile Arg Arg His Glu
    4890            4895                4900 aca tgt gtc atc tgc gag tgt gga tca gtc aac tac gga tgg ttt    16567
Thr Cys Val Ile Cys Glu Cys Gly Ser Val Asn Tyr Gly Trp Phe
    4905            4910                4915 ttt gtc ccc tcg ggt tgc caa ctg gat gat att gac aag gaa aca    16612
Phe Val Pro Ser Gly Cys Gln Leu Asp Asp Ile Asp Lys Glu Thr
    4920            4925                4930 tca tcc ttg aga gtc cca tat att ggt tct acc act gat gag aga    16657
Ser Ser Leu Arg Val Pro Tyr Ile Gly Ser Thr Thr Asp Glu Arg
    4935            4940                4945 aca gac atg aag ctt gcc ttc gta aga gcc cca agt cga tcc ttg    16702
Thr Asp Met Lys Leu Ala Phe Val Arg Ala Pro Ser Arg Ser Leu
    4950            4955                4960 cga tct gct gtt aga ata gca aca gtg tac tca tgg gct tac ggt    16747
Arg Ser Ala Val Arg Ile Ala Thr Val Tyr Ser Trp Ala Tyr Gly
    4965            4970                4975 gat gat gat agc tct tgg aac gaa gcc tgg ttg ttg gct agg caa    16792
Asp Asp Asp Ser Ser Trp Asn Glu Ala Trp Leu Leu Ala Arg Gln
    4980            4985                4990 agg gcc aat gtg agc ctg gag gag cta agg gtg atc act ccc atc    16837
Arg Ala Asn Val Ser Leu Glu Glu Leu Arg Val Ile Thr Pro Ile
    4995            5000                5005 tca act tcg act aat tta gcg cat agg ttg agg gat cgt agc act    16882
Ser Thr Ser Thr Asn Leu Ala His Arg Leu Arg Asp Arg Ser Thr
    5010            5015                5020 caa gtg aaa tac tca ggt aca tcc ctt gtc cga gtg gcg agg tat    16927
Gln Val Lys Tyr Ser Gly Thr Ser Leu Val Arg Val Ala Arg Tyr
    5025            5030                5035
```

| | | | | | | | | | | | | |
|---|---|---|---|---|---|---|---|---|---|---|---|---|
| acc | aca | atc | tcc | aac | gac | aat | ctc | tca | ttt | gtc | ata | tca | gat | aag | 16972 |
| Thr | Thr | Ile | Ser | Asn | Asp | Asn | Leu | Ser | Phe | Val | Ile | Ser | Asp | Lys | |
| | | 5040 | | | | | 5045 | | | | | 5050 | | | |

```
acc aca atc tcc aac gac aat ctc tca ttt gtc ata tca gat aag       16972
Thr Thr Ile Ser Asn Asp Asn Leu Ser Phe Val Ile Ser Asp Lys
        5040                5045                5050 aag gtt gat act aac ttt ata tac caa caa gga atg ctt cta ggg       17017
Lys Val Asp Thr Asn Phe Ile Tyr Gln Gln Gly Met Leu Leu Gly
        5055                5060                5065 ttg ggt gtt tta gaa aca ttg ttt cga ctc gag aaa gat acc gga       17062
Leu Gly Val Leu Glu Thr Leu Phe Arg Leu Glu Lys Asp Thr Gly
        5070                5075                5080 tca tct aac acg gta tta cat ctt cac gtc gaa aca gat tgt tgc       17107
Ser Ser Asn Thr Val Leu His Leu His Val Glu Thr Asp Cys Cys
        5085                5090                5095 gtg atc ccg atg ata gat cat ccc agg ata ccc agc tcc cgc aag       17152
Val Ile Pro Met Ile Asp His Pro Arg Ile Pro Ser Ser Arg Lys
        5100                5105                5110 cta gag ctg agg gca gag cta tgt acc aac cca ttg ata tat gat       17197
Leu Glu Leu Arg Ala Glu Leu Cys Thr Asn Pro Leu Ile Tyr Asp
        5115                5120                5125 aat gca cct tta att gac aga gat gca aca agg cta tac acc cag       17242
Asn Ala Pro Leu Ile Asp Arg Asp Ala Thr Arg Leu Tyr Thr Gln
        5130                5135                5140 agc cat agg agg cac ctt gtg gaa ttt gtt aca tgg tcc aca ccc       17287
Ser His Arg Arg His Leu Val Glu Phe Val Thr Trp Ser Thr Pro
        5145                5150                5155 caa cta tat cac att tta gct aag tcc aca gca cta tct atg att       17332
Gln Leu Tyr His Ile Leu Ala Lys Ser Thr Ala Leu Ser Met Ile
        5160                5165                5170 gac ctg gta aca aaa ttt gag aag gac cat atg aat gaa att tca       17377
Asp Leu Val Thr Lys Phe Glu Lys Asp His Met Asn Glu Ile Ser
        5175                5180                5185 gct ctc ata ggg gat gac gat atc aat agt ttc ata act gag ttt       17422
Ala Leu Ile Gly Asp Asp Asp Ile Asn Ser Phe Ile Thr Glu Phe
        5190                5195                5200 ctg ctc ata gag cca aga tta ttc act atc tac ttg ggc cag tgt       17467
Leu Leu Ile Glu Pro Arg Leu Phe Thr Ile Tyr Leu Gly Gln Cys
        5205                5210                5215 gcg gcc atc aat tgg gca ttt gat gta cat tat cat aga cca tca       17512
Ala Ala Ile Asn Trp Ala Phe Asp Val His Tyr His Arg Pro Ser
        5220                5225                5230 ggg aaa tat cag atg ggt gag ctg ttg tca tcg ttc ctt tct aga       17557
Gly Lys Tyr Gln Met Gly Glu Leu Leu Ser Ser Phe Leu Ser Arg
        5235                5240                5245 atg agc aaa gga gtg ttt aag gtg ctt gtc aat gct cta agc cac       17602
Met Ser Lys Gly Val Phe Lys Val Leu Val Asn Ala Leu Ser His
        5250                5255                5260 cca aag atc tac aag aaa ttc tgg cat tgt ggt att ata gag cct       17647
Pro Lys Ile Tyr Lys Lys Phe Trp His Cys Gly Ile Ile Glu Pro
        5265                5270                5275 atc cat ggt cct tca ctt gat gct caa aac ttg cac aca act gtg       17692
Ile His Gly Pro Ser Leu Asp Ala Gln Asn Leu His Thr Thr Val
        5280                5285                5290 tgc aac atg gtt tac aca tgc tat atg acc tac ctc gac ctg ttg       17737
Cys Asn Met Val Tyr Thr Cys Tyr Met Thr Tyr Leu Asp Leu Leu
        5295                5300                5305 ttg aat gaa gag tta gaa gag ttc aca ttt ctc ttg tgt gaa agc       17782
Leu Asn Glu Glu Leu Glu Glu Phe Thr Phe Leu Leu Cys Glu Ser
        5310                5315                5320 gac gag gat gta gta ccg gac aga ttc gac aac atc cag gca aaa       17827
Asp Glu Asp Val Val Pro Asp Arg Phe Asp Asn Ile Gln Ala Lys
```

-continued

```
              5325                5330                5335 cac tta tgt gtt ctg gca gat ttg tac tgt caa cca ggg acc tgc      17872
His Leu Cys Val Leu Ala Asp Leu Tyr Cys Gln Pro Gly Thr Cys
        5340                5345                5350 cca cca att cga ggt cta aga ccg gta gag aaa tgt gca gtt cta      17917
Pro Pro Ile Arg Gly Leu Arg Pro Val Glu Lys Cys Ala Val Leu
        5355                5360                5365 acc gac cat atc aag gca gag gct atg tta tct cca gca gga tct      17962
Thr Asp His Ile Lys Ala Glu Ala Met Leu Ser Pro Ala Gly Ser
        5370                5375                5380 tcg tgg aac ata aat cca att att gta gac cat tac tca tgc tct      18007
Ser Trp Asn Ile Asn Pro Ile Ile Val Asp His Tyr Ser Cys Ser
        5385                5390                5395 ctg act tat ctc cgg cga gga tcg atc aaa cag ata aga ttg aga      18052
Leu Thr Tyr Leu Arg Arg Gly Ser Ile Lys Gln Ile Arg Leu Arg
        5400                5405                5410 gtt gat cca gga ttc att ttc gac gcc ctc gct gag gta aat gtc      18097
Val Asp Pro Gly Phe Ile Phe Asp Ala Leu Ala Glu Val Asn Val
        5415                5420                5425 agt cag cca aag atc ggc agc aac aac atc tca aat atg agc atc      18142
Ser Gln Pro Lys Ile Gly Ser Asn Asn Ile Ser Asn Met Ser Ile
        5430                5435                5440 aag gct ttc aga ccc cca cac gat gat gtt gca aaa ttg ctc aaa      18187
Lys Ala Phe Arg Pro Pro His Asp Asp Val Ala Lys Leu Leu Lys
        5445                5450                5455 gat atc aac aca agc aag cac aat ctt ccc att tca ggg ggc aat      18232
Asp Ile Asn Thr Ser Lys His Asn Leu Pro Ile Ser Gly Gly Asn
        5460                5465                5470 ctc gcc aat tat gaa atc cat gct ttc cgc aga atc ggg ttg aac      18277
Leu Ala Asn Tyr Glu Ile His Ala Phe Arg Arg Ile Gly Leu Asn
        5475                5480                5485 tca tct gct tgc tac aaa gct gtt gag ata tca aca tta att agg      18322
Ser Ser Ala Cys Tyr Lys Ala Val Glu Ile Ser Thr Leu Ile Arg
        5490                5495                5500 aga tgc ctt gag cca ggg gag gac ggc ttg ttc ttg ggt gag gga      18367
Arg Cys Leu Glu Pro Gly Glu Asp Gly Leu Phe Leu Gly Glu Gly
        5505                5510                5515 tcg ggt tct atg ttg atc act tat aaa gag ata ctt aaa cta aac      18412
Ser Gly Ser Met Leu Ile Thr Tyr Lys Glu Ile Leu Lys Leu Asn
        5520                5525                5530 aag tgc ttc tat aat agt ggg gtt tcc gcc aat tct aga tct ggt      18457
Lys Cys Phe Tyr Asn Ser Gly Val Ser Ala Asn Ser Arg Ser Gly
        5535                5540                5545 caa agg gaa tta gca ccc tat ccc tcc gaa gtt ggc ctt gtc gaa      18502
Gln Arg Glu Leu Ala Pro Tyr Pro Ser Glu Val Gly Leu Val Glu
        5550                5555                5560 cac aga atg gga gta ggt aat att gtc aaa gtg ctc ttt aac ggg      18547
His Arg Met Gly Val Gly Asn Ile Val Lys Val Leu Phe Asn Gly
        5565                5570                5575 agg ccc gaa gtc acg tgg gta ggc agt gta gat tgc ttc aat ttc      18592
Arg Pro Glu Val Thr Trp Val Gly Ser Val Asp Cys Phe Asn Phe
        5580                5585                5590 ata gtt agt aat atc cct acc tct agt gtg ggg ttt atc cat tca      18637
Ile Val Ser Asn Ile Pro Thr Ser Ser Val Gly Phe Ile His Ser
        5595                5600                5605 gat ata gag acc ttg cct gac aaa gat act ata gag aag cta gag      18682
Asp Ile Glu Thr Leu Pro Asp Lys Asp Thr Ile Glu Lys Leu Glu
        5610                5615                5620 gaa ttg gca gcc atc tta tcg atg gct ctg ctc ctg ggc aaa ata      18727
```

|  |  |
|---|---|
| Glu Leu Ala Ala Ile Leu Ser Met Ala Leu Leu Leu Gly Lys Ile<br>     5625                    5630                    5635 |  |
| gga tca ata ctg gtg att aag ctt atg cct ttc agc ggg gat ttt<br>Gly Ser Ile Leu Val Ile Lys Leu Met Pro Phe Ser Gly Asp Phe<br>     5640                    5645                    5650 | 18772 |
| gtt cag gga ttt ata agt tat gta ggg tct cat tat aga gaa gtg<br>Val Gln Gly Phe Ile Ser Tyr Val Gly Ser His Tyr Arg Glu Val<br>     5655                    5660                    5665 | 18817 |
| aac ctt gta tac cct aga tac agc aac ttc atc tct act gaa tct<br>Asn Leu Val Tyr Pro Arg Tyr Ser Asn Phe Ile Ser Thr Glu Ser<br>     5670                    5675                    5680 | 18862 |
| tat ttg gtt atg aca gat ctc aag gct aac cgg cta atg aat cct<br>Tyr Leu Val Met Thr Asp Leu Lys Ala Asn Arg Leu Met Asn Pro<br>     5685                    5690                    5695 | 18907 |
| gaa aag att aag cag cag ata att gaa tca tct gtg agg act tca<br>Glu Lys Ile Lys Gln Gln Ile Ile Glu Ser Ser Val Arg Thr Ser<br>     5700                    5705                    5710 | 18952 |
| cct gga ctt ata ggt cac atc cta tcc att aag caa cta agc tgc<br>Pro Gly Leu Ile Gly His Ile Leu Ser Ile Lys Gln Leu Ser Cys<br>     5715                    5720                    5725 | 18997 |
| ata caa gca att gtg gga gac gca gtt agt aga ggt gat atc aat<br>Ile Gln Ala Ile Val Gly Asp Ala Val Ser Arg Gly Asp Ile Asn<br>     5730                    5735                    5740 | 19042 |
| cct act ctg aaa aaa ctt aca cct ata gag cag gtg ctg atc aat<br>Pro Thr Leu Lys Lys Leu Thr Pro Ile Glu Gln Val Leu Ile Asn<br>     5745                    5750                    5755 | 19087 |
| tgc ggg ttg gca att aac gga cct aag ctg tgc aaa gaa ttg atc<br>Cys Gly Leu Ala Ile Asn Gly Pro Lys Leu Cys Lys Glu Leu Ile<br>     5760                    5765                    5770 | 19132 |
| cac cat gat gtt gcc tca ggg caa gat gga ttg ctt aat tct ata<br>His His Asp Val Ala Ser Gly Gln Asp Gly Leu Leu Asn Ser Ile<br>     5775                    5780                    5785 | 19177 |
| ctc atc ctc tac agg gag ttg gca aga ttc aaa gac aac caa aga<br>Leu Ile Leu Tyr Arg Glu Leu Ala Arg Phe Lys Asp Asn Gln Arg<br>     5790                    5795                    5800 | 19222 |
| agt caa caa ggg atg ttc cac gct tac ccc gta ttg gta agt agc<br>Ser Gln Gln Gly Met Phe His Ala Tyr Pro Val Leu Val Ser Ser<br>     5805                    5810                    5815 | 19267 |
| agg caa cga gaa ctt ata tct agg atc acc cgc aaa ttc tgg ggg<br>Arg Gln Arg Glu Leu Ile Ser Arg Ile Thr Arg Lys Phe Trp Gly<br>     5820                    5825                    5830 | 19312 |
| cac att ctt ctt tac tcc ggg aac aaa aag ttg ata aat aag ttt<br>His Ile Leu Leu Tyr Ser Gly Asn Lys Lys Leu Ile Asn Lys Phe<br>     5835                    5840                    5845 | 19357 |
| atc cag aat ctc aag tcc ggc tat ctg ata cta gac tta cac cag<br>Ile Gln Asn Leu Lys Ser Gly Tyr Leu Ile Leu Asp Leu His Gln<br>     5850                    5855                    5860 | 19402 |
| aat atc ttc gtt aag aat cta tcc aag tca gag aaa cag att att<br>Asn Ile Phe Val Lys Asn Leu Ser Lys Ser Glu Lys Gln Ile Ile<br>     5865                    5870                    5875 | 19447 |
| atg acg ggg ggt ttg aaa cgt gag tgg gtt ttt aag gta aca gtc<br>Met Thr Gly Gly Leu Lys Arg Glu Trp Val Phe Lys Val Thr Val<br>     5880                    5885                    5890 | 19492 |
| aag gag acc aaa gaa tgg tat aag tta gtc gga tac agt gcc ctg<br>Lys Glu Thr Lys Glu Trp Tyr Lys Leu Val Gly Tyr Ser Ala Leu<br>     5895                    5900                    5905 | 19537 |
| att aag gac taa ttggttgaac tccggaaccc taatcctgcc ctaggtggtt<br>Ile Lys Asp<br>     5910 | 19589 |

```
aggcattatt tgcaatatat taaagaaaac tttgaaaata cgaagtttct attcccagct  19649
ttgtctggtg gccggcatgg tcccagcctc ctcgctggcg ccggctgggc aacattccga  19709
ggggaccgtc ccctcggtaa tggcgaatgg gacgcggccg atccggctgc taacaaagcc  19769
cgaaaggaag ctgagttggc tgctgccacc gctgagcaat aactagcata accccttggg  19829
gcctctaaac gggtcttgag gggttttttg ctgaaaggag gaactatatc cggatgcggc  19889
cgcgggccct atggtaccca gcttttgttc cctttagtga gggttaattc cgagcttggc  19949
gtaatcatgg tcatagctgt ttcctgtgtg aaattgttat ccgctcacaa ttccacacaa  20009
cataggagcc ggaagcataa agtgtaaagc ctggggtgcc taatgagtga gtaactcac   20069 attaattgcg ttgcgctcac tgcccgcttt ccagtcggga aacctgtcgt gccagctgca  20129
ttaatgaatc ggccaacgcg cggggagagg cggtttgcgt attgggcgct cttccgcttc  20189
ctcgctcact gactcgctgc gctcggtcgt tcggctgcgg cgagcggtat cagctcactc  20249
aaaggcggta atacggttat ccacagaatc agggggataac gcaggaaaga acatgtgagc  20309
aaaaggccag caaaaggcca ggaaccgtaa aaaggccgcg ttgctggcgt ttttccatag  20369
gctcggcccc cctgacgagc atcacaaaaa tcgacgctca agtcagaggt ggcgaaaccc  20429
gacaggacta taaagatacc aggcgttccc ccctggaagc tccctcgtgc gctctcctgt  20489
tccgaccctg ccgcttaccg gatacctgtc cgcctttctc ccttcgggaa gcgtggcgct  20549
ttctcaatgc tcacgctgta ggtatctcag ttcggtgtag gtcgttcgct ccaagctggg  20609
ctgtgtgcac gaaccccccg ttcagcccga ccgctgcgcc ttatccggta actatcgtct  20669
tgagtccaac ccggtaagac acgacttatc gccactggca gcagccactg gtaacaggat  20729
tagcagagcg aggtatgtag gcggtgctac agagttcttg aagtggtggc ctaactacgg  20789
ctacactaga aggacagtat ttggtatctg cgctctgctg aagccagtta ccttcggaaa  20849
aagagttggt agctcttgat ccggcaaaca aaccaccgct ggtagcggtg gtttttttgt  20909
ttgcaagcag cagattacgc gcagaaaaaa aggatctcaa gaagatcctt tgatcttttc  20969
tacggggtct gacgctcagt ggaacgaaaa ctcacgttaa gggattttgg tcatgagatt  21029
atcaaaaagg atcttcacct agatcctttt aaattaaaaa tgaagtttta atcaatcta   21089 aagtatatat gagtaaactt ggtctgacag ttaccaatgc ttaatcagtg aggcacctat  21149
ctcagcgatc tgtctatttc gttcatccat agttgcctga ctccccgtcg tgtagataac  21209
tacgatacgg gagggcttac catctggccc cagtgctgca atgataccgc gagacccacg  21269
ctcaccggct ccagatttat cagcaataaa ccagccagcc ggaagggccg agcgcagaag  21329
tggtcctgca actttatccg cctccatcca gtctattaat tgttgccggg aagctagagt  21389
aagtagttcg ccagttaata gtttgcgcaa cgttgttgcc attgctacag gcatcgtggt  21449
gtcacgctcg tcgtttggta tggcttcatt cagctccggt tcccaacgat caaggcgagt  21509
tacatgatcc cccatgttgt gaaaaaaagc ggttagctcc ttcggtcctc cgatcgttgt  21569
cagaagtaag ttggccgcag tgttatcact catgcttatg gcagcactgc ataattctct  21629
tactgtcatg ccatccgtaa gatgcttttc tgtgactggt gagtactcaa ccaagtcatt  21689
ctgagaatag tgtatgcggc gaccgagttg ctcttgcccg gcgtcaatac gggataatac  21749
cgcgccacat agcagaactt taaaagtgct catcattgga aaacgttctt cggggcgaaa  21809
actctcaagg atcttaccgc tgttgagatc cagttcgatg taacccactc gtgcacccaa  21869
ctgatcttca gcatctttta ctttcaccag cgtttctggg tgagcaaaaa caggaaggca  21929
aaatgccgca aaaaagggaa taagggcgac acggaaatgt tgaatactca tactcttcct  21989
```

-continued

```
tttcaatat tattgaagca tttatcaggg ttattgtctc atgagcggat acatatttga  22049
atgtatttag aaaaataaac aaatagggt tccgcgcaca tttccccgaa aagtgccacc   22109
tgaaattgta aacgttaata ttttgttaaa attcgcgtta aattttgtt aaatcagctc   22169 attttttaac caataggccg aaatcggcaa aatcccttat aaatcaaaag aatagaccga  22229
gatagggttg agtgttgttc cagtttggaa caagagtcca ctattaaaga acgtggactc  22289
caacgtcaaa gggcgaaaaa ccgtctatca gggcgatggc ccactacgtg aaccatcacc  22349
ctaatcaagt tttttggggt cgaggtgccg taaagcacta atcggaacc ctaaagggag    22409 cccccgattt agagcttgac ggggaaagcc ggcgaacgtg gcgagaaagg aagggaagaa  22469
agcgaaagga gcgggcgcta gggcgctggc aagtgtagcg gtcacgctgc gcgtaaccac  22529
cacacccgcc gcgcttaatg cgccgctaca gggcgcgtcc cattcgccat tcaggctgcg  22589
caactgttgg gaagggcgat cggtgcgggc ctcttcgcta ttacgccagc caccgcggtg  22649
```

<210> SEQ ID NO 4
<211> LENGTH: 525
<212> TYPE: PRT
<213> ORGANISM: Artificial Sequence
<220> FEATURE:
<223> OTHER INFORMATION: Synthetic Construct

<400> SEQUENCE: 4

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
    130                 135                 140

Gly Trp Phe Gly Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
```

```
                    245                 250                 255
Ile Asp Thr Tyr Ile Val Glu Ala Gly Leu Ala Ser Phe Ile Leu Thr
                260                 265                 270

Ile Lys Phe Gly Ile Glu Thr Met Tyr Pro Ala Leu Gly Leu His Glu
            275                 280                 285

Phe Ala Gly Glu Leu Ser Thr Leu Glu Ser Leu Met Asn Leu Tyr Gln
        290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
    370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
    450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525

<210> SEQ ID NO 5
<211> LENGTH: 507
<212> TYPE: PRT
<213> ORGANISM: Artificial Sequence
<220> FEATURE:
<223> OTHER INFORMATION: Synthetic Construct

<400> SEQUENCE: 5

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser Asp Asn Pro Gly Gln Glu Arg Ala
        35                  40                  45

Thr Cys Arg Glu Glu Lys Ala Gly Ser Ser Gly Leu Ser Lys Pro Cys
    50                  55                  60

Leu Ser Ala Ile Gly Ser Thr Glu Gly Ala Pro Arg Ile Arg Gly
65                  70                  75                  80

Gln Gly Pro Gly Glu Ser Asp Asp Asp Ala Glu Thr Leu Gly Ile Pro
```

```
                      85                  90                  95
Pro Arg Asn Leu Gln Ala Ser Ser Thr Gly Leu Gln Cys Tyr Tyr Val
                    100                 105                 110

Tyr Asp His Ser Gly Glu Ala Val Lys Gly Ile Gln Asp Ala Asp Ser
                115                 120                 125

Ile Met Val Gln Ser Gly Leu Asp Gly Asp Ser Thr Leu Ser Gly Gly
            130                 135                 140

Asp Asn Glu Ser Glu Asn Ser Asp Val Asp Ile Gly Glu Pro Asp Thr
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
                180                 185                 190

Leu Leu Arg Leu Gln Ser Arg Gly Asn Asn Phe Pro Lys Leu Gly Lys
            195                 200                 205

Thr Leu Asn Val Pro Pro Pro Asp Pro Gly Arg Ala Ser Thr Ser
            210                 215                 220

Gly Thr Pro Ile Lys Lys Gly Thr Asp Ala Arg Leu Ala Ser Phe Gly
225                 230                 235                 240

Thr Glu Ile Ala Ser Leu Leu Thr Gly Gly Ala Thr Gln Cys Ala Arg
                245                 250                 255

Lys Ser Pro Ser Glu Pro Ser Gly Pro Gly Ala Pro Ala Gly Asn Val
                260                 265                 270

Pro Glu Cys Val Ser Asn Ala Ala Leu Ile Gln Glu Trp Thr Pro Glu
            275                 280                 285

Ser Gly Thr Thr Ile Ser Pro Arg Ser Gln Asn Asn Glu Glu Gly Gly
            290                 295                 300

Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
                325                 330                 335

Glu Ser Leu Leu Leu Leu Lys Gly Glu Val Glu Ser Ile Lys Lys Gln
                340                 345                 350

Ile Asn Arg Gln Asn Ile Ser Ile Ser Thr Leu Glu Gly His Leu Ser
            355                 360                 365

Ser Ile Met Ile Ala Ile Pro Gly Leu Gly Lys Asp Pro Asn Asp Pro
            370                 375                 380

Thr Ala Asp Val Glu Ile Asn Pro Asp Leu Lys Pro Ile Ile Gly Arg
385                 390                 395                 400

Asp Ser Gly Arg Ala Leu Ala Glu Val Leu Lys Pro Val Ala Ser
                405                 410                 415

Arg Gln Leu Gln Gly Met Thr Asn Gly Arg Thr Ser Ser Arg Gly Gln
                420                 425                 430

Leu Leu Lys Glu Phe Gln Leu Lys Pro Ile Gly Lys Lys Met Ser Ser
            435                 440                 445

Ala Val Gly Phe Val Pro Asp Thr Gly Pro Ala Ser Arg Ser Val Ile
            450                 455                 460

Arg Ser Ile Ile Lys Ser Ser Arg Leu Glu Glu Asp Arg Lys Arg Tyr
465                 470                 475                 480

Leu Met Thr Leu Leu Asp Asp Ile Lys Gly Ala Asn Asp Leu Ala Lys
                485                 490                 495

Phe His Gln Met Leu Met Lys Ile Ile Met Lys
                500                 505
```

<210> SEQ ID NO 6
<211> LENGTH: 76
<212> TYPE: PRT
<213> ORGANISM: Artificial Sequence
<220> FEATURE:
<223> OTHER INFORMATION: Synthetic Construct

<400> SEQUENCE: 6

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 7
<211> LENGTH: 1082
<212> TYPE: PRT
<213> ORGANISM: Artificial Sequence
<220> FEATURE:
<223> OTHER INFORMATION: Synthetic Construct

<400> SEQUENCE: 7

Arg Ala Leu Val Ala Gln Cys Leu Val Cys Val Pro Trp Asp Ala Arg
1               5                   10                  15

Pro Pro Pro Ala Ala Pro Ser Phe Arg Gln Val Ser Cys Leu Lys Glu
            20                  25                  30

Leu Val Ala Arg Val Leu Gln Arg Leu Cys Glu Arg Gly Ala Lys Asn
        35                  40                  45

Val Leu Ala Phe Gly Phe Ala Leu Leu Asp Gly Ala Arg Gly Gly Pro
    50                  55                  60

Pro Glu Ala Phe Thr Thr Ser Val Arg Ser Tyr Leu Pro Asn Thr Val
65                  70                  75                  80

Thr Asp Ala Leu Arg Gly Ser Gly Ala Trp Gly Leu Leu Leu Arg Arg
                85                  90                  95

Val Gly Asp Asp Val Leu Val His Leu Leu Ala Arg Cys Ala Leu Phe
            100                 105                 110

Val Leu Val Ala Pro Ser Cys Ala Tyr Gln Val Cys Gly Pro Pro Leu
        115                 120                 125

Tyr Gln Leu Gly Ala Ala Thr Gln Ala Arg Pro Pro Pro His Ala Ser
    130                 135                 140

Gly Pro Arg Arg Arg Leu Gly Cys Glu Arg Ala Trp Asn His Ser Val
145                 150                 155                 160

Arg Glu Ala Gly Val Pro Leu Gly Leu Pro Ala Pro Gly Ala Arg Arg
                165                 170                 175

Arg Gly Gly Ser Ala Ser Arg Ser Leu Pro Leu Pro Lys Arg Pro Arg
            180                 185                 190

Arg Gly Ala Ala Pro Glu Pro Glu Arg Thr Pro Val Gly Gln Gly Ser
        195                 200                 205

Trp Ala His Pro Gly Arg Thr Arg Gly Pro Ser Asp Arg Gly Phe Cys
    210                 215                 220

Val Val Ser Pro Ala Arg Pro Ala Glu Glu Ala Thr Ser Leu Glu Gly

-continued

```
                225                 230                 235                 240
        Ala Leu Ser Gly Thr Arg His Ser His Pro Ser Val Gly Arg Gln His
                        245                 250                 255

His Ala Gly Pro Pro Ser Thr Ser Arg Pro Pro Arg Pro Trp Asp Thr
                        260                 265                 270

Pro Cys Pro Val Tyr Ala Glu Thr Lys His Phe Leu Tyr Ser Ser
                        275                 280                 285

Gly Asp Lys Glu Gln Leu Arg Pro Ser Phe Leu Leu Ser Ser Leu Arg
                        290                 295                 300

Pro Ser Leu Thr Gly Ala Arg Arg Leu Val Glu Thr Ile Phe Leu Gly
        305                 310                 315                 320

Ser Arg Pro Trp Met Pro Gly Thr Pro Arg Arg Leu Pro Arg Leu Pro
                        325                 330                 335

Gln Arg Tyr Trp Gln Met Arg Pro Leu Phe Leu Glu Leu Leu Gly Asn
                        340                 345                 350

His Ala Gln Cys Pro Tyr Gly Val Leu Leu Lys Thr His Cys Pro Leu
                        355                 360                 365

Arg Ala Ala Val Thr Pro Ala Ala Gly Val Cys Ala Arg Glu Lys Pro
                        370                 375                 380

Gln Gly Ser Val Ala Ala Pro Glu Glu Glu Asp Thr Asp Pro Arg Arg
        385                 390                 395                 400

Leu Val Gln Leu Leu Arg Gln His Ser Ser Pro Trp Gln Val Tyr Gly
                        405                 410                 415

Phe Val Arg Ala Cys Leu Arg Arg Leu Val Pro Pro Gly Leu Trp Gly
                        420                 425                 430

Ser Arg His Asn Glu Arg Arg Phe Leu Arg Asn Thr Lys Lys Phe Ile
                        435                 440                 445

Ser Leu Gly Lys His Ala Lys Leu Ser Leu Gln Glu Leu Thr Trp Lys
                        450                 455                 460

Met Ser Val Arg Gly Cys Ala Trp Leu Arg Arg Ser Pro Gly Val Gly
        465                 470                 475                 480

Cys Val Pro Ala Ala Glu His Arg Leu Arg Glu Ile Leu Ala Lys
                        485                 490                 495

Phe Leu His Trp Leu Met Ser Val Tyr Val Val Glu Leu Leu Arg Ser
                        500                 505                 510

Phe Phe Tyr Val Thr Glu Thr Thr Phe Gln Lys Asn Arg Leu Phe Phe
                        515                 520                 525

Tyr Arg Lys Ser Val Trp Ser Lys Leu Gln Ser Ile Gly Ile Arg Gln
                        530                 535                 540

His Leu Lys Arg Val Gln Leu Arg Glu Leu Ser Glu Ala Glu Val Arg
        545                 550                 555                 560

Gln His Arg Glu Ala Arg Pro Ala Leu Leu Thr Ser Arg Leu Arg Phe
                        565                 570                 575

Ile Pro Lys Pro Asp Gly Leu Arg Pro Ile Val Asn Met Asp Tyr Val
                        580                 585                 590

Val Gly Ala Arg Thr Phe Arg Arg Glu Lys Arg Ala Glu Arg Leu Thr
                        595                 600                 605

Ser Arg Val Lys Ala Leu Phe Ser Val Leu Asn Tyr Glu Arg Ala Arg
                        610                 615                 620

Arg Pro Gly Leu Leu Gly Ala Ser Val Leu Gly Leu Asp Asp Ile His
        625                 630                 635                 640

Arg Ala Trp Arg Thr Phe Val Leu Arg Val Arg Ala Gln Asp Pro Pro
                        645                 650                 655
```

```
Pro Glu Leu Tyr Phe Val Lys Val Asp Val Thr Gly Ala Tyr Asp Thr
            660                 665                 670

Ile Pro Gln Asp Arg Leu Thr Glu Val Ile Ala Ser Ile Ile Lys Pro
        675                 680                 685

Gln Asn Thr Tyr Cys Val Arg Arg Tyr Ala Val Gln Lys Ala Ala
    690                 695                 700

His Gly His Val Arg Lys Ala Phe Lys Ser His Val Ser Thr Leu Thr
705                 710                 715                 720

Asp Leu Gln Pro Tyr Met Arg Gln Phe Val Ala His Leu Gln Glu Thr
                725                 730                 735

Ser Pro Leu Arg Asp Ala Val Val Ile Glu Gln Ser Ser Leu Asn
            740                 745                 750

Glu Ala Ser Ser Gly Leu Phe Asp Val Phe Leu Arg Phe Met Cys His
        755                 760                 765

His Ala Val Arg Ile Arg Gly Lys Ser Tyr Val Gln Cys Gln Gly Ile
    770                 775                 780

Pro Gln Gly Ser Ile Leu Ser Thr Leu Leu Cys Ser Leu Cys Tyr Gly
785                 790                 795                 800

Asp Met Glu Asn Lys Leu Phe Ala Gly Ile Arg Arg Asp Gly Leu Leu
                805                 810                 815

Leu Arg Leu Phe Leu Leu Val Thr Pro His Leu Thr His Ala Lys Thr
            820                 825                 830

Phe Leu Arg Thr Leu Val Arg Gly Val Pro Glu Tyr Gly Cys Val Val
        835                 840                 845

Asn Leu Arg Lys Thr Val Val Asn Phe Pro Val Glu Asp Glu Ala Leu
    850                 855                 860

Gly Gly Thr Ala Phe Val Gln Met Pro Ala His Gly Leu Phe Pro Trp
865                 870                 875                 880

Cys Gly Leu Leu Leu Asp Thr Arg Thr Leu Glu Val Gln Ser Asp Tyr
                885                 890                 895

Ser Ser Tyr Ala Arg Thr Ser Ile Arg Ala Ser Leu Thr Phe Asn Arg
            900                 905                 910

Gly Phe Lys Ala Gly Arg Asn Met Arg Arg Lys Leu Phe Gly Val Leu
        915                 920                 925

Arg Leu Lys Cys His Ser Leu Phe Leu Asp Leu Gln Val Asn Ser Leu
    930                 935                 940

Gln Thr Val Cys Thr Asn Ile Tyr Lys Ile Leu Leu Gln Ala Tyr
945                 950                 955                 960

Arg Phe His Ala Cys Val Leu Gln Leu Pro Phe His Gln Val Trp
                965                 970                 975

Lys Asn Pro Thr Phe Phe Leu Arg Val Ile Ser Asp Thr Ala Ser Leu
            980                 985                 990

Cys Tyr Ser Ile Leu Lys Ala Lys Asn Ala Gly Met Ser Leu Gly Ala
        995                 1000                1005

Lys Gly Ala Ala Gly Pro Leu Pro Ser Glu Ala Val Gln Trp Leu
    1010                1015                1020

Cys His Gln Ala Phe Leu Leu Lys Leu Thr Arg His Arg Val Thr
    1025                1030                1035

Tyr Val Pro Leu Leu Gly Ser Leu Arg Thr Ala Gln Thr Gln Leu
    1040                1045                1050

Ser Arg Lys Leu Pro Gly Thr Thr Leu Thr Ala Leu Glu Ala Ala
    1055                1060                1065
```

```
Ala Asn Pro Ala Leu Pro Ser Asp Phe Lys Thr Ile Leu Asp
    1070                1075                1080
```

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct

<400> SEQUENCE: 8

```
Thr Glu Leu Lys Leu Ser Asp Tyr Glu Gly Arg Leu Ile Gln Asn Ser
1               5                   10                  15

Leu Thr
```

<210> SEQ ID NO 9
<211> LENGTH: 14
<212> TYPE: PRT
<213> ORGANISM: Artificial Sequence
<220> FEATURE:
<223> OTHER INFORMATION: Synthetic Construct

<400> SEQUENCE: 9

```
Gly Lys Pro Ile Pro Asn Pro Leu Leu Gly Leu Asp Ser Thr
1               5                   10
```

<210> SEQ ID NO 10
<211> LENGTH: 335
<212> TYPE: PRT
<213> ORGANISM: Artificial Sequence
<220> FEATURE:
<223> OTHER INFORMATION: Synthetic Construct

<400> SEQUENCE: 10

```
Met Thr Glu Thr Tyr Asp Phe Asp Lys Ser Ala Trp Asp Ile Lys Gly
1               5                   10                  15

Ser Ile Ala Pro Ile Gln Pro Thr Thr Tyr Ser Asp Gly Arg Leu Val
            20                  25                  30

Pro Gln Val Arg Val Ile Asp Pro Gly Leu Gly Asp Arg Lys Asp Glu
        35                  40                  45

Cys Phe Met Tyr Met Phe Leu Leu Gly Val Val Glu Asp Ser Asp Ser
    50                  55                  60

Leu Gly Pro Pro Ile Gly Arg Ala Phe Gly Phe Leu Pro Leu Gly Val
65                  70                  75                  80

Gly Arg Ser Thr Ala Lys Pro Glu Lys Leu Leu Lys Glu Ala Thr Glu
                85                  90                  95

Leu Asp Ile Val Val Arg Arg Thr Ala Gly Leu Asn Glu Lys Leu Val
            100                 105                 110

Phe Tyr Asn Asn Thr Pro Leu Thr Leu Leu Thr Pro Trp Arg Lys Val
        115                 120                 125

Leu Thr Thr Gly Ser Val Phe Asn Ala Asn Gln Val Cys Asn Ala Val
    130                 135                 140

Asn Leu Ile Pro Leu Asp Thr Pro Gln Arg Phe Arg Val Val Tyr Met
145                 150                 155                 160

Ser Ile Thr Arg Leu Ser Asp Asn Gly Tyr Tyr Thr Val Pro Arg Arg
                165                 170                 175

Met Leu Glu Phe Arg Ser Val Asn Ala Val Ala Phe Asn Leu Leu Val
            180                 185                 190

Thr Leu Arg Ile Asp Lys Ala Ile Gly Pro Gly Lys Ile Ile Asp Asn
        195                 200                 205
```

Thr Glu Gln Leu Pro Glu Ala Thr Phe Met Val His Ile Gly Asn Phe
    210                 215                 220

Arg Arg Lys Lys Ser Glu Val Tyr Ser Ala Asp Tyr Cys Lys Met Lys
225                 230                 235                 240

Ile Glu Lys Met Gly Leu Val Phe Ala Leu Gly Gly Ile Gly Gly Thr
                245                 250                 255

Ser Leu His Ile Arg Ser Thr Gly Lys Met Ser Lys Thr Leu His Ala
                260                 265                 270

Gln Leu Gly Phe Lys Lys Thr Leu Cys Tyr Pro Leu Met Asp Ile Asn
            275                 280                 285

Glu Asp Leu Asn Arg Leu Leu Trp Arg Ser Arg Cys Lys Ile Val Arg
    290                 295                 300

Ile Gln Ala Val Leu Gln Pro Ser Val Pro Gln Glu Phe Arg Ile Tyr
305                 310                 315                 320

Asp Asp Val Ile Ile Asn Asp Asp Gln Gly Leu Phe Lys Val Leu
                325                 330                 335

<210> SEQ ID NO 11
<211> LENGTH: 553
<212> TYPE: PRT
<213> ORGANISM: Artificial Sequence
<220> FEATURE:
<223> OTHER INFORMATION: Synthetic Construct

<400> SEQUENCE: 11

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
                100                 105                 110

His Lys Arg Phe Ala Gly Val Val Leu Ala Gly Ala Ala Leu Gly Val
            115                 120                 125

Ala Thr Ala Ala Gln Ile Thr Ala Gly Ile Ala Leu His Gln Ser Met
130                 135                 140

Leu Asn Ser Gln Ala Ile Asp Asn Leu Arg Ala Ser Leu Glu Thr Thr
145                 150                 155                 160

Asn Gln Ala Ile Glu Thr Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

-continued

Leu Gly Gly Asp Ile Asn Lys Val Leu Glu Lys Leu Gly Tyr Ser Gly
                245                 250                 255

Gly Asp Leu Leu Gly Ile Leu Glu Ser Gly Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Tyr Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg Cys Asn Lys Lys Gly
        515                 520                 525

Glu Gln Val Gly Met Ser Arg Pro Gly Leu Lys Pro Asp Leu Thr Gly
    530                 535                 540

Thr Ser Lys Ser Tyr Val Arg Ser Leu
545                 550

<210> SEQ ID NO 12
<211> LENGTH: 617
<212> TYPE: PRT
<213> ORGANISM: Artificial Sequence
<220> FEATURE:
<223> OTHER INFORMATION: Synthetic Construct

<400> SEQUENCE: 12

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

```
Leu Ile Gly Leu Leu Ala Ile Ala Gly Ile Arg Leu His Arg Ala Ala
         50                  55                  60
Ile Tyr Thr Ala Glu Ile His Lys Ser Leu Ser Thr Asn Leu Asp Val
 65                  70                  75                  80
Thr Asn Ser Ile Glu His Gln Val Lys Asp Val Leu Thr Pro Leu Phe
                 85                  90                  95
Lys Ile Ile Gly Asp Glu Val Gly Leu Arg Thr Pro Gln Arg Phe Thr
             100                 105                 110
Asp Leu Val Lys Leu Ile Ser Asp Lys Ile Lys Phe Leu Asn Pro Asp
         115                 120                 125
Arg Glu Tyr Asp Phe Arg Asp Leu Thr Trp Cys Ile Asn Pro Pro Glu
     130                 135                 140
Arg Ile Lys Leu Asp Tyr Asp Gln Tyr Cys Ala Asp Val Ala Ala Glu
145                 150                 155                 160
Glu Leu Met Asn Ala Leu Val Asn Ser Thr Leu Leu Glu Thr Arg Thr
                 165                 170                 175
Thr Asn Gln Phe Leu Ala Val Ser Lys Gly Asn Cys Ser Gly Pro Thr
             180                 185                 190
Thr Ile Arg Gly Gln Phe Ser Asn Met Ser Leu Ser Leu Leu Asp Leu
         195                 200                 205
Tyr Leu Gly Arg Gly Tyr Asn Val Ser Ser Ile Val Thr Met Thr Ser
     210                 215                 220
Gln Gly Met Tyr Gly Gly Thr Tyr Leu Val Glu Lys Pro Asn Leu Ser
225                 230                 235                 240
Ser Lys Arg Ser Glu Leu Ser Gln Leu Ser Met Tyr Arg Val Phe Glu
                 245                 250                 255
Val Gly Val Ile Arg Asn Pro Gly Leu Gly Ala Pro Val Phe His Met
             260                 265                 270
Thr Asn Tyr Leu Glu Gln Pro Val Ser Asn Asp Leu Ser Asn Cys Met
         275                 280                 285
Val Ala Leu Gly Glu Leu Lys Leu Ala Ala Leu Cys His Gly Glu Asp
     290                 295                 300
Ser Ile Thr Ile Pro Tyr Gln Gly Ser Gly Lys Gly Val Ser Phe Gln
305                 310                 315                 320
Leu Val Lys Leu Gly Val Trp Lys Ser Pro Thr Asp Met Gln Ser Trp
                 325                 330                 335
Val Pro Leu Ser Thr Asp Asp Pro Val Ile Asp Arg Leu Tyr Leu Ser
             340                 345                 350
Ser His Arg Gly Val Ile Ala Asp Asn Gln Ala Lys Trp Ala Val Pro
         355                 360                 365
Thr Thr Arg Thr Asp Asp Lys Leu Arg Met Glu Thr Cys Phe Gln Gln
     370                 375                 380
Ala Cys Lys Gly Lys Ile Gln Ala Leu Cys Glu Asn Pro Glu Trp Ala
385                 390                 395                 400
Pro Leu Lys Asp Asn Arg Ile Pro Ser Tyr Gly Val Leu Ser Val Asp
                 405                 410                 415
Leu Ser Leu Thr Val Glu Leu Lys Ile Lys Ile Ala Ser Gly Phe Gly
             420                 425                 430
Pro Leu Ile Thr His Gly Ser Gly Met Asp Leu Tyr Lys Ser Asn His
         435                 440                 445
Asn Asn Val Tyr Trp Leu Thr Ile Pro Pro Met Lys Asn Leu Ala Leu
     450                 455                 460
```

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Glu Asp Cys His Ala
            485                 490                 495

Pro Thr Tyr Leu Pro Ala Glu Val Asp Gly Asp Val Lys Leu Ser Ser
        500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
            565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605

Thr Arg Glu Asp Gly Thr Asn Arg Arg
    610                 615

<210> SEQ ID NO 13
<211> LENGTH: 2183
<212> TYPE: PRT
<213> ORGANISM: Artificial Sequence
<220> FEATURE:
<223> OTHER INFORMATION: Synthetic Construct

<400> SEQUENCE: 13

Met Asp Ser Leu Ser Val Asn Gln Ile Leu Tyr Pro Glu Val His Leu
1               5                   10                  15

Asp Ser Pro Ile Val Thr Asn Lys Ile Val Ala Ile Leu Glu Tyr Ala
            20                  25                  30

Arg Val Pro His Ala Tyr Ser Leu Glu Asp Pro Thr Leu Cys Gln Asn
        35                  40                  45

Ile Lys His Arg Leu Lys Asn Gly Phe Ser Asn Gln Met Ile Ile Asn
    50                  55                  60

Asn Val Glu Val Gly Asn Val Ile Lys Ser Lys Leu Arg Ser Tyr Pro
65                  70                  75                  80

Ala His Ser His Ile Pro Tyr Pro Asn Cys Asn Gln Asp Leu Phe Asn
                85                  90                  95

Ile Glu Asp Lys Glu Ser Thr Arg Lys Ile Arg Glu Leu Leu Lys Lys
            100                 105                 110

Gly Asn Ser Leu Tyr Ser Lys Val Ser Asp Lys Val Phe Gln Cys Leu
        115                 120                 125

Arg Asp Thr Asn Ser Arg Leu Gly Leu Gly Ser Glu Leu Arg Glu Asp
    130                 135                 140

Ile Lys Glu Lys Val Ile Asn Leu Gly Val Tyr Met His Ser Ser Gln
145                 150                 155                 160

Trp Phe Glu Pro Phe Leu Phe Trp Phe Thr Val Lys Thr Glu Met Arg
                165                 170                 175

Ser Val Ile Lys Ser Gln Thr His Thr Cys His Arg Arg His Thr
            180                 185                 190

Pro Val Phe Phe Thr Gly Ser Ser Val Glu Leu Leu Ile Ser Arg Asp
        195                 200                 205

```
Leu Val Ala Ile Ile Ser Lys Glu Ser Gln His Val Tyr Tyr Leu Thr
210                 215                 220

Phe Glu Leu Val Leu Met Tyr Cys Asp Val Ile Glu Gly Arg Leu Met
225                 230                 235                 240

Thr Glu Thr Ala Met Thr Ile Asp Ala Arg Tyr Thr Glu Leu Leu Gly
                245                 250                 255

Arg Val Arg Tyr Met Trp Lys Leu Ile Asp Gly Phe Phe Pro Ala Leu
                260                 265                 270

Gly Asn Pro Thr Tyr Gln Ile Val Ala Met Leu Glu Pro Leu Ser Leu
                275                 280                 285

Ala Tyr Leu Gln Leu Arg Asp Ile Thr Val Glu Leu Arg Gly Ala Phe
290                 295                 300

Leu Asn His Cys Phe Thr Glu Ile His Asp Val Leu Asp Gln Asn Gly
305                 310                 315                 320

Phe Ser Asp Glu Gly Thr Tyr His Glu Leu Thr Glu Ala Leu Asp Tyr
                325                 330                 335

Ile Phe Ile Thr Asp Asp Ile His Leu Thr Gly Glu Ile Phe Ser Phe
                340                 345                 350

Phe Arg Ser Phe Gly His Pro Arg Leu Glu Ala Val Thr Ala Ala Glu
                355                 360                 365

Asn Val Arg Lys Tyr Met Asn Gln Pro Lys Val Ile Val Tyr Glu Thr
370                 375                 380

Leu Met Lys Gly His Ala Ile Phe Cys Gly Ile Ile Asn Gly Tyr
385                 390                 395                 400

Arg Asp Arg His Gly Gly Ser Trp Pro Pro Leu Thr Leu Pro Leu His
                405                 410                 415

Ala Ala Asp Thr Ile Arg Asn Ala Gln Ala Ser Gly Glu Gly Leu Thr
                420                 425                 430

His Glu Gln Cys Val Asp Asn Trp Lys Ser Phe Ala Gly Val Lys Phe
                435                 440                 445

Gly Cys Phe Met Pro Leu Ser Leu Asp Ser Asp Leu Thr Met Tyr Leu
450                 455                 460

Lys Asp Lys Ala Leu Ala Ala Leu Gln Arg Glu Trp Asp Ser Val Tyr
465                 470                 475                 480

Pro Lys Glu Phe Leu Arg Tyr Asp Pro Pro Lys Gly Thr Gly Ser Arg
                485                 490                 495

Arg Leu Val Asp Val Phe Leu Asn Asp Ser Ser Phe Asp Pro Tyr Asp
                500                 505                 510

Val Ile Met Tyr Val Val Ser Gly Ala Tyr Leu His Asp Pro Glu Phe
                515                 520                 525

Asn Leu Ser Tyr Ser Leu Lys Glu Lys Glu Ile Lys Glu Thr Gly Arg
530                 535                 540

Leu Phe Ala Lys Met Thr Tyr Lys Met Arg Ala Cys Gln Val Ile Ala
545                 550                 555                 560

Glu Asn Leu Ile Ser Asn Gly Ile Gly Lys Tyr Phe Lys Asp Asn Gly
                565                 570                 575

Met Ala Lys Asp Glu His Asp Leu Thr Lys Ala Leu His Thr Leu Ala
                580                 585                 590

Val Ser Gly Val Pro Lys Asp Leu Lys Glu Ser His Arg Gly Gly Pro
                595                 600                 605

Val Leu Lys Thr Tyr Ser Arg Ser Pro Val His Thr Ser Thr Arg Asn
610                 615                 620

Val Arg Ala Ala Lys Gly Phe Ile Gly Phe Pro Gln Val Ile Arg Gln
```

-continued

```
            625                 630                 635                 640

Asp Gln Asp Thr Asp His Pro Glu Asn Met Glu Ala Tyr Glu Thr Val
                645                 650                 655

Ser Ala Phe Ile Thr Asp Leu Lys Lys Tyr Cys Leu Asn Trp Arg
        660                 665                 670

Tyr Glu Thr Ile Ser Leu Phe Ala Gln Arg Leu Asn Glu Ile Tyr Gly
                675                 680                 685

Leu Pro Ser Phe Phe Gln Trp Leu His Lys Arg Leu Glu Thr Ser Val
690                 695                 700

Leu Tyr Val Ser Asp Pro His Cys Pro Pro Asp Leu Asp Ala His Ile
705                 710                 715                 720

Pro Leu Tyr Lys Val Pro Asn Asp Gln Ile Phe Ile Lys Tyr Pro Met
                725                 730                 735

Gly Gly Ile Glu Gly Tyr Cys Gln Lys Leu Trp Thr Ile Ser Thr Ile
                740                 745                 750

Pro Tyr Leu Tyr Leu Ala Ala Tyr Glu Ser Gly Val Arg Ile Ala Ser
                755                 760                 765

Leu Val Gln Gly Asp Asn Gln Thr Ile Ala Val Thr Lys Arg Val Pro
770                 775                 780

Ser Thr Trp Pro Tyr Asn Leu Lys Lys Arg Glu Ala Ala Arg Val Thr
785                 790                 795                 800

Arg Asp Tyr Phe Val Ile Leu Arg Gln Arg Leu His Asp Ile Gly His
                805                 810                 815

His Leu Lys Ala Asn Glu Thr Ile Val Ser Ser His Phe Phe Val Tyr
                820                 825                 830

Ser Lys Gly Ile Tyr Tyr Asp Gly Leu Leu Val Ser Gln Ser Leu Lys
                835                 840                 845

Ser Ile Ala Arg Cys Val Phe Trp Ser Glu Thr Ile Val Asp Glu Thr
850                 855                 860

Arg Ala Ala Cys Ser Asn Ile Ala Thr Thr Met Ala Lys Ser Ile Glu
865                 870                 875                 880

Arg Gly Tyr Asp Arg Tyr Leu Ala Tyr Ser Leu Asn Val Leu Lys Val
                885                 890                 895

Ile Gln Gln Ile Leu Ile Ser Leu Gly Phe Thr Ile Asn Ser Thr Met
                900                 905                 910

Thr Arg Asp Val Val Ile Pro Leu Leu Thr Asn Asn Asp Leu Leu Ile
                915                 920                 925

Arg Met Ala Leu Leu Pro Ala Pro Ile Gly Gly Met Asn Tyr Leu Asn
                930                 935                 940

Met Ser Arg Leu Phe Val Arg Asn Ile Gly Asp Pro Val Thr Ser Ser
945                 950                 955                 960

Ile Ala Asp Leu Lys Arg Met Ile Leu Ala Ser Leu Met Pro Glu Glu
                965                 970                 975

Thr Leu His Gln Val Met Thr Gln Gln Pro Gly Asp Ser Ser Phe Leu
                980                 985                 990

Asp Trp Ala Ser Asp Pro Tyr Ser Ala Asn Leu Val Cys Val Gln Ser
                995                 1000                1005

Ile Thr Arg Leu Leu Lys Asn Ile Thr Ala Arg Phe Val Leu Ile
        1010                1015                1020

His Ser Pro Asn Pro Met Leu Lys Gly Leu Phe His Asp Asp Ser
        1025                1030                1035

Lys Glu Glu Asp Glu Gly Leu Ala Ala Phe Leu Met Asp Arg His
        1040                1045                1050
```

```
Ile Ile Val Pro Arg Ala Ala His Glu Ile Leu Asp His Ser Val
1055                1060                1065

Thr Gly Ala Arg Glu Ser Ile Ala Gly Met Leu Asp Thr Thr Lys
1070                1075                1080

Gly Leu Ile Arg Ala Ser Met Arg Lys Gly Gly Leu Thr Ser Arg
1085                1090                1095

Val Ile Thr Arg Leu Ser Asn Tyr Asp Tyr Glu Gln Phe Arg Ala
1100                1105                1110

Gly Met Val Leu Leu Thr Gly Arg Lys Arg Asn Val Leu Ile Asp
1115                1120                1125

Lys Glu Ser Cys Ser Val Gln Leu Ala Arg Ala Leu Arg Ser His
1130                1135                1140

Met Trp Ala Arg Leu Ala Arg Gly Arg Pro Ile Tyr Gly Leu Glu
1145                1150                1155

Val Pro Asp Val Leu Glu Ser Met Arg Gly His Leu Ile Arg Arg
1160                1165                1170

His Glu Thr Cys Val Ile Cys Glu Cys Gly Ser Val Asn Tyr Gly
1175                1180                1185

Trp Phe Phe Val Pro Ser Gly Cys Gln Leu Asp Asp Ile Asp Lys
1190                1195                1200

Glu Thr Ser Ser Leu Arg Val Pro Tyr Ile Gly Ser Thr Thr Asp
1205                1210                1215

Glu Arg Thr Asp Met Lys Leu Ala Phe Val Arg Ala Pro Ser Arg
1220                1225                1230

Ser Leu Arg Ser Ala Val Arg Ile Ala Thr Val Tyr Ser Trp Ala
1235                1240                1245

Tyr Gly Asp Asp Asp Ser Ser Trp Asn Glu Ala Trp Leu Leu Ala
1250                1255                1260

Arg Gln Arg Ala Asn Val Ser Leu Glu Glu Leu Arg Val Ile Thr
1265                1270                1275

Pro Ile Ser Thr Ser Thr Asn Leu Ala His Arg Leu Arg Asp Arg
1280                1285                1290

Ser Thr Gln Val Lys Tyr Ser Gly Thr Ser Leu Val Arg Val Ala
1295                1300                1305

Arg Tyr Thr Thr Ile Ser Asn Asp Asn Leu Ser Phe Val Ile Ser
1310                1315                1320

Asp Lys Lys Val Asp Thr Asn Phe Ile Tyr Gln Gln Gly Met Leu
1325                1330                1335

Leu Gly Leu Gly Val Leu Glu Thr Leu Phe Arg Leu Glu Lys Asp
1340                1345                1350

Thr Gly Ser Ser Asn Thr Val Leu His Leu His Val Glu Thr Asp
1355                1360                1365

Cys Cys Val Ile Pro Met Ile Asp His Pro Arg Ile Pro Ser Ser
1370                1375                1380

Arg Lys Leu Glu Leu Arg Ala Glu Leu Cys Thr Asn Pro Leu Ile
1385                1390                1395

Tyr Asp Asn Ala Pro Leu Ile Asp Arg Asp Ala Thr Arg Leu Tyr
1400                1405                1410

Thr Gln Ser His Arg Arg His Leu Val Glu Phe Val Thr Trp Ser
1415                1420                1425

Thr Pro Gln Leu Tyr His Ile Leu Ala Lys Ser Thr Ala Leu Ser
1430                1435                1440
```

-continued

```
Met Ile Asp Leu Val Thr Lys Phe Glu Lys Asp His Met Asn Glu
    1445                1450                1455

Ile Ser Ala Leu Ile Gly Asp Asp Ile Asn Ser Phe Ile Thr
    1460                1465                1470

Glu Phe Leu Leu Ile Glu Pro Arg Leu Phe Thr Ile Tyr Leu Gly
    1475                1480                1485

Gln Cys Ala Ala Ile Asn Trp Ala Phe Asp Val His Tyr His Arg
    1490                1495                1500

Pro Ser Gly Lys Tyr Gln Met Gly Glu Leu Leu Ser Ser Phe Leu
    1505                1510                1515

Ser Arg Met Ser Lys Gly Val Phe Lys Val Leu Asn Ala Leu
    1520                1525                1530

Ser His Pro Lys Ile Tyr Lys Lys Phe Trp His Cys Gly Ile Ile
    1535                1540                1545

Glu Pro Ile His Gly Pro Ser Leu Asp Ala Gln Asn Leu His Thr
    1550                1555                1560

Thr Val Cys Asn Met Val Tyr Thr Cys Tyr Met Thr Tyr Leu Asp
    1565                1570                1575

Leu Leu Leu Asn Glu Glu Leu Glu Glu Phe Thr Phe Leu Leu Cys
    1580                1585                1590

Glu Ser Asp Glu Asp Val Val Pro Asp Arg Phe Asp Asn Ile Gln
    1595                1600                1605

Ala Lys His Leu Cys Val Leu Ala Asp Leu Tyr Cys Gln Pro Gly
    1610                1615                1620

Thr Cys Pro Pro Ile Arg Gly Leu Arg Pro Val Glu Lys Cys Ala
    1625                1630                1635

Val Leu Thr Asp His Ile Lys Ala Glu Ala Met Leu Ser Pro Ala
    1640                1645                1650

Gly Ser Ser Trp Asn Ile Asn Pro Ile Ile Val Asp His Tyr Ser
    1655                1660                1665

Cys Ser Leu Thr Tyr Leu Arg Arg Gly Ser Ile Lys Gln Ile Arg
    1670                1675                1680

Leu Arg Val Asp Pro Gly Phe Ile Phe Asp Ala Leu Ala Glu Val
    1685                1690                1695

Asn Val Ser Gln Pro Lys Ile Gly Ser Asn Asn Ile Ser Asn Met
    1700                1705                1710

Ser Ile Lys Ala Phe Arg Pro Pro His Asp Asp Val Ala Lys Leu
    1715                1720                1725

Leu Lys Asp Ile Asn Thr Ser Lys His Asn Leu Pro Ile Ser Gly
    1730                1735                1740

Gly Asn Leu Ala Asn Tyr Glu Ile His Ala Phe Arg Arg Ile Gly
    1745                1750                1755

Leu Asn Ser Ser Ala Cys Tyr Lys Ala Val Glu Ile Ser Thr Leu
    1760                1765                1770

Ile Arg Arg Cys Leu Glu Pro Gly Glu Asp Gly Leu Phe Leu Gly
    1775                1780                1785

Glu Gly Ser Gly Ser Met Leu Ile Thr Tyr Lys Glu Ile Leu Lys
    1790                1795                1800

Leu Asn Lys Cys Phe Tyr Asn Ser Gly Val Ser Ala Asn Ser Arg
    1805                1810                1815

Ser Gly Gln Arg Glu Leu Ala Pro Tyr Pro Ser Glu Val Gly Leu
    1820                1825                1830

Val Glu His Arg Met Gly Val Gly Asn Ile Val Lys Val Leu Phe
```

```
                    1835                1840                1845
Asn Gly Arg Pro Glu Val Thr Trp Val Gly Ser Val Asp Cys Phe
    1850                1855                1860
Asn Phe Ile Val Ser Asn Ile Pro Thr Ser Ser Val Gly Phe Ile
    1865                1870                1875
His Ser Asp Ile Glu Thr Leu Pro Asp Lys Asp Thr Ile Glu Lys
    1880                1885                1890
Leu Glu Glu Leu Ala Ala Ile Leu Ser Met Ala Leu Leu Leu Gly
    1895                1900                1905
Lys Ile Gly Ser Ile Leu Val Ile Lys Leu Met Pro Phe Ser Gly
    1910                1915                1920
Asp Phe Val Gln Gly Phe Ile Ser Tyr Val Gly Ser His Tyr Arg
    1925                1930                1935
Glu Val Asn Leu Val Tyr Pro Arg Tyr Ser Asn Phe Ile Ser Thr
    1940                1945                1950
Glu Ser Tyr Leu Val Met Thr Asp Leu Lys Ala Asn Arg Leu Met
    1955                1960                1965
Asn Pro Glu Lys Ile Lys Gln Gln Ile Ile Glu Ser Ser Val Arg
    1970                1975                1980
Thr Ser Pro Gly Leu Ile Gly His Ile Leu Ser Ile Lys Gln Leu
    1985                1990                1995
Ser Cys Ile Gln Ala Ile Val Gly Asp Ala Val Ser Arg Gly Asp
    2000                2005                2010
Ile Asn Pro Thr Leu Lys Lys Leu Thr Pro Ile Glu Gln Val Leu
    2015                2020                2025
Ile Asn Cys Gly Leu Ala Ile Asn Gly Pro Lys Leu Cys Lys Glu
    2030                2035                2040
Leu Ile His His Asp Val Ala Ser Gly Gln Asp Gly Leu Leu Asn
    2045                2050                2055
Ser Ile Leu Ile Leu Tyr Arg Glu Leu Ala Arg Phe Lys Asp Asn
    2060                2065                2070
Gln Arg Ser Gln Gln Gly Met Phe His Ala Tyr Pro Val Leu Val
    2075                2080                2085
Ser Ser Arg Gln Arg Glu Leu Ile Ser Arg Ile Thr Arg Lys Phe
    2090                2095                2100
Trp Gly His Ile Leu Leu Tyr Ser Gly Asn Lys Lys Leu Ile Asn
    2105                2110                2115
Lys Phe Ile Gln Asn Leu Lys Ser Gly Tyr Leu Ile Leu Asp Leu
    2120                2125                2130
His Gln Asn Ile Phe Val Lys Asn Leu Ser Lys Ser Glu Lys Gln
    2135                2140                2145
Ile Ile Met Thr Gly Gly Leu Lys Arg Glu Trp Val Phe Lys Val
    2150                2155                2160
Thr Val Lys Glu Thr Lys Glu Trp Tyr Lys Leu Val Gly Tyr Ser
    2165                2170                2175
Ala Leu Ile Lys Asp
    2180

<210> SEQ ID NO 14
<211> LENGTH: 3474
<212> TYPE: DNA
<213> ORGANISM: Artificial Sequence
<220> FEATURE:
<223> OTHER INFORMATION: Ubi - delta hTERT
<220> FEATURE:
```

```
<221> NAME/KEY: CDS
<222> LOCATION: (1)..(3474)
<223> OTHER INFORMATION: Ubi- delta hTERT

<400> SEQUENCE: 14 atg cag att ttc gtc aaa aca ttg aca gga aag acc atc aca ctg gaa      48
Met Gln Ile Phe Val Lys Thr Leu Thr Gly Lys Thr Ile Thr Leu Glu
1               5                   10                  15 gtg gag cca agc gac act att gag aac gtc aaa gcc aag att cag gac      96
Val Glu Pro Ser Asp Thr Ile Glu Asn Val Lys Ala Lys Ile Gln Asp
            20                  25                  30 aag gag ggc atc cca cca gac cag cag agg ctg att ttt gcc gga aag     144
Lys Glu Gly Ile Pro Pro Asp Gln Gln Arg Leu Ile Phe Ala Gly Lys
        35                  40                  45 cag ctg gag gac gga cgc aca ctc agt gac tac aat atc cag aag gaa     192
Gln Leu Glu Asp Gly Arg Thr Leu Ser Asp Tyr Asn Ile Gln Lys Glu
50                  55                  60 agt act ctg cat ctg gtc ctt cgc ctg cgc ggc gga aga gct ctc gtc     240
Ser Thr Leu His Leu Val Leu Arg Leu Arg Gly Gly Arg Ala Leu Val
65                  70                  75                  80 gcc cag tgt ctg gtc tgc gtt cct tgg gac gca cgg ccc cca ccc gcc     288
Ala Gln Cys Leu Val Cys Val Pro Trp Asp Ala Arg Pro Pro Pro Ala
                85                  90                  95 gcc ccc agt ttc cgg cag gtg agt tgt ctc aaa gag ttg gtt gct cgg     336
Ala Pro Ser Phe Arg Gln Val Ser Cys Leu Lys Glu Leu Val Ala Arg
            100                 105                 110 gtg ttg cag cgg ctt tgt gaa cgc gga gca aag aac gtc ctt gcc ttt     384
Val Leu Gln Arg Leu Cys Glu Arg Gly Ala Lys Asn Val Leu Ala Phe
        115                 120                 125 ggc ttc gct ttg ctc gat gga gca cgc gga ggc cct cct gag gca ttc     432
Gly Phe Ala Leu Leu Asp Gly Ala Arg Gly Gly Pro Pro Glu Ala Phe
    130                 135                 140 act act agc gtc cgg tcc tac ctg ccc aac aca gtg acc gac gct ctg     480
Thr Thr Ser Val Arg Ser Tyr Leu Pro Asn Thr Val Thr Asp Ala Leu
145                 150                 155                 160 aga ggt tca ggt gcc tgg ggt ctg ctg ctg cgg agg gtg ggt gat gat     528
Arg Gly Ser Gly Ala Trp Gly Leu Leu Leu Arg Arg Val Gly Asp Asp
                165                 170                 175 gtt ctg gtt cac ctc ctg gcc cgg tgt gcc ctg ttc gtg ctg gtg gct     576
Val Leu Val His Leu Leu Ala Arg Cys Ala Leu Phe Val Leu Val Ala
            180                 185                 190 ccc tcc tgc gca tac cag gtc tgc gga ccc cca ctt tat cag ctc ggc     624
Pro Ser Cys Ala Tyr Gln Val Cys Gly Pro Pro Leu Tyr Gln Leu Gly
        195                 200                 205 gct gct act cag gcc cgc cca cca cca cac gcc tca ggt cca aga cgc     672
Ala Ala Thr Gln Ala Arg Pro Pro Pro His Ala Ser Gly Pro Arg Arg
    210                 215                 220 cgg ctg ggc tgc gaa cgg gca tgg aat cat agc gtc cgg gag gca ggt     720
Arg Leu Gly Cys Glu Arg Ala Trp Asn His Ser Val Arg Glu Ala Gly
225                 230                 235                 240 gtg cct ctc ggc ctg cca gcc ccc gga gca agg aga cgc ggt gga tcc     768
Val Pro Leu Gly Leu Pro Ala Pro Gly Ala Arg Arg Arg Gly Gly Ser
                245                 250                 255 gcc agt cgc tca ctc ccc ttg cct aag agg cca aga aga gga gcc gcc     816
Ala Ser Arg Ser Leu Pro Leu Pro Lys Arg Pro Arg Arg Gly Ala Ala
            260                 265                 270 cct gaa ccc gag aga aca cct gtc ggc cag ggc tcc tgg gct cac ccc     864
Pro Glu Pro Glu Arg Thr Pro Val Gly Gln Gly Ser Trp Ala His Pro
        275                 280                 285 gga agg acc agg ggc cca agc gat agg ggc ttc tgt gtt gtg tca cca     912
```

```
                Gly Arg Thr Arg Gly Pro Ser Asp Arg Gly Phe Cys Val Val Ser Pro
                    290                 295                 300 gcc agg cct gcc gaa gag gct acc tcc ttg gaa gga gcc ctc agt ggc      960
Ala Arg Pro Ala Glu Glu Ala Thr Ser Leu Glu Gly Ala Leu Ser Gly
305                 310                 315                 320 acc agg cat tct cat cca tct gtg ggt agg cag cat cat gcc ggc ccc     1008
Thr Arg His Ser His Pro Ser Val Gly Arg Gln His His Ala Gly Pro
                325                 330                 335 ccc tct aca agc aga cct ccc aga cct tgg gac aca ccc tgc cca cca     1056
Pro Ser Thr Ser Arg Pro Pro Arg Pro Trp Asp Thr Pro Cys Pro Pro
340                 345                 350 gtg tat gcc gag acc aag cac ttt ttg tat tcc agt ggc gat aaa gag     1104
Val Tyr Ala Glu Thr Lys His Phe Leu Tyr Ser Ser Gly Asp Lys Glu
        355                 360                 365 cag ctc cgg ccc tct ttt ctg ctc tca agc ctc cgc ccc tct ctg acc     1152
Gln Leu Arg Pro Ser Phe Leu Leu Ser Ser Leu Arg Pro Ser Leu Thr
370                 375                 380 gga gct cgc agg ctg gtg gag acc atc ttt ctg ggc tca aga cca tgg     1200
Gly Ala Arg Arg Leu Val Glu Thr Ile Phe Leu Gly Ser Arg Pro Trp
385                 390                 395                 400 atg cca ggc acc ccc cgc aga ctg ccc agg ctc ccc cag cgg tac tgg     1248
Met Pro Gly Thr Pro Arg Arg Leu Pro Arg Leu Pro Gln Arg Tyr Trp
                405                 410                 415 cag atg cgc cct ctc ttt ctg gaa ctt ctg ggt aac cac gcc cag tgc     1296
Gln Met Arg Pro Leu Phe Leu Glu Leu Leu Gly Asn His Ala Gln Cys
            420                 425                 430 cca tat ggc gtc ctg ctg aag acc cac tgt cct ctg agg gcc gcc gtg     1344
Pro Tyr Gly Val Leu Leu Lys Thr His Cys Pro Leu Arg Ala Ala Val
        435                 440                 445 acc cca gcc gcc ggt gtg tgt gct aga gaa aaa ccc cag ggc tca gtg     1392
Thr Pro Ala Ala Gly Val Cys Ala Arg Glu Lys Pro Gln Gly Ser Val
450                 455                 460 gct gca cct gaa gag gag gac act gac cct cgc cgc ctt gtc cag ttg     1440
Ala Ala Pro Glu Glu Glu Asp Thr Asp Pro Arg Arg Leu Val Gln Leu
465                 470                 475                 480 ctc agg cag cat tca tca cca tgg cag gtg tac ggc ttc gtg agg gct     1488
Leu Arg Gln His Ser Ser Pro Trp Gln Val Tyr Gly Phe Val Arg Ala
                485                 490                 495 tgc ctg cgg aga ctg gtc ccc ccc gga ttg tgg gga tct cgg cac aac     1536
Cys Leu Arg Arg Leu Val Pro Pro Gly Leu Trp Gly Ser Arg His Asn
            500                 505                 510 gaa cgg cgc ttt ctg agg aat aca aag aag ttt atc tcc ctg ggc aag     1584
Glu Arg Arg Phe Leu Arg Asn Thr Lys Lys Phe Ile Ser Leu Gly Lys
        515                 520                 525 cat gca aag ctc agc ttg cag gag ctg aca tgg aag atg agc gtt aga     1632
His Ala Lys Leu Ser Leu Gln Glu Leu Thr Trp Lys Met Ser Val Arg
530                 535                 540 gga tgc gca tgg ctc agg cgg tca cct gga gtt gga tgc gtt cca gca     1680
Gly Cys Ala Trp Leu Arg Arg Ser Pro Gly Val Gly Cys Val Pro Ala
545                 550                 555                 560 gca gag cac agg ctg cgc gaa gag att ctc gca aag ttc ctg cac tgg     1728
Ala Glu His Arg Leu Arg Glu Glu Ile Leu Ala Lys Phe Leu His Trp
                565                 570                 575 ctt atg agc gtc tac gtg gtc gaa ctg ctg cgg tct ttc ttc tac gtg     1776
Leu Met Ser Val Tyr Val Val Glu Leu Leu Arg Ser Phe Phe Tyr Val
            580                 585                 590 aca gag acc act ttt cag aag aac aga ctg ttc ttc tac agg aag tcc     1824
Thr Glu Thr Thr Phe Gln Lys Asn Arg Leu Phe Phe Tyr Arg Lys Ser
        595                 600                 605
```

-continued

| | | |
|---|---|---|
| gtc tgg agc aag ctc cag agt att ggt att aga cag cac ctt aag aga<br>Val Trp Ser Lys Leu Gln Ser Ile Gly Ile Arg Gln His Leu Lys Arg<br>610                    615                    620 | 1872 | |
| gtt cag ctt aga gag ctg tcc gaa gct gaa gtc cgc cag cac cgc gaa<br>Val Gln Leu Arg Glu Leu Ser Glu Ala Glu Val Arg Gln His Arg Glu<br>625                    630                    635                    640 | 1920 | |
| gct cgc ccc gcc ctc ctg acc tct cgg ctg cgg ttt att ccc aaa ccc<br>Ala Arg Pro Ala Leu Leu Thr Ser Arg Leu Arg Phe Ile Pro Lys Pro<br>                    645                    650                    655 | 1968 | |
| gat ggc ctt aga cct atc gtg aat atg gat tac gtc gtg ggt gcc cgc<br>Asp Gly Leu Arg Pro Ile Val Asn Met Asp Tyr Val Val Gly Ala Arg<br>660                    665                    670 | 2016 | |
| act ttc aga agg gag aag agg gcc gag aga ctg aca tct cgc gtg aag<br>Thr Phe Arg Arg Glu Lys Arg Ala Glu Arg Leu Thr Ser Arg Val Lys<br>                    675                    680                    685 | 2064 | |
| gca ctt ttt tct gtg ctt aat tat gaa aga gcc cgc aga cct ggt ctt<br>Ala Leu Phe Ser Val Leu Asn Tyr Glu Arg Ala Arg Pro Gly Leu<br>690                    695                    700 | 2112 | |
| ctc gga gcc agc gtg ctc ggc ctg gat gat atc cat cgg gct tgg cgc<br>Leu Gly Ala Ser Val Leu Gly Leu Asp Asp Ile His Arg Ala Trp Arg<br>705                    710                    715                    720 | 2160 | |
| acc ttt gtg ctt cgg gtg agg gca cag gat cct cct cct gag ctt tat<br>Thr Phe Val Leu Arg Val Arg Ala Gln Asp Pro Pro Pro Glu Leu Tyr<br>                    725                    730                    735 | 2208 | |
| ttt gtg aaa gtt gat gtt act ggt gct tac gat aca atc cct cag gac<br>Phe Val Lys Val Asp Val Thr Gly Ala Tyr Asp Thr Ile Pro Gln Asp<br>740                    745                    750 | 2256 | |
| cgg ctc acc gag gtg atc gcc tct att atc aaa ccc cag aac acc tac<br>Arg Leu Thr Glu Val Ile Ala Ser Ile Ile Lys Pro Gln Asn Thr Tyr<br>                    755                    760                    765 | 2304 | |
| tgc gtg aga agg tac gcc gtc gtt cag aaa gcc gca cac gga cac gtg<br>Cys Val Arg Arg Tyr Ala Val Val Gln Lys Ala Ala His Gly His Val<br>770                    775                    780 | 2352 | |
| cgc aaa gct ttc aaa tcc cac gtg tct acc ttg aca gac ctc cag cct<br>Arg Lys Ala Phe Lys Ser His Val Ser Thr Leu Thr Asp Leu Gln Pro<br>785                    790                    795                    800 | 2400 | |
| tat atg cgg cag ttt gtc gca cac ctg cag gag act agc ccc ttg agg<br>Tyr Met Arg Gln Phe Val Ala His Leu Gln Glu Thr Ser Pro Leu Arg<br>                    805                    810                    815 | 2448 | |
| gac gct gtg gtc atc gaa cag tcc agc tct ctc aat gag gca tcc tca<br>Asp Ala Val Val Ile Glu Gln Ser Ser Ser Leu Asn Glu Ala Ser Ser<br>820                    825                    830 | 2496 | |
| ggc ctg ttt gat gtg ttc ctg cgc ttt atg tgc cac cac gcc gtg cgg<br>Gly Leu Phe Asp Val Phe Leu Arg Phe Met Cys His His Ala Val Arg<br>                    835                    840                    845 | 2544 | |
| att agg ggc aag tct tac gtg cag tgc cag ggc atc cca cag ggt agc<br>Ile Arg Gly Lys Ser Tyr Val Gln Cys Gln Gly Ile Pro Gln Gly Ser<br>850                    855                    860 | 2592 | |
| atc ctg agc aca ctg ctg tgt agc ctg tgc tat ggc gat atg gag aat<br>Ile Leu Ser Thr Leu Leu Cys Ser Leu Cys Tyr Gly Asp Met Glu Asn<br>865                    870                    875                    880 | 2640 | |
| aaa ttg ttc gcc ggt atc aga aga gac ggt ttg ctc ctg agg ctg ttc<br>Lys Leu Phe Ala Gly Ile Arg Arg Asp Gly Leu Leu Leu Arg Leu Phe<br>                    885                    890                    895 | 2688 | |
| ctg ctg gtt acc ccc cat ctg act cat gcc aaa aca ttt ttg cgg act<br>Leu Leu Val Thr Pro His Leu Thr His Ala Lys Thr Phe Leu Arg Thr<br>900                    905                    910 | 2736 | |
| ctg gtt agg ggc gtg cca gag tat ggc tgt gtt gtg aat ttg cgg aaa<br>Leu Val Arg Gly Val Pro Glu Tyr Gly Cys Val Val Asn Leu Arg Lys<br>                    915                    920                    925 | 2784 | |

```
act gtg gtt aat ttc cca gtg gag gac gaa gct ctc gga ggc aca gct       2832
Thr Val Val Asn Phe Pro Val Glu Asp Glu Ala Leu Gly Gly Thr Ala
    930                 935                 940 ttt gtt cag atg cct gcc cac ggc ctg ttc cca tgg tgc gga ctg ctg       2880
Phe Val Gln Met Pro Ala His Gly Leu Phe Pro Trp Cys Gly Leu Leu
945                 950                 955                 960 ctc gat acc cgg acc ctc gag gtg cag tcc gat tat agt tcc tat gca       2928
Leu Asp Thr Arg Thr Leu Glu Val Gln Ser Asp Tyr Ser Ser Tyr Ala
                965                 970                 975 aga aca tca att cgg gct agc ctg act ttc aac agg ggc ttc aag gcc       2976
Arg Thr Ser Ile Arg Ala Ser Leu Thr Phe Asn Arg Gly Phe Lys Ala
            980                 985                 990 ggc cgg aat atg aga agg aaa ctg ttc gga gtg ttg aga ctt aag tgt       3024
Gly Arg Asn Met Arg Arg Lys Leu Phe Gly Val Leu Arg Leu Lys Cys
        995                1000                1005 cat agt ctt ttt ttg gac ttg cag gtc aat tct ctc cag aca gtg           3069
His Ser Leu Phe Leu Asp Leu Gln Val Asn Ser Leu Gln Thr Val
    1010                1015                1020 tgt acc aac att tat aaa atc ctc ttg ctg cag gct tac aga ttc           3114
Cys Thr Asn Ile Tyr Lys Ile Leu Leu Leu Gln Ala Tyr Arg Phe
1025                1030                1035 cat gcc tgc gtc ctg cag ctg cct ttc cac cag cag gtg tgg aaa           3159
His Ala Cys Val Leu Gln Leu Pro Phe His Gln Gln Val Trp Lys
    1040                1045                1050 aac cct acc ttc ttc ctg cgg gtg att agc gac acc gcc agt ctt           3204
Asn Pro Thr Phe Phe Leu Arg Val Ile Ser Asp Thr Ala Ser Leu
1055                1060                1065 tgc tac tcc atc ttg aaa gca aaa aac gct ggc atg agc ttg gga           3249
Cys Tyr Ser Ile Leu Lys Ala Lys Asn Ala Gly Met Ser Leu Gly
    1070                1075                1080 gct aag ggc gcc gct gga cct ctg ccc agt gaa gca gtc cag tgg           3294
Ala Lys Gly Ala Ala Gly Pro Leu Pro Ser Glu Ala Val Gln Trp
1085                1090                1095 ctg tgt cat cag gct ttc ctc ctt aaa ctg aca cgc cac cgc gtg           3339
Leu Cys His Gln Ala Phe Leu Leu Lys Leu Thr Arg His Arg Val
    1100                1105                1110 act tac gtc cca ctc ctg ggc tcc ctg aga act gct cag acc cag           3384
Thr Tyr Val Pro Leu Leu Gly Ser Leu Arg Thr Ala Gln Thr Gln
1115                1120                1125 ctt tcc cgg aag ctt cca ggc act acc ctt acc gca ctc gaa gca           3429
Leu Ser Arg Lys Leu Pro Gly Thr Thr Leu Thr Ala Leu Glu Ala
    1130                1135                1140 gcc gcc aac cct gcc ctg ccc tcc gac ttt aag act atc ctg gac           3474
Ala Ala Asn Pro Ala Leu Pro Ser Asp Phe Lys Thr Ile Leu Asp
1145                1150                1155
```

<210> SEQ ID NO 15
<211> LENGTH: 1158
<212> TYPE: PRT
<213> ORGANISM: Artificial Sequence
<220> FEATURE:
<223> OTHER INFORMATION: Synthetic Construct

<400> SEQUENCE: 15

```
Met Gln Ile Phe Val Lys Thr Leu Thr Gly Lys Thr Ile Thr Leu Glu
1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Arg Ala Leu Val
 65                  70                  75                  80

Ala Gln Cys Leu Val Cys Val Pro Trp Asp Ala Arg Pro Pro Ala
                 85                  90                  95

Ala Pro Ser Phe Arg Gln Val Ser Cys Leu Lys Glu Leu Val Ala Arg
                100                 105                 110

Val Leu Gln Arg Leu Cys Glu Arg Gly Ala Lys Asn Val Leu Ala Phe
            115                 120                 125

Gly Phe Ala Leu Leu Asp Gly Ala Arg Gly Gly Pro Pro Glu Ala Phe
            130                 135                 140

Thr Thr Ser Val Arg Ser Tyr Leu Pro Asn Thr Val Thr Asp Ala Leu
145                 150                 155                 160

Arg Gly Ser Gly Ala Trp Gly Leu Leu Leu Arg Arg Val Gly Asp Asp
                165                 170                 175

Val Leu Val His Leu Leu Ala Arg Cys Ala Leu Phe Val Leu Val Ala
            180                 185                 190

Pro Ser Cys Ala Tyr Gln Val Cys Gly Pro Pro Leu Tyr Gln Leu Gly
            195                 200                 205

Ala Ala Thr Gln Ala Arg Pro Pro His Ala Ser Gly Pro Arg Arg
210                 215                 220

Arg Leu Gly Cys Glu Arg Ala Trp Asn His Ser Val Arg Glu Ala Gly
225                 230                 235                 240

Val Pro Leu Gly Leu Pro Ala Pro Gly Ala Arg Arg Arg Gly Gly Ser
                245                 250                 255

Ala Ser Arg Ser Leu Pro Leu Pro Lys Arg Pro Arg Arg Gly Ala Ala
            260                 265                 270

Pro Glu Pro Glu Arg Thr Pro Val Gly Gln Gly Ser Trp Ala His Pro
            275                 280                 285

Gly Arg Thr Arg Gly Pro Ser Asp Arg Gly Phe Cys Val Val Ser Pro
            290                 295                 300

Ala Arg Pro Ala Glu Glu Ala Thr Ser Leu Glu Gly Ala Leu Ser Gly
305                 310                 315                 320

Thr Arg His Ser His Pro Ser Val Gly Arg Gln His His Ala Gly Pro
                325                 330                 335

Pro Ser Thr Ser Arg Pro Pro Arg Pro Trp Asp Thr Pro Cys Pro Pro
            340                 345                 350

Val Tyr Ala Glu Thr Lys His Phe Leu Tyr Ser Ser Gly Asp Lys Glu
            355                 360                 365

Gln Leu Arg Pro Ser Phe Leu Leu Ser Ser Leu Arg Pro Ser Leu Thr
            370                 375                 380

Gly Ala Arg Arg Leu Val Glu Thr Ile Phe Leu Gly Ser Arg Pro Trp
385                 390                 395                 400

Met Pro Gly Thr Pro Arg Arg Leu Pro Arg Leu Pro Gln Arg Tyr Trp
                405                 410                 415

Gln Met Arg Pro Leu Phe Leu Glu Leu Leu Gly Asn His Ala Gln Cys
            420                 425                 430

Pro Tyr Gly Val Leu Leu Lys Thr His Cys Pro Leu Arg Ala Ala Val
            435                 440                 445

Thr Pro Ala Ala Gly Val Cys Ala Arg Glu Lys Pro Gln Gly Ser Val
450                 455                 460
```

```
Ala Ala Pro Glu Glu Glu Asp Thr Asp Pro Arg Arg Leu Val Gln Leu
465                 470                 475                 480

Leu Arg Gln His Ser Ser Pro Trp Gln Val Tyr Gly Phe Val Arg Ala
            485                 490                 495

Cys Leu Arg Arg Leu Val Pro Pro Gly Leu Trp Gly Ser Arg His Asn
                500                 505                 510

Glu Arg Arg Phe Leu Arg Asn Thr Lys Lys Phe Ile Ser Leu Gly Lys
            515                 520                 525

His Ala Lys Leu Ser Leu Gln Glu Leu Thr Trp Lys Met Ser Val Arg
            530                 535                 540

Gly Cys Ala Trp Leu Arg Arg Ser Pro Gly Val Gly Cys Val Pro Ala
545                 550                 555                 560

Ala Glu His Arg Leu Arg Glu Glu Ile Leu Ala Lys Phe Leu His Trp
                565                 570                 575

Leu Met Ser Val Tyr Val Val Glu Leu Leu Arg Ser Phe Phe Tyr Val
                580                 585                 590

Thr Glu Thr Thr Phe Gln Lys Asn Arg Leu Phe Phe Tyr Arg Lys Ser
            595                 600                 605

Val Trp Ser Lys Leu Gln Ser Ile Gly Ile Arg Gln His Leu Lys Arg
            610                 615                 620

Val Gln Leu Arg Glu Leu Ser Glu Ala Glu Val Arg Gln His Arg Glu
625                 630                 635                 640

Ala Arg Pro Ala Leu Leu Thr Ser Arg Leu Arg Phe Ile Pro Lys Pro
                645                 650                 655

Asp Gly Leu Arg Pro Ile Val Asn Met Asp Tyr Val Val Gly Ala Arg
            660                 665                 670

Thr Phe Arg Arg Glu Lys Arg Ala Glu Arg Leu Thr Ser Arg Val Lys
            675                 680                 685

Ala Leu Phe Ser Val Leu Asn Tyr Glu Arg Ala Arg Arg Pro Gly Leu
            690                 695                 700

Leu Gly Ala Ser Val Leu Gly Leu Asp Asp Ile His Arg Ala Trp Arg
705                 710                 715                 720

Thr Phe Val Leu Arg Val Arg Ala Gln Asp Pro Pro Pro Glu Leu Tyr
                725                 730                 735

Phe Val Lys Val Asp Val Thr Gly Ala Tyr Asp Thr Ile Pro Gln Asp
                740                 745                 750

Arg Leu Thr Glu Val Ile Ala Ser Ile Ile Lys Pro Gln Asn Thr Tyr
            755                 760                 765

Cys Val Arg Arg Tyr Ala Val Val Gln Lys Ala Ala His Gly His Val
770                 775                 780

Arg Lys Ala Phe Lys Ser His Val Ser Thr Leu Thr Asp Leu Gln Pro
785                 790                 795                 800

Tyr Met Arg Gln Phe Val Ala His Leu Gln Glu Thr Ser Pro Leu Arg
            805                 810                 815

Asp Ala Val Val Ile Glu Gln Ser Ser Ser Leu Asn Glu Ala Ser Ser
            820                 825                 830

Gly Leu Phe Asp Val Phe Leu Arg Phe Met Cys His His Ala Val Arg
            835                 840                 845

Ile Arg Gly Lys Ser Tyr Val Gln Cys Gln Gly Ile Pro Gln Gly Ser
            850                 855                 860

Ile Leu Ser Thr Leu Leu Cys Ser Leu Cys Tyr Gly Asp Met Glu Asn
865                 870                 875                 880

Lys Leu Phe Ala Gly Ile Arg Arg Asp Gly Leu Leu Leu Arg Leu Phe
```

885                 890                 895

Leu Leu Val Thr Pro His Leu Thr His Ala Lys Thr Phe Leu Arg Thr
            900                 905                 910

Leu Val Arg Gly Val Pro Glu Tyr Gly Cys Val Val Asn Leu Arg Lys
        915                 920                 925

Thr Val Val Asn Phe Pro Val Glu Asp Glu Ala Leu Gly Gly Thr Ala
    930                 935                 940

Phe Val Gln Met Pro Ala His Gly Leu Phe Pro Trp Cys Gly Leu Leu
945                 950                 955                 960

Leu Asp Thr Arg Thr Leu Glu Val Gln Ser Asp Tyr Ser Ser Tyr Ala
            965                 970                 975

Arg Thr Ser Ile Arg Ala Ser Leu Thr Phe Asn Arg Gly Phe Lys Ala
        980                 985                 990

Gly Arg Asn Met Arg Arg Lys Leu Phe Gly Val Leu Arg Leu Lys Cys
    995                 1000                1005

His Ser Leu Phe Leu Asp Leu Gln Val Asn Ser Leu Gln Thr Val
    1010                1015                1020

Cys Thr Asn Ile Tyr Lys Ile Leu Leu Leu Gln Ala Tyr Arg Phe
    1025                1030                1035

His Ala Cys Val Leu Gln Leu Pro Phe His Gln Gln Val Trp Lys
    1040                1045                1050

Asn Pro Thr Phe Phe Leu Arg Val Ile Ser Asp Thr Ala Ser Leu
    1055                1060                1065

Cys Tyr Ser Ile Leu Lys Ala Lys Asn Ala Gly Met Ser Leu Gly
    1070                1075                1080

Ala Lys Gly Ala Ala Gly Pro Leu Pro Ser Glu Ala Val Gln Trp
    1085                1090                1095

Leu Cys His Gln Ala Phe Leu Leu Lys Leu Thr Arg His Arg Val
    1100                1105                1110

Thr Tyr Val Pro Leu Leu Gly Ser Leu Arg Thr Ala Gln Thr Gln
    1115                1120                1125

Leu Ser Arg Lys Leu Pro Gly Thr Thr Leu Thr Ala Leu Glu Ala
    1130                1135                1140

Ala Ala Asn Pro Ala Leu Pro Ser Asp Phe Lys Thr Ile Leu Asp
    1145                1150                1155

<210> SEQ ID NO 16
<211> LENGTH: 9
<212> TYPE: PRT
<213> ORGANISM: Homo sapiens

<400> SEQUENCE: 16

Ile Leu Ala Lys Phe Leu His Trp Leu
1               5

<210> SEQ ID NO 17
<211> LENGTH: 9
<212> TYPE: PRT
<213> ORGANISM: Homo sapiens

<400> SEQUENCE: 17

Tyr Leu Phe Phe Tyr Arg Lys Ser Val
1               5

<210> SEQ ID NO 18
<211> LENGTH: 10
<212> TYPE: PRT

<213> ORGANISM: Homo sapiens

<400> SEQUENCE: 18

Tyr Leu Gln Val Asn Ser Leu Gln Thr Val
1               5                   10

<210> SEQ ID NO 19
<211> LENGTH: 9
<212> TYPE: PRT
<213> ORGANISM: Homo sapiens

<400> SEQUENCE: 19

Ser Val Trp Ser Lys Leu Gln Ser Ile
1               5

<210> SEQ ID NO 20
<211> LENGTH: 9
<212> TYPE: PRT
<213> ORGANISM: Homo sapiens

<400> SEQUENCE: 20

Ser Leu Cys Tyr Ser Ile Leu Lys Ala
1               5

<210> SEQ ID NO 21
<211> LENGTH: 9
<212> TYPE: PRT
<213> ORGANISM: Homo sapiens

<400> SEQUENCE: 21

His Ala Gln Cys Pro Tyr Gly Val Leu
1               5

<210> SEQ ID NO 22
<211> LENGTH: 10
<212> TYPE: PRT
<213> ORGANISM: Homo sapiens

<400> SEQUENCE: 22

Gln Ala Tyr Arg Phe His Ala Cys Val Leu
1               5                   10

<210> SEQ ID NO 23
<211> LENGTH: 9
<212> TYPE: PRT
<213> ORGANISM: Homo sapiens

<400> SEQUENCE: 23

Arg Pro Ile Val Asn Met Asp Tyr Val
1               5

<210> SEQ ID NO 24
<211> LENGTH: 10
<212> TYPE: PRT
<213> ORGANISM: Homo sapiens

<400> SEQUENCE: 24

Gln Thr Val Cys Thr Asn Ile Tyr Lys Ile
1               5                   10

<210> SEQ ID NO 25
<211> LENGTH: 15
<212> TYPE: PRT
<213> ORGANISM: Homo sapiens

```
<400> SEQUENCE: 25

Val Cys Val Pro Trp Asp Ala Arg Pro Pro Ala Ala Pro Ser
1               5                   10                  15

<210> SEQ ID NO 26
<211> LENGTH: 15
<212> TYPE: PRT
<213> ORGANISM: Homo sapiens

<400> SEQUENCE: 26

Cys Val Pro Trp Asp Ala Arg Pro Pro Ala Ala Pro Ser Phe
1               5                   10                  15

<210> SEQ ID NO 27
<211> LENGTH: 15
<212> TYPE: PRT
<213> ORGANISM: Homo sapiens

<400> SEQUENCE: 27

Val Pro Trp Asp Ala Arg Pro Pro Ala Ala Pro Ser Phe Arg
1               5                   10                  15

<210> SEQ ID NO 28
<211> LENGTH: 15
<212> TYPE: PRT
<213> ORGANISM: Homo sapiens

<400> SEQUENCE: 28

Gly Arg Gln His His Ala Gly Pro Pro Ser Thr Ser Arg Pro Pro
1               5                   10                  15

<210> SEQ ID NO 29
<211> LENGTH: 15
<212> TYPE: PRT
<213> ORGANISM: Homo sapiens

<400> SEQUENCE: 29

Met Ser Leu Gly Ala Lys Gly Ala Ala Gly Pro Leu Pro Ser Glu
1               5                   10                  15

<210> SEQ ID NO 30
<211> LENGTH: 15
<212> TYPE: PRT
<213> ORGANISM: Homo sapiens

<400> SEQUENCE: 30

Leu Gly Ala Lys Gly Ala Ala Gly Pro Leu Pro Ser Glu Ala Val
1               5                   10                  15

<210> SEQ ID NO 31
<211> LENGTH: 15
<212> TYPE: PRT
<213> ORGANISM: Homo sapiens

<400> SEQUENCE: 31

Thr Leu Thr Ala Leu Glu Ala Ala Ala Asn Pro Ala Leu Pro Ser
1               5                   10                  15
```

```
<210> SEQ ID NO 32
<211> LENGTH: 15
<212> TYPE: PRT
<213> ORGANISM: Homo sapiens

<400> SEQUENCE: 32

Leu Thr Ala Leu Glu Ala Ala Ala Asn Pro Ala Leu Pro Ser Asp
1               5                   10                  15
```

RECOMBINANT MEASLES VACCINE EXPRESSING HTERT

CROSS-REFERENCE TO RELATED APPLICATIONS

This application is a National Stage of International Application No. PCT/EP2018/061733, filed May 7, 2018, which claims priority to European Application No. 17305522.9, filed May 9, 2017, all of which applications are herein incorporated by reference in their entireties.

SEQUENCE LISTING

The instant application contains a Sequence Listing which has been submitted electronically in ASCII format and is hereby incorporated by reference in its entirety. Said ASCII copy, created on Oct. 29, 2019, is named PCTEP2018061733_246393_000015_SL.txt and is 208 bytes in size.

The invention relates to a recombinant measles virus plasmid capable of expressing a human telomerase reverse transcriptase (hTERT) protein. The invention further relates to a vaccine comprising said plasmid or particles rescued therefrom, and uses thereof, especially in preventing or treating a tumor in a patient.

BACKGROUND OF THE INVENTION

The stimulation of tumor-specific T-cell responses with active immunotherapy has several theoretical advantages over other forms of cancer treatment. In order to obtain clinical benefits T-cell-based immunotherapy must stimulate both CD8 and CD4 tumor-reactive Tcell responses which recognize tumor specific antigens. To date, a wide range of tumor antigens have been identified and characterized. However, heterogeneous expression of most of these tumor antigens among different cancer types limits the broad applicability of cancer vaccines that target them. Considering these hurdles, different properties such as therapeutic function, immunogenicity and specificity have been proposed in order to determine an ideal tumor associated antigen (TAAs) (Cheever et al, 2009). During the past few years, human telomerase reverse transcriptase (hTERT) has emerged as the first bona fide common tumor antigen and is actively investigated as a universal target for cancer immunotherapy. Human TERT is the rate-limiting catalytic subunit of the telomerase complex that synthesizes telomeric DNA or telomers at chromosome ends (Collins and Mitchell, 2002). hTERT is overexpressed in most human tumors (>85%) regardless of their origin and is associated with a poor prognosis (Shay and Bacchetti, 1997; Zhu et al., 2006). Telomerase activation has become one of the most important tumor escape mechanisms to circumvent telomere-dependent pathways of cell death. It is well established that therapeutic strategies targeting antigens not involved in tumor growth can result in the selection of antigen-loss tumor mutants that are clinically progressive (Kim et al., 2007). Any down-regulation or loss of telomerase activity will severely impact the growth potential of the tumor cells; hence is almost never down regulated in tumor cells. Moreover, telomerase is relatively specific to cancer cells as normal body cells express little or no telomerase for most of their lifespan and generally have longer telomeres than those in tumor cells. The crucial role of hTERT in oncogenesis justifies its use in clinical immunotherapy as a treatment for cancer.

Nowadays, different clinical approaches have been explored based on major histocompatibility (MHC) class I or II restricted hTERT peptides, autologous antigen-presenting cells (APCs; dendritic cells or B lymphocytes) loaded with hTERT peptides or transduced with hTERT mRNA (Harley, 2008).

International patent application WO2015/063117 further describes a DNA vaccine construct encoding hTERT.

However there is still a need for further vaccine strategies, which would provide a rapid and strong response.

SUMMARY OF THE INVENTION

The inventors have now developed a recombinant measles virus (MV) vaccine strategy which does not show the drawbacks of peptide (even long peptide) vaccination, restricted to certain epitopes of hTERT, and which is more immunogenic than a peptide or even DNA.

This MV vaccine induces both CD8 cytotoxic T-cells (CTLs) and CD4 helper T-cells independently of the HLA-restriction of the patient, while being safe and inducing a better quantitative and qualitative immune response.

A first object of the invention is a recombinant cDNA molecule that encodes the full-length, infectious, antigenomic (+)RNA strand of a measles virus (MV), which cDNA molecule further comprises an Additional Transcription Unit (ATU) that contains a heterologous DNA sequence capable of expressing a heterologous amino acid sequence, wherein said heterologous amino acid sequence is a human telomerase reverse transcriptase (hTERT) protein which is devoid of telomerase catalytic activity and of a nucleolar localization signal, and wherein the hTERT protein is fused at N-terminus with a protein enhancing addressing of the hTERT protein to proteasome.

The invention more particularly provides a recombinant measles virus plasmid comprising said cDNA molecule.

In a particular embodiment, the sequence that encodes the hTERT protein contains a mutation that provides inactivation of the catalytic activity of the TERT protein, preferably wherein the hTERT protein is devoid of telomerase catalytic activity by deletion of at least one amino acid, still preferably wherein the hTERT protein is devoid of telomerase catalytic activity by deletion of amino acids 867-869 (VDD) of hTERT.

Preferably the hTERT protein is devoid of telomerase catalytic activity by a further deletion of 1 to 12 amino acids upstream and/or downstream amino acids 867-869 (VDD).

In a preferred embodiment, the hTERT protein is devoid of a nucleolar localization signal by deletion of at least amino acids 1-23, preferably by deletion of amino acids 1-47.

The protein enhancing addressing of the hTERT protein to proteasome is ubiquitin, or is a chaperon protein, such as calreticulin.

The Additional Transcription Unit is preferably located between the P and M genes of the measles virus.

In a particular embodiment, said cDNA molecule is placed under the control of a heterologous expression control sequence appropriate for the transcription of the antigenomic (+)RNA strand starting from the cDNA molecule, wherein the heterologous expression control sequence of said cDNA preferably comprises the T7 promoter and T7 terminator sequences.

In a particular embodiment, the cDNA molecule further comprises, at its 5'-end, adjacent to the first nucleotide of the nucleotide sequence encoding the full length, infectious antigenomic (+) RNA strand of the MV, a GGG motif followed by a hammerhead ribozyme sequence and which comprises, at its 3'-end, adjacent to the last nucleotide of said nucleotide sequence encoding the full length, infectious anti-genomic (+)RNA strand, the sequence of a hepatitis delta virus ribozyme.

Another subject of the invention is an immunogenic or vaccine composition whose active principle comprises measles viral particles rescued from the plasmid as defined herein, in a helper-cell-based rescue system.

The immunogenic or vaccine composition or the plasmid is useful in triggering an immune response in a subject, against cells that overexpress telomerase, preferably dysplasia cells, tumor cells, or cells infected by an oncovirus. The vaccine composition or the plasmid is particularly useful in preventing or treating a tumor in a patient.

LEGENDS TO THE FIGURES

Figures 1A, 1B:
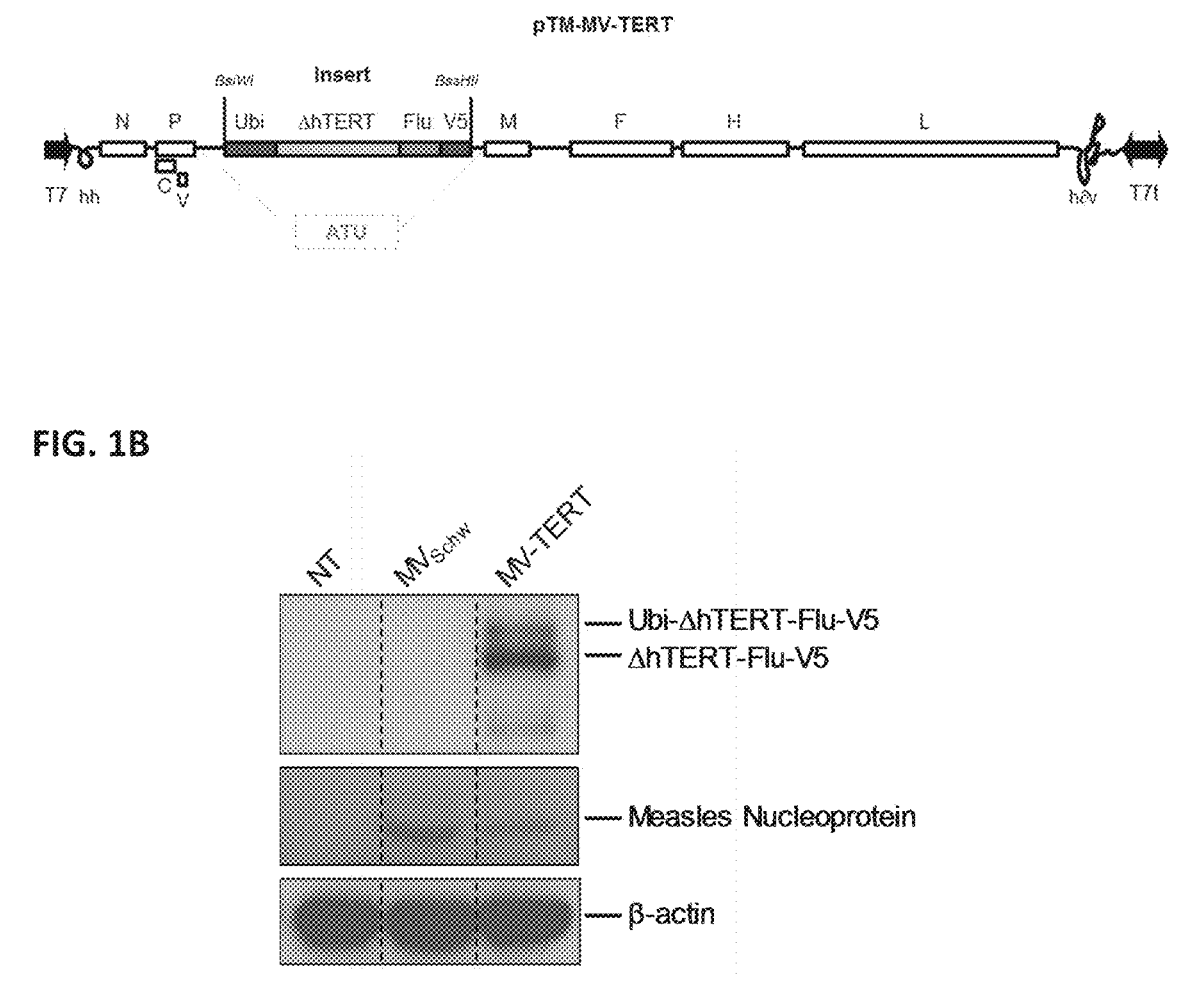

FIG. 1 Genetic maps of the pTM-MV-TERT plasmid and expression of ubiquitin-ΔhTERT-Flu-V5 protein (A) pTM-MV-TERT vector contains an ATU in which is inserted an ubiquitin-ΔhTERT-Flu HLA A*0201 epitope-V5 fused protein nucleotide sequence. An ATU represents a multiple cloning site cassette inserted into a copy of the N-P intergenic region of the viral genome. The transgene ubiquitin-ΔhTERT-Flu HLA A*0201 epitope-V5 was introduced into the ATU using BsiWI and BssHII cloning sites. Then, pTM-MVSchw-ATU2 was used to introduce an ATU, containing this hTERT transgene, between the P and M genes using SalI site in position 3446. The reverse genetics procedure to obtain the pTM-MVSchw and ATU and recombinant derivatives was previously described (Combredet et al., 2003a; Radecke and Billeter, 1997; Radecke et al., 1995).

The MV genes are indicated as follows: N, nucleoprotein; P, phosphoprotein including C and V proteins; M, matrix; F, fusion; H, hemagglutinin; L, polymerase. T7, T7 RNA polymerase promoter; hh, hammer-head ribozyme; h∂v, hepatitis delta virus ribozyme; T7t, T7 RNA polymerase terminator.

| Location (bases) | Sequence |
|---|---|
| 1-3445 | pTM-MVSchw |
| 3446-3451 | SalI restriction site: G.TCGAC |
| 3452-3525 | ATU with MVSchwarz N-P intergenic region containing cis-acting sequence |
| 3526-3531 | BsiWI restriction site: C.GTACG |
| 3532-7107 | Ubi-ΔhTERT- Flu HLA A*0201 epitope-V5 tag transgene |
| 7108-7113 | BssHII restriction site: G.CGCGC |
| 7114-10034 | ATU with MVSchwarz antigenome containing M CDS, M-F intergenic region and part of FCDS |
| 10035-10040 | SalI restriction site: G.TCGAC |
| 10041-22649 | pTM-MVSchw |

Vector Features
Complete nucleotide sequence of pTM-MV-TERT plasmid: 1-22649
(SEQ ID NO: 3)

| Location (bases) | Sequence | Protein sequence |
|---|---|---|
| 1-8 | NotI restriction site: GC.GGCCGC | |
| 9-28 | T7 promoter | |
| 29-82 | Hammer head ribozyme | |
| 2911-2922 and 13700-13711 | FactorXa site | |
| 3477-3489 and 7157-7169 | Cis-acting element | |
| 83-3445 and 10041-19658 | MV Schwarz antigenome | |
| 190-1767 | N protein nucleotidique sequence | SEQ ID NO: 4 |
| 1889-3412 | P protein nucleotidique sequence | SEQ ID NO: 5 |
| 3535-3762 | Human ubiquitin | SEQ ID NO: 6 |
| 3763-7008 | ΔhTERT | SEQ ID NO: 7 |
| 7009-7062 | Flu HLA-A*0201 | SEQ ID NO: 8 |
| 7063-7107 | V5 tag | SEQ ID NO: 9 |
| 7202-8209 | M protein nucleotidique sequence | SEQ ID NO: 10 |
| 9213-10874 | F protein nucleotidique sequence | SEQ ID NO: 11 |
| 11035-12888 | H protein nucleotidique sequence | SEQ ID NO: 12 |
| 12998-19549 | L protein nucleotidique sequence | SEQ ID NO: 13 |
| 19659-19742 | Hepatitis delta virus (HDV) ribozyme | |
| 19813-19859 | T7 terminator | |

(B) Western blot analysis of pTM-MV-TERT transgene. MV-TERT, MVSchw infected Vero cells or left untreated (NT) were harvested 48 h after infection. Seventy micrograms of total protein from cell lysates were loaded per lane. Ubiquitin-ΔhTERT-Flu-V5 protein, MV nucleoprotein and β-actin were detected using respectively an anti-V5, an anti-nucleoprotein (N) and an anti-β actin mouse monoclonal antibodies. β-actin protein detection was used as a loading control assessment. Detection of MV nucleoprotein required a longer exposure time than the two others proteins.

FIG. 2 Induction of hTERT specific CD8 and CD4 T-cells secreting IFN-γ in response to MV-TERT immunization (A) Six to seven week old IFNAR/CD46 mice were immunized IP with $10^5$ TCID50 of MV-TERT (12 mice) or MVSchw (8 mice). Mouse spleens were harvested 7 or 14 days after vaccination (6 MV-TERT mice/day and 4MVSchw mice/day). MV and hTERT CD8 specific T-cell responses were evaluated by IFN-γ ELIspot assay on Ficoll purified splenocytes stimulated with MV or a pool of 4 hTERT specific peptides restricted to H2-K/Db. (B) Sixteen week old IFNAR/CD46 mice were inoculated IP with $10^5$ TCID50 of MV-TERT or MVSchw (3 mice/group). At day 7, MV and hTERT CD8/CD4 specific T-cell responses were evaluated by IFN-γ ELIspot assay on Ficoll purified splenocytes stimulated either with MV, pool of 4 H2-K/Db restricted hTERT peptides or 8 individual H2-IAb restricted hTERT peptides. (C) Eight week-old HHD/IFNAR/CD46 mice were immunized IP with $10^5$ TCID50 of MV-TERT (6 mice) or MVSchw (4 mice). At day 7, mice spleens were harvested. After one week of in vitro stimulation with a mix of hTERT specific peptides restricted to HLA-A*0201 on Ficoll-purified-splenocytes collected, IFN-γ ELIspot assay was performed using the same peptides. For both experiments, MV specific T-cell stimulation was used as immunization control. MV specific T-cells or hTERT specific CD8 or CD4 T-cells/200,000 splenocytes for MV-TERT vaccine (grey bars) and MVSchw (white bars) are represented as mean±SD. Mann Whitney non parametric test against mice control (MVSchw), **$p<0.01$.

Figure 3A:
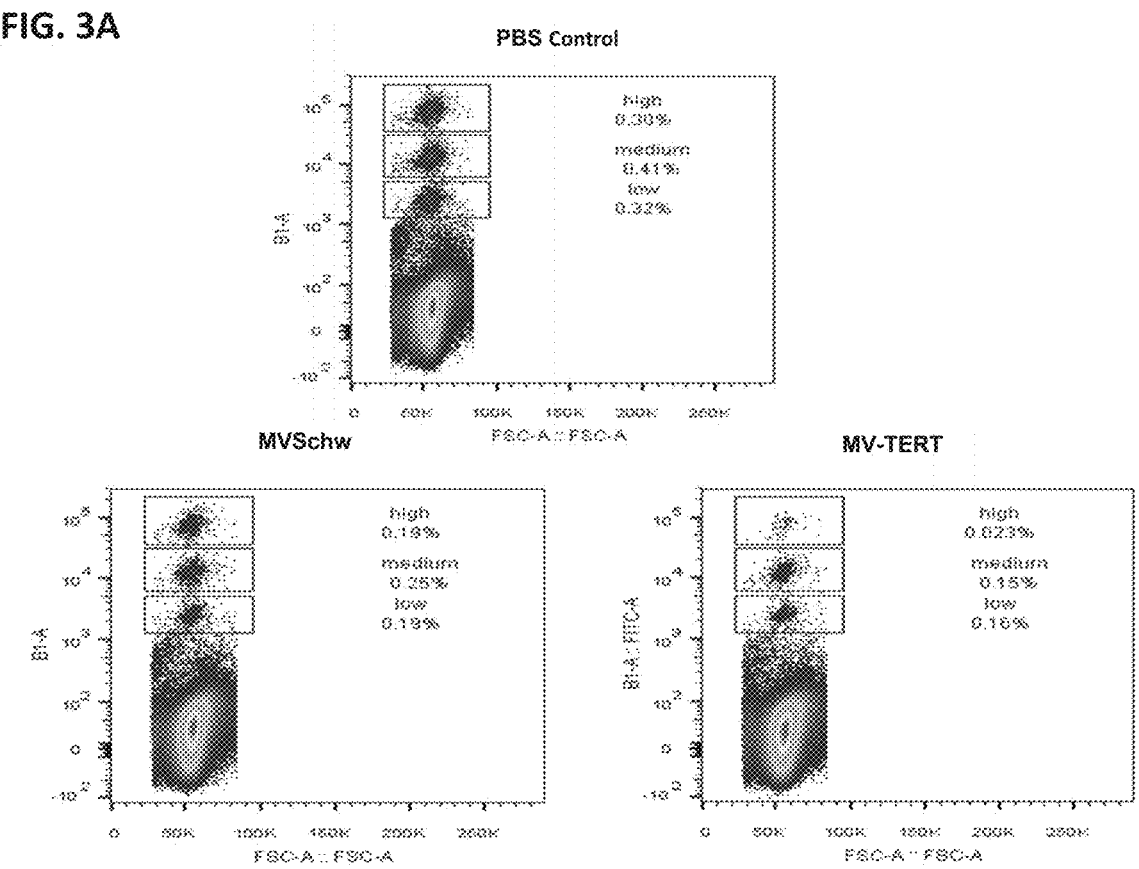
Figure 3B:
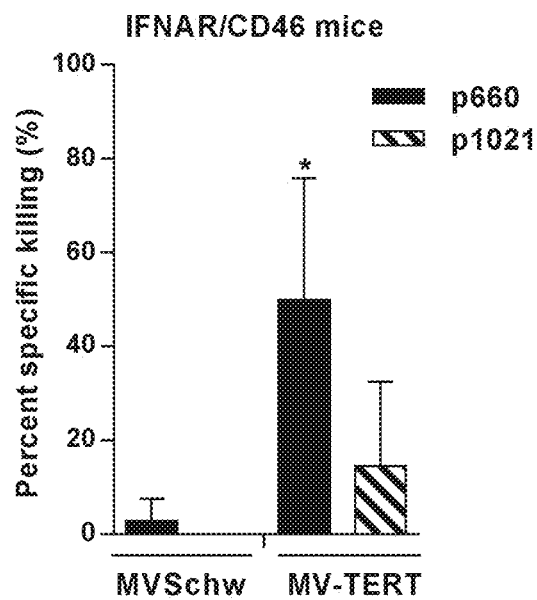

FIG. 3 MV-TERT immunization induced hTERT specific cytotoxic T-cells (A) IFNAR/CD46 mice (7 to 8-week-old) were immunized IP either with $10^5$ TCID50 of MV-TERT or MVSchw or PBS using as a real basal control. At D7, syngeneic splenocytes, pulsed or not with individual hTERT peptides restricted to the H2-Kb/Db (either p660 or p1021) were labeled with CFSE at three different concentrations. Mix of cells was injected IV to immunized mice. After 15-18 hours, the disappearance of peptide pulsed cells in spleens was analyzed by flow cytometry. (B) Percent of killing for p660 (black bars) and p1021 (hatched bars) was calculated using cytometry data and was presented as mean±SD (MV-TERT n=6 and MVSchw n=4 mice). Mann Whitney non parametric test against mice control (MVSchw), $*p<0.05$.

FIG. 4 Evaluation of antibody responses in mice immunized with MV-TERT

IFNAR/CD46 and HHD/IFNAR/CD46 mice were injected IP with $10^5$ TCID50 (D0) and $8 \times 10^4$ TCID50 (D28) of MVSchw and MV-TERT at 1 month of interval (IFNAR/CD46 MVSchw n=3, MV-TERT n=5; HHD/IFNAR/CD46 MVSchw n=4, MV-TERT n=6). (A and B) Anti-MV antibody titers were determined by ELISA on sera collected before immunization (D0) and one month after the last immunization (D28 and D49). Results are expressed as mean antibody titers SD determined in serial dilutions of sera. Mann Whitney non parametric test against mice control (MVSchw) was performed for each day. (C and D) Detection of anti-hTERT antibodies was performed according a validated qualitative ELISA immunoassay. Results are expressed as mean ratio (R)±SD where R=OD values/cut off point; cut off point=normalized cut off×mean of eight determination of the negative pool of matrices. Positive or negative results were obtained according the Quality Controls (QC) ratio. IFNAR/CD46: R QC high=7.27-7.67; R QC low=1.46-1.50; cut-off=0.252. HHD/IFNAR/CD46: R QC high=8.30-8.99; R QC low=1.43-1.44; cut-off=0.279. Mann Whitney non parametric test against mice control (MVSchw) was performed for each day.

FIG. 5 Heterologous prime-boost regimen with DNA encoding hTERT followed by MV-TERT immunization induced different patterns of T-cell responses (A and B) Ten IFNAR/CD46 mice (7 to 8 week-old) were immunized ID with 25 μg of DNA coding for Ubi-ΔhTERT fusion protein at day 0. Twenty one days later, mice received an IP boost injection with $10^5$ TCID50 of MV-TERT (6/10 mice) or MVSchw (4/10 mice). (A) Peripheral blood was collected before the first immunization day 0, at day 7, 14, and 21 post-priming and at day 7 post-boost (D28). PBMCs were Ficoll-purified and stimulated with a pool of 4 hTERT specific peptides restricted to the H2-Kb/Db and analyzed by an IFN γ ELISPOT assay. Black arrows represent days of vaccination. IFN-γ hTERT specific CD8 T-cells/200,000 PBMCs are represented individually for each mice. (B) At day 28, splenocytes were Ficoll purified and half were stimulated in an IFN-γ ELIspot assay in triplicates with MV or a pool of 4 hTERT specific peptides restricted to H2-K/Db. MV specific T-cells and hTERT specific CD8 T-cells/200,000 splenocytes for prime with Ubi-ΔhTERT DNA (hatched bars) and prime-boost with Ubi-ΔhTERT DNA+ MVSchw or MV-TERT (grey bars) are represented as mean±SD. MV specific T-cell stimulation was used as immunization control. Mann Whitney non parametric test between MV-TERT and Ubi-ΔhTERT DNA, $**p<0.01$. (C and D) The second half of splenocytes was stimulated with MV and the pool of hTERT specific peptides for 24 h. Supernatants from stimulated cells were recovered and tested in a deflected CBA assay in order to evaluate the concentration of different cytokines secreted by (C) hTERT specific CD8 T-cells and (D) MV specific T-cells. Cytokine concentrations in pg/mL are represented as mean±SD. Mann Whitney non parametric test against mice control (MVSchw), $*p<0.05$; $**p<0.01$.

DETAILED DESCRIPTION OF THE INVENTION

Definitions

The telomerase complex consists of an RNA template and protein components including a reverse transcriptase, designated "Telomerase Reverse Transcriptase" (TERT), which is the major determinant of telomerase activity. Unless otherwise specified, in the present specification, the term "telomerase" refers to TERT, including wild-type human telomerase, or variants thereof. Wild-type human telomerase (or hTERT) is known (GeneBank Accession number NM_198253), and has amino acid sequence SEQ ID NO: 2 (the cDNA is shown as SEQ ID NO: 1)

The "telomerase catalytic activity" refers to the activity of TERT as a telomerase reverse transcriptase. The term "devoid of telomerase catalytic activity" means that the nucleic acid sequence encodes a mutant TERT, which is inactive.

In the present invention, the term "variant" refers to allelic variants, splicing variants, natural or artificial mutants, which are homologous to the hTERT sequence of reference. Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.).

By "substituted" or "modified" the present invention includes those amino acids that have been altered or modified from naturally occurring amino acids.

Variants include proteins having a sequence that differs from wild-type hTERT protein by one or several mutations (i.e. substitutions, deletions, insertions), still preferably one or several single point substitutions. The variant may comprise conservative substitutions.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e. g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The term "cDNA" encompasses a DNA molecule obtained by reverse transcription of an RNA molecule, including but not limited to an mRNA molecule. Any other technique for the preparation of DNA, starting from the material disclosed in the present invention or using the disclosed features relating to the cDNA of the invention can be used, including techniques involving synthesis or PCR. Therefore, the expression "cDNA" used for the description of the nucleotide sequence of the molecule of the invention merely relates to the fact that originally said molecule is obtained by reverse transcription of the full length genomic (−)RNA strand of the genome of viral particles of the measles virus. This should not be viewed as a limitation for the methods used for its preparation. Purified nucleic acids, including DNA are thus encompassed within the meaning cDNA according to the invention, provided said nucleic acid, especially DNA fulfils the above-given definitions.

The term "immunogenic" means that the composition or construct to which it refers is capable of inducing an immune response upon administration. "Immune response" in a subject refers to the development of an innate and adaptive immune response, including a humoral immune response, a cellular immune response, or a humoral and a cellular immune response to an antigen. A "humoral immune response" refers to one that is mediated by antibodies. A "cellular immune response" is one mediated by T-lymphocytes. It includes the production of cytokines, chemokines and similar molecules produced by activated T-cells, white blood cells, or both. Immune responses can be determined using standard immunoassays and neutralization assays for detection of the humoral immune response, which are known in the art.

In the context of the invention, the immune response preferably encompasses stimulation or proliferation of cytotoxic CD8 T-cells and/or CD4 T-cells and can be determined using immunoassays such as the ELIspot assay, the in vivo cytotoxicity assay or the cytokine secretion binding assay.

As used herein, the term "treatment" or "therapy" or "immunotherapy" refers to any of the alleviation, amelioration and/or elimination, reduction and/or stabilization (e.g., failure to progress to more advanced stages) of a symptom, as well as delay in progression of the tumor or dysplasia, or of a symptom thereof. The term thus includes achievement of an efficient anti tumoral immune response observed in cancer patients.

As used herein, the term "prevention" or "preventing" refers to the alleviation, amelioration and/or elimination, reduction and/or stabilization (e.g., failure to progress to more advanced stages) of a prodrome, i.e. any alteration or early symptom (or set of symptoms) that might indicate the start of a disease before specific symptoms occur.

A cell that "overexpresses telomerase" refers to a cell in a subject, which either expresses telomerase, e.g. upon mutation or infection, especially infection by an oncovirus, whereas it does usually not, under normal conditions, or to a cell in a subject which expresses a higher level of telomerase (e.g. upon mutation or infection), when compared to normal conditions. Preferably the cell that overexpresses telomerase shows an increase of expression of at least 5%, at least 10%, at least 20%, 30%, 40%, 50%, 60%, 70%, 80%, or more.

The "patient" or "subject" is typically a mammal subject, preferably a human subject, of any age, sex, or severity of the condition.

The Heterologous Sequence:

The recombinant measles virus plasmid of the invention comprising a heterologous DNA sequence capable of expressing a heterologous amino acid sequence, wherein said heterologous amino acid sequence is a human telomerase reverse transcriptase (hTERT) protein.

The hTERT sequence that is used in the invention is devoid of telomerase catalytic activity (which abolishes its immortalizing activity) and devoid of a nucleolar localization signal (which prevents its transfer to the nucleolus).

As a first safety lock, the hTERT sequence is devoid of telomerase catalytic activity. In a preferred embodiment, the sequence that encodes hTERT contains mutations that provide inactivation of the catalytic activity of the hTERT protein. The term "mutation" includes a substitution of one or several amino acids, a deletion of one or several amino acids, and/or an insertion of one or several amino acids. In a particular embodiment, the hTERT protein is devoid of telomerase catalytic activity by deletion of at least one amino acid.

Preferably the sequence shows a deletion, preferably a deletion of amino acids VDD. Preferably the hTERT protein is devoid of telomerase catalytic activity by the sole deletion of amino acids 867-869 (VDD) (in reference to the wild-type sequence SEQ ID NO:2). In another particular embodiment, the hTERT protein is devoid of telomerase catalytic activity by a further deletion of 1 to 10, 11 or 12 amino acids upstream and/or downstream amino acids 867-869 (VDD). In a particular embodiment, the polynucleotide encodes a hTERT protein that is deleted for amino acids 867 to 869 (VDD sequence), corresponding to nucleotides 2654 to 2662 of SEQ ID NO:1 (wild-type), or alternatively for amino acids 864 to 872, corresponding to nucleotides 2645 to 2671 of SEQ ID NO: 2 (wild-type). In a particular embodiment, the encoded hTERT protein has a deletion that comprises at least the amino acid residues 867 to 869 i.e., that the deletion is larger than the 3 amino acid residues (VDD sequence). As an example are the 864-872 deletion described above as well as a 22 amino acid deletion starting from amino acid residue 857 to 879 (according to SEQ ID NO: 2) or a deletion comprising the 5 amino acids N-terminal and the 5 amino acids C-terminal to the VDD sequence (from amino acid 862 to amino acid 874 according to SEQ ID NO: 2, corresponding to nucleotides 2639 to 2679).

As a second safety lock, the sequence encoding hTERT is further devoid of the nucleolar localization signal. This nucleolar localization signal is correlated with the subcellular localization of hTERT and thus its enzymatic activity. Preferably the hTERT protein is devoid of a nucleolar localization signal by deletion of at least amino acids 1-23, still preferably by deletion of amino acids 1-47 (in reference to the wild-type sequence SEQ ID NO: 2). In a preferred embodiment, the nucleotide sequence encodes amino acid sequence SEQ ID NO: 7 (also designated "ΔhTERT").

In addition to the modifications that provide the first and second safety locks, the hTERT protein encoded by the nucleic acid construct of the invention may be a wild-type hTERT sequence, or a variant sequence.

The hTERT protein is expressed by the recombinant measles virus plasmid of the invention, in fusion with a protein enhancing addressing of the hTERT protein to proteasome.

Such fusion increases class I presentation of the derived peptides.

Said protein may be preferably ubiquitin or it may be any chaperon protein, e.g. calreticulin. In a preferred embodiment, the recombinant measles virus plasmid of the invention encodes SEQ ID NO: 15, which corresponds to ΔhTERT protein fused to N-terminus of ubiquitin.

The Measles Virus Plasmid:

The invention provides a recombinant measles virus plasmid comprising a cDNA molecule that encodes the full-length, infectious, antigenomic (+)RNA strand of a measles virus (MV), which cDNA molecule further comprises an Additional Transcription Unit (ATU) that contains a heterologous DNA sequence.

ATUs are described in international patent application WO97/06270. Advantageously an ATU may be a copy of the MV N-P intergenic region containing the cis-acting sequences necessary for MV-dependent expression of a transgene inserted into a multiple cloning sites cassette. The term "encodes" in the above definition encompasses the capacity of the cDNA to allow transcription of a full length antigenomic (+)RNA, said cDNA serving especially as template for transcription. Accordingly, when the cDNA is a double stranded molecule, one of the strands has the same nucleotide sequence as the antigenomic (+) strand RNA of the MV, except that "U" nucleotides are substituted by "T" in the cDNA.

Measles virus is a member of the order mononegavirales (*Morbillivirus* genus in the Paramyxoviridae family), i.e., enveloped viruses with a non-segmented negative-strand RNA genome. The non-segmented genome of measles virus (MV) has an antimessage polarity which results in a genomic RNA which is neither translated in vivo or in vitro nor infectious when purified. Transcription and replication of non-segmented (−) strand RNA viruses and their assembly as virus particles have been studied and reported especially in Fields virology (3rd edition, vol. 1, 1996, Lippincott—Raven publishers—Fields B N et al). Transcription and replication of measles virus do not involve the nucleus of the infected cells but rather take place in the cytoplasm of said infected cells. The genome of the measles virus comprises genes encoding six major structural proteins from the six genes (designated N, P, M, F, H and L) and an additional two-non structural proteins from the P. gene which contribute to virus virulence. The gene order is the following: 3', N, P (including C and V), M, F, H, and L large polymerase protein at the 5' end. The cited genes respectively encode the leader peptide (I gene), the proteins of the nucleocapsid of the virus, i.e., the nucleoprotein (N), the phosphoprotein (P), and the large protein (L) which assemble around the genome RNA to provide the nucleocapsid. The other genes encode the proteins of viral envelope including the hemagglutinin (H), the fusion (F) and the matrix (M) proteins.

The plasmid of the invention comprises a cDNA molecule which encodes the nucleotide sequence of the full length antigenomic (+)RNA strand of a measles virus (MV), advantageously originating from an approved vaccine strain.

In a preferred embodiment, the measles virus (MV) originates from the Schwarz strain or the Moraten strain. These strains have been disclosed in several publications and used for the preparation of the currently used vaccines. The inventors propose especially the use of the Schwartz strain which is available from Aventis Pasteur (France). Other attenuated strains, such as strains deriving from the Edmonston strain, could be used as well.

The cDNA molecule allows the production, when placed in appropriate conditions, of an infectious antigenomic (+)RNA capable of producing infectious particles of the measles virus.

The cDNA obtained has especially the original 5'- and 3'-ends of the native antigenomic (+) strand of the viral RNA. In addition, the obtained cDNA complies with the «rule of six». The «rule of six» which is expressed in the fact that the total number of nucleotides present in the cDNA amounts to a multiple of six, rule which allows sufficient replication of genome RNA of the measles virus and expression of infectious viral particles. It has been described in the above cited reference Fields Virology on page 1197.

According to a particular embodiment of the invention, the cDNA molecule is placed under the control of a heterologous expression control sequence.

The insertion of such a control for the expression of the cDNA, is favorable when the expression of this cDNA is sought in cell types which do not enable full transcription of the cDNA with its native control sequences.

According to a particular embodiment of the invention, the heterologous expression control sequence comprises the T7 promoter and T7 terminator sequences. These sequences are respectively located 5' and 3' of the coding sequence for the full length antigenomic (+)RNA strand of MV and from the adjacent sequences around this coding sequence.

In a particular embodiment of the invention, the cDNA molecule which is defined hereabove is modified i.e., comprises additional nucleotide sequences or motifs or comprises deletions or substitutions within said cDNA.

In a preferred embodiment, the cDNA molecule of the invention further comprises, at its 5'-end, adjacent to the first nucleotide of the nucleotide sequence encoding the full length antigenomic (+)RNA strand of the MV approved vaccine strain, a GGG motif followed by a hammerhead ribozyme sequence and which comprises, at its 3'-end, adjacent to the last nucleotide of said nucleotide sequence encoding the full length anti-genomic (+)RNA strand, the sequence of a ribozyme. The Hepatitis delta virus ribozyme (6) is appropriate to carry out the invention.

The GGG motif placed at the 5' end, adjacent to the first nucleotide of the above coding sequence improves the efficiency of the transcription of said cDNA coding sequence. As a requirement for the proper assembly of measles virus particles is the fact that the cDNA encoding the antigenomic (+)RNA complies with the rule of six, when the GGG motif is added, a ribozyme is also added at the 5' end of the coding sequence of the cDNA, 3' from the GGG motif, in order to enable cleavage of the transcript at the first coding nucleotide of the full length antigenomic (+)RNA strand of MV.

Thus, in case where the GGG motif is added to improve efficiency of transcription, two ribozymes are added in order to ensure the cleavage of the coding sequence for the full length antigenomic (+)RNA strand of the MV.

The invention especially also relates to a cDNA molecule which is capable of producing infectious viral particles of the MV strain under conditions enabling viral particles assembly. In particular embodiments, one can employ the previously reported rescue system involving 293-3-46 helper cells (Radecke et al. 1995, and WO 97/06270), or HEK293-T7-MV or HEK-293-T7-NP helper cells described in WO08/078198, both helper cells expressing proteins necessary for transcription and replication of the RNA genome-sequence of MV from said cDNA.

293-3-46 cells and HEK-293-T7-MV cells are cited as examples for the preparation of the viral particles. However they can be replaced by any other appropriate cell line suitable for constituting helper cells.

In a particular embodiment, the invention employs plasmid pTM-MVSchw deposited at the CNCM (Collection Nationale de Cultures de Micro-organismes, Institut Pasteur, 25-28 rue du Docteur Roux, 75015 Paris) on Jun. 12, 2002 under no I-2889.

This plasmid is described in European patent application EP2311853. It is a plasmid vector derived from Bluescript, comprising the full length sequence coding for the measles virus, strain Schwarz, placed under the control of the promoter of the T7 RNA polymerase; its size is 18967 nucleotide.

In a particular embodiment, an ATU, which is typically a copy of the MV N-P intergenic region, may be inserted in pTM-MVSchw using a SalI restriction site.

According to a particular embodiment of the invention, a transgene coding for a Ubiquitin-ΔhTERT-Flu HLA-A*0201 epitope-V5 tag nucleotide sequence was inserted into the ATU using BsiWI/BssHII restriction site. The resulting cDNA was designated as pTM-MV-TERT and respected the "rule of six".

In a particular embodiment of the invention, the cDNA molecule is the product of the reverse transcription of the viral RNA purified from viral particles of the measles virus.

The preparation of the cDNA from viral purified RNA advantageously limits the presence of cellular components and especially cellular DNA or RNA which could be present in cells used for the cultivation of the virus.

According to the invention, the recombinant cDNA molecule further comprises a heterologous DNA sequence as defined above, cloned therein in conditions enabling its expression as a heterologous amino acid sequence, said cloning being performed in such a way that the obtained recombinant cDNA complies with the rule of six.

The ATU is advantageously located in the N-terminal sequence of the cDNA molecule encoding the full-length (+)RNA strand of the antigenome of the MV and is especially located between the P and M genes of this virus or between the H and L genes.

It is further provided a vector comprising a cDNA molecule as defined above including a recombinant cDNA. A particular vector is vector for cloning and/or expressing of this cDNA.

It is also described a method for the preparation of infectious measles virus particles comprising:

1) expressing the plasmid described herein in a helper cell line which also expresses proteins necessary for transcription, replication and encapsidation of the antigenomic (+)RNA sequence of MV from said cDNA and under conditions enabling viral particles assembly and 2) recovering the expressed viral particles.

In particular embodiment of this process, the method comprises:

1) transfecting helper cells with the plasmid described herein, wherein said helper cells are capable of expressing helper functions to express an RNA polymerase, and to express the N, P and L proteins of the MV virus;

2) co-cultivating said transfected helper cells of step 1) with passaged cells suitable for the passage of the MV vaccine strain from which the cDNA originates;

3) recovering the infectious MV viral particles produced.

As an example, helper cells may derive from human embryonic kidney cell line 293, which cell line 293 is deposited with the ATCC under No. CRL-1573.

According to another aspect, the cells suitable for passage are Vero cells, or CEF cells.

The invention also concerns an immunogenic or vaccine composition. Such an immunogenic or vaccine composition has advantageously an active principle which comprises measles virus particles rescued from the cDNA of the plasmid which has been defined hereabove, which is expressed in a helper cell based rescue system.

It is further provided a cell which is recombined with a cDNA molecule according to the invention or with a vector as defined above. Such cell advantageously comprises nucleotide sequences expressing helper functions necessary to express an RNA polymerase and to express the N, P and L proteins of the MV virus. Such a cell can thus be used for the rescue of the viral particles.

A preferred cell is a eukaryotic cell.

Immunogenic or Vaccine Compositions and Administration

The recombinant plasmid or the measles viral particles rescued therefrom may be formulated in a pharmaceutical composition, in association with a physiologically acceptable vehicle, optionally combined with an adjuvant.

Such composition, useful as a vaccine, may comprise one or more pharmaceutically acceptable vehicles or excipients. Excipients include any component that does not itself induce the production of antibodies and is not harmful to the subject receiving the composition. Suitable pharmaceutical vehicles are well known to those of ordinary skill in the art, including, but not limited to, diluents, such as water, saline, and others. Suitably, sterile pyrogen-free, phosphate buffered physiologic saline is a pharmaceutical vehicle. Additionally, additives, such as wetting or emulsifying agents, pH buffering substances, and the like, may be present.

Immunogenic compositions or vaccines are formulated into suitable dosage for the subject to which it is to be administered. The dosage administered may vary with the condition, sex, weight and age of the individual; the route of administration; and the adjuvant used. The composition may be used in dosage forms such as suspensions or liquid solutions. The composition may be formulated with a pharmaceutically acceptable vehicle as described above. The immunogenic composition or vaccine may be administered by any convenient route, preferably parenterally, intramuscularly, intradermally, subcutaneously, mucosally, or intravenously.

A variety of techniques are available for DNA vaccination, such as electroporation, needle-free approaches, such as particle bombardment and high-pressure delivery, dermal patches, formulation of DNA composition or vaccine in microparticles or liposomes.

The compositions may also be administered ex vivo to lymphoid or myeloid cells using liposomal transfection, particle bombardment or viral transduction (including co-cultivation techniques). The treated cells are then reintroduced back into the subject to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, for instance, is administered to the corresponding species and the resulting immune response is observed, for example by detecting the cellular immune response by an IFNγ Elispot assay (as described in the experimental section), by detecting CTL responses using an in vivo lysis assay or a chromium release assay or detecting Th (helper T-cell) response using a cytokine release assay. In a particular embodiment, an administration of $10^3$ to $10^6$, preferably about $10^5$, $TCID_{50}$ is preferred.

In a preferred embodiment, the vaccination regimen comprises one to three injections, optionally repeated two to five weeks later, preferably a month later (especially in humans).

A prime-boost regimen is possible but not compulsory in the context of the present invention.

In a particular embodiment, the vaccination schedule can be composed of one or two injections followed three or four weeks later by at least one cycle of three to five injections.

In another embodiment, a primer dose consists of one to three injections, followed by at least a booster dose every year, or every two or years for instance.

These are examples only, and any other vaccination regimen is herein encompassed.

In a preferred embodiment, it is provided a kit-of-parts comprising i) a DNA molecule encoding hTERT protein which is preferably devoid of telomerase catalytic activity and of a nucleolar localization signal, and ii) an immunogenic composition or recombinant measles virus plasmid according to the present invention, for sequential administration to a subject. The DNA molecule encoding the hTERT protein used as a prime injection, is preferably a DNA vaccine construct as described in international patent application WO2015/063117. The immunogenic composition or recombinant measles virus plasmid according to the present invention is then used to boost the immune response.

Prevention or Treatment of Tumors

The plasmid, viral particle, or the immunogenic or vaccine composition as described herein is useful in a method for preventing or treating a tumor in a patient.

The viral particles of the invention are useful in triggering an immune response in a subject, preferably a cellular immune response, against cells that overexpress telomerase, preferably dysplasic, hyperplasic or tumor cells, as well as cells infected with an oncovirus.

Such treatment can be referred to as an active immunotherapy or therapeutic vaccination, as it triggers an immune response against the tumor, especially a cytotoxic CD8 T-cell response, along with a specific CD4 T-cell response.

A broad cellular immune response is obtained because both CD4 and CD8 T-cell repertoires are stimulated by the epitopes available on hTERT. Induced-CD8 T-cells present cytolytic activities which are the hallmark of anti-tumor cells. Humoral immune responses are obtained because of MV specific B lymphocytes. Production of interleukins is improved, following induction of MV specific CD8 and CD4 T-cells during a prime-boost strategy, especially Tc1/Th1/Th2 cytokines, allowing optimal growth and differentiation of CD8 T-cells.

A method for preventing or treating a tumor in a patient is described, which method comprises administering an effective amount of said plasmid, viral particle, or immunogenic or vaccine composition in a patient in need thereof. Said plasmid, viral particle, or immunogenic or vaccine composition is administered in an amount sufficient to induce an immune response in the patient.

The tumor may be any undesired proliferation of cells, in particular a benign tumor or a malignant tumor, especially a cancer.

The cancer may be at any stage of development, including the metastatic stage. The cancer may be chronic or non-chronic (acute).

In a particular embodiment, tumor is a solid cancer or a carcinoma. Examples include melanoma, brain tumor such as glioblastoma, neuroblastoma and astrocytoma and carcinomas of the bladder, breast, cervix, colon, lung, especially non-small cell lung cancer (NSCLC), pancreas, prostate, head and neck cancer, or stomach cancer.

In another embodiment, the tumor may be a liquid tumor, e.g. a hematopoietic tumor or leukemia, such as a chronic or acute lymphocytic leukemia, chronic or acute myeloid leukemia, lymphoma including Hodgkin's disease, multiple myeloma, malignant myeloma.

In a particular embodiment, the treatment according to the invention may be combined with conventional therapy, including chemotherapy, radiotherapy or surgery. Combinations with adjuvant immunomodulating molecules such as GM-CSF or a cytokine like IL-2 or IL-12, could also be useful.

In a particular embodiment, it is described a method for preventing or treating a tumor in a patient, which method comprises sequentially administering i) a DNA molecule encoding hTERT protein which is preferably devoid of telomerase catalytic activity and of a nucleolar localization signal, and ii) an immunogenic composition or recombinant measles virus plasmid according to the present invention. The DNA molecule encoding the hTERT protein used as a prime injection, is preferably a DNA vaccine construct as described in international patent application WO2015/063117. The immunogenic composition or recombinant measles virus plasmid according to the present invention is then used to boost the immune response.

The Examples and Figures illustrate the invention without limiting its scope.

Example I

Abbreviations

AA: Amino Acid, APC: Antigen Presenting Cell, ATU: Additional Transcription Unit, bp: Base pair, DNA: Desoxyribonucleic Acid, DV: Dengue Virus, CFSE: Carboxyfluorescein succinimidyl ester, CTL: Cytotoxic T-Lymphocyte, HBV: Hepatitis B virus, HIV: Human Immunodeficiency Virus, hTERT: human Telomerase Reverse Transcriptase, L: MV polymerase, M: MV matrix protein, MV: Measles Virus, IP: Intraperitoneal, IV: Intravenous, NoLS: Nucleolar Localization Sequence, N: MV nucleoprotein, NT: untreated, ON: Overnight ORF: Open Reading Frame, OD: Optical Density, P: MV phosphoprotein, PBMCs: Peripheral Blood Mononuclear Cells, RNA: Ribonucleic Acid, RT: Room Temperature, RTA: Relative Telomerase Activity, TCID: Tissue Culture Infectious Dose, TERT: Telomerase Reverse Transcriptase, Ubi: Ubiquitin, VDD: Valine-Aspartic Acid-Aspartic Acid, WNV: West Nile Virus Materials and Methods MV-TERT Immunogenic Composition Insertion of ATU in pTM-MVSchw The plasmid pTM-MVSchw containing an infectious MV cDNA which corresponds to the cloned anti-genome of the Schwarz MV vaccine strain has been described previously (Combredet et al., 2003b). Briefly, the Schwarz cDNA was cloned from viral particles purified from a batch of MV vaccine (Aventis Pasteur). Viral RNA was reverse-transcribed into a cDNA using a mixture of random hexamers as primers. Six overlapping fragments were generated and fused by PCR in order to assemble the full-length Schwarz MV cDNA. The viral antigenomic cDNA was placed under the control of the phage T7 polymerase promoter to maximize the yield of the reverse genetics system described by Radecke et al. (1995). A hammerhead ribozyme (hh) and the hepatitis delta virus ribozyme (hðv) were inserted to facilitate cleavage of viral RNA for both extremities.

The pTM-MVSchw was modified to allow foreign gene expression by introduction of additional transcription unit (ATU). A multiple cloning site cassette ATU was inserted into the pTM-MVSchw plasmid by site-directed mutagenesis in a SalI site in position 3446 of the pTM-MVSchw between the MV P and M genes. Each MV open reading (ORF) expression has a successive independent transcription controlled by its own cis-acting element. Additional ORFs inserted in the ATU is controlled by cis-acting element equivalent to those present in the N/P intergenic region. The resulting plasmid was named pTM-MVSchw-ATU2.

pTM-MV-TERT: Subcloning of the Ubi-ΔhTERT-Flu-V5 Insert into the pTM-MVSchw-ATU2

Ubi-ΔhTERT-Flu-V5 insert encodes a modified protein of human Telomerase Reverse Transcriptase (hTERT) fused to ubiquitin (Ubi), Flu epitopes restricted to HLA-A*0201 and the V5 tag corresponding to a protein of approximately 130.9 kDa (FIG. 1B). The hTERT was devoid of catalytic activity by a 9 bp deletion coding for three amino acid Valine-Aspartic Acid-Aspartic Acid (867-869 AA of wild-type hTERT), abbreviated to VDD in the one letter code. The 47 AA of the N-terminal part of the protein, which include the nucleolar localization sequence (NoLS) required for telomerase subcellular localization (Yang et al., 2002) was replaced by the ubi coding sequence (1-76 AA). In addition, a Flu epitope restricted to HLA-A*0201 and a V5 tag was added at the C-terminal part of this fusion protein to facilitate in vitro or ex vivo characterization of the recombinant MV-TERT.

The Ubi-ΔhTERT-Flu-V5 gene was de novo synthetized assembly of overlapping 40-mer oligonucleotides (Gene-Cust, Luxembourg). Several conservative base changes were made to eliminate restriction sites and attenuate GC rich sequences. Gene synthesis included unique flanking restriction sites BsiWI/BssHII to allow subcloning of the gene into desired expression system.

Therefore, the transgene cDNA sequence has been subcloned into BsiWI/BssHII-digested pTM-MVSchw-ATU2. The resulting plasmid was designated as pTM-MV-TERT. The entire sequence respects the "rule of six" in which the number of nucleotides into the MV genome must be a multiple of 6 to allow efficient replication.

Rescue of Recombinant MV-TERT from the pTM-MV-TERT and MVSchw from the pTM-MVSchw The corresponding MV-TERT or MVSchw viruses were recued from the pTM-MV-TERT or pTM-MVSchw cDNA respectively using a helper cell-based rescue system (Combredet et al., 2003b; Parks et al., 1999; Radecke et al., 1995). Briefly, HEK293 cells expressing stably both the T7-RNA polymerase and the Schwarz MV N and P proteins (HEK293-T7-MV) were co-transfected using calcium phosphate with the pTM-MV-TERT or pTM-MVSchw (5 µg) and a plasmid expressing the MV polymerase L gene (pEMC-La, 20 ng). After incubation and heat shocks (37° C. ON; 43° C. heat-shocked 3 h; 37° C. 2 days), transfected HEK293-T7-MV helper cells were transferred onto a monolayer of Vero cells and incubated at 37° C. Single syncytia were isolated and transferred to a new monolayer of Vero cells for the amplification of virus. Virus were harvested when syncytia reached 80 to 90% of the culture and virus titers were determined by an endpoint limit dilution assay on Vero cells. The titers were calculated using the Karber method and were expressed as TCID50/mL.

Ubi-ΔhTERT DNA

The plasmid DNA coding for a human ubiquitin-modified hTERT fusion construct of 1158 AA (Ubi-hTERT) was designed as the same manner that the nucleotide sequence of ubi-ΔhTERT-Flu-V5 insert. Briefly, hTERT was devoid of its catalytic activity by the 9 bp deletion coding for VDD amino-acids. Its NoLS was also replaced by human ubiquitin sequence. This plasmid (also named "INVAC-1") was previously described in international patent application WO2015/063117.

Cell Cultures

HEK293-T7-MV helper cells used for MV-TERT or MVSchw rescue were cultured in Dulbecco's modified Eagle's medium (DMEM) without sodium pyruvate supplemented with 10% heat-inactivated fetal calf serum and 1% penicillin/streptomycin (Life Technologies, Saint-Aubin, France). These cells were grown as monolayers in 35 mm wells at 37° C. in a humidified atmosphere containing 5% $CO_2$.

Vero cells were maintained in Dulbecco's modified Eagle's medium (DMEM) without sodium pyruvate supplemented with 10% heat-inactivated fetal calf serum and 1% penicillin/streptomycin (Life Technologies, Saint-Aubin, France). For co-culture, Vero cells were seeded at $5\times10^6$ cells and grown as monolayers in 10 cm dishes at 37° C. and 5% $CO_2$ until single syncytia formation. For amplification, $3\times10^5$ Vero cells were seeded in 12-well tissue culture plates and incubated to obtain 80 to 90% of confluence; each syncytium was filed on cells. Then, after 2 days, they were transferred to 25 cm² and then 150 cm² flaks in order to obtain virus stock. For Western blot assay, Vero cells were seeded at $2\times10^6$ cells and grown as monolayers in 25 cm² flasks at 37° C. in a humidified atmosphere containing 5% $CO_2$. They were infected at MOI=0.1 for 48 h.

Western Blots

For Western blot analyses, Vero cells were lysed on ice for 10-20 minutes in RIPA buffer (Sigma-Aldrich, St. Louis, USA) supplemented with a protease inhibitor cocktail (Roche Diagnostic, Indianapolis, USA). Lysates were cleared by centrifugation at 14,000 rpm for 15 minutes at 4° C. The supernatants were harvested and the protein concentration was measured using the Bradford colorimetric assay. Protein samples were denatured 5 minutes at 95° C., separated on Nu-PAGE® Novex 4-12% Bis-Tris gels (Invitrogen, Carlsbad, USA) and electroblotted onto PVDF membranes (iBlot® transfer stack, Invitrogen, Carlsbad, USA) using the iBlot® device (Invitrogen, Carlsbad, USA). Novex® Sharp Prestained Protein Ladder (Invitrogen, Carlsbad, USA) were used to determine molecular weight. The membranes were cut approximately at 50 kDa and then at 70 kDa and blocked with 1×PBS, 0.05% Tween®20, 3% milk. The upper part of the membrane was probed with an anti-V5 mouse monoclonal antibody (Invitrogen, Carlsbad, USA) diluted at 1/5000 in blocking buffer. The middle part was probed with an anti-MV N mouse monoclonal antibody (Abcys, Courtaboeuf, France) diluted at 1/2000. The lower part of the membrane was probed with an anti-β-actin mouse monoclonal antibody (Sigma Aldrich SARL, Saint-Quentin Fallavier, France) diluted at 1/5000. Finally, the relevant proteins were visualized by staining with an anti-mouse HRP linked antibody (GE Healthcare, Vélizy, France) diluted at 1/5000 for 1 h at room temperature. Proteins were detected by enhanced chemiluminescence assay using ECL HRP chemiluminescent substrate Reagent Kit. The films and cassette were from GE Healthcare (Buckinghamshire, UK).

Mice

Mice susceptible for MV infection were obtained as previously described (Combredet et al., 2003a; Lorin et al., 2005). The transgenic IFNAR/CD46 mice express hCD46, one of the MV human receptor (Naniche et al., 1993) and were knock-out for the IFNα/β receptor (IFNAR) (Mrkic et al., 1998). The HHD/IFNAR/CD46 mice also express a transgenic MHC class-I molecule HLA-A*0201 (Pascolo et al., 1997). Transgenic mice were used between 6 and 16 weeks of age.

Prior to intradermal (ID) or intravenous (IV) injection, mice were anesthetized with a mix solution of 2% xylazine (Rompun, Bayer Santé, Loos, France) and 8% Ketamine (Imalgen 1000, Merial, Lyon, France) in 1× Phosphate Buffer Saline (1×PBS, Life Technologies, Saint-Aubin, France) through the intraperitoneal route (IP) according to individual animal weight and duration of anesthesia. All animals were handled in strict accordance with good animal practice and complied with local animal experimentation (Directive 2010/63/UE).

hTERT Peptides hTERT peptides restricted to HLA-A*0201 were previously described (see references in Table 1). hTERT peptides restricted to H2-K/Db and H2-IAb were determined by in silico epitope prediction in order to bind mouse MHC Class I and II molecules using four algorithms available online: Syfpeithi (http://www.syfpeithi.de/), Bimas (http://www-bimas.cit.nih.gov/), NetMHCpan and SMM (http://tools.immuneepitope.org/main/). All synthetic peptides were purchased lyophilized (>90% purity) from Proimmune (Oxford, United Kingdom). Lyophilized peptides were dissolved in sterile water at 2 mg/mL and stored at −80° C. or −20° C. prior use. Details of peptide sequences and MHC restriction are shown in Table 1.

TABLE 1 hTERT peptides and MHC restriction

| Peptide Code (reference) | Sequence | MHC | Predicted on | Mouse Strain |
|---|---|---|---|---|
| 540 (Hernandez et al., 2002) | ILAKFLHWL (SEQ ID NO: 16) | HLA-A*0201 | hTERT | HHD/IFNAR/CD46 |
| Y572 (Hernandez et al., 2002) | YLFFYRKSV (SEQ ID NO: 17) | | | |
| Y988 | YLQVNSLQTV (SEQ ID NO: 18) | | | |
| UCP2.1 (Dosset et al., 2012) | SVWSKLQSI (SEQ ID NO: 19) | | | |
| UCP4.1 (Dosset et al., 2012) | SLCYSILKA (SEQ ID NO: 20) | | | |
| 429 | HAQCPYGVL (SEQ ID NO: 21) | H2-Kb | Ubi-ΔhTERT | IFNAR/CD46 |
| 1034 | QAYRFHACVL (SEQ ID NO: 22) | | | |
| 660 | RPIVNMDYV (SEQ ID NO: 23) | H2-Db | | |
| 1021 | QTVCTNIYKI (SEQ ID NO: 24) | | | |
| 85 | VCVPWDARPPPAAPS (SEQ ID NO: 25) | H2-IAb | Ubi-ΔhTERT | IFNAR/CD46 |
| 86 | CVPWDARPPPAAPSF (SEQ ID NO: 26) | | | |
| 87 | VPWDARPPPAAPSFR (SEQ ID NO: 27) | | | |
| 329 | GRQHHAGPPSTSRPP (SEQ ID NO: 28) | | | |
| 1080 | MSLGAKGAAGPLPSE (SEQ ID NO: 29) | | | |
| 1082 | LGAKGAAGPLPSEAV (SEQ ID NO: 30) | | | |
| 1137 | TLTALEAAANPALPS (SEQ ID NO: 31) | | | |
| 1138 | LTALEAAANPALPSD (SEQ ID NO: 32) | | | |

MV-TERT Immunization

Intraperitoneal (IP) immunization was performed with insulin syringes and specific needles (U-100, 29GX1/2"-0.33×2 mm, Terumo, Belgium). Each animal received a prime or a boost with $10^5$ TCID50 of recombinant MV-TERT or MVSchw, depending on the experiment.

DNA Immunization with In Vivo Electroporation Procedure

Intradermal (ID) immunization was performed on the lower part of the mouse flank with insulin syringes and specific needles (U-100, 29GX1/2"-0.33×12 mm, Terumo, Belgium) after shaving. No erythema was observed after shaving, during and after the immunization procedures. Each animal received a priming ID with 25 μg of plasmid coding for Ubi-ΔhTERT or 1×PBS, depending on the experiment.

In vivo DNA electroporation was performed using the CLINIPORATOR® 2 electroporation system and software (IGEA, Italy) equipped with plate electrodes (P-30-8G, IGEA). Directly after ID administration, a skin fold was made at the injection site, entirely covered with conductive gel (Labo F H, blue contact gel, NM Médical, France) and placed between the plate electrodes. Two pulses of different voltages were applied (HV-LV): HV: 1000 V/cm, 1 Hz, 100 μs; 1 pulse, 1000 ms break; LV: 140 V/cm, 1 Hz, 400 ms, 1 pulse.

ELIspot Assay

Spleens from immunized mice were harvested and crushed to isolate splenocytes. Blood from immunized mice was collected through retro-orbital puncture under anaesthesia in order to isolate peripheral mononuclear blood cells (PBMCs). Splenocytes or PBMCs were Ficoll purified (Lymphocyte Separation Medium, Eurobio, France) and were numerated using the Cellometer® Auto T4 Plus counter (Ozyme, France).

Murine IFN-γ kits were purchased from Diaclone (Eurobio, Courtaboeuf, France, ref. 862.031.010P). They were used following the manufacturer's instructions. Briefly, cell suspensions were stimulated in triplicates at $2 \times 10^5$ cells/well with 5 μg/ml of H2 or HLA-A2 restricted hTERT derived peptides, with serum free culture medium (as negative control), with MVSchw at MOI=1 (as control of immunization) or with PMA-ionomycin as positive control (0.1 μM and 1 μM respectively). After 19 hours, spots were revealed with the biotin-conjugated detection antibody followed by streptavidin-AP and BCIP/NBT substrate solution. Spots were counted using the Immunospot ELIspot counter and software (CTL, Germany).

In Vivo Cytotoxicity Assay

The capacity of CD8 cytotoxic T-cells to kill peptide-loaded target cells in vivo was assessed as described previously (Durward et al., 2010). Briefly, splenocytes from naive IFNAR/CD46 mice were labeled by a 1×PBS solution containing high (5 μM), medium (1 μM) or low (0.2 μM) concentrations of CFSE (Vybrant CFDA-SE cell-tracer kit; Life Technologies, Saint-Aubin, France). Subsequently, $CFSE^{high}$-labeled cells were pulsed with the immunodominant hTERT p660 peptide and $CFSE^{medium}$-labeled cells were pulsed with the subdominant p1034 hTERT peptide for 1.5 hours whereas $CFSE^{low}$-labeled cells were left unpulsed. Cells were mixed in a 1:1:1 ratio and each mouse previously immunized with MV-TERT, MVSchw or PBS received at day 7, $6.8 \times 10^6$ mix CFSE-labeled cells.

Fifteen hours later, single cell suspensions from spleens were analyzed by MACSQUANT® flow cytometer (Miltenyi, Germany). The percentage of specific killing was determined as follows:

$$[1-[\text{mean } (\% \ CFSE^{high \ or \ medium})_{CONTROL}/(\% \ CFSE^{low}/CFSE^{high \ or \ medium})_{IMMUNIZED})]] \times 100.$$

ELISA Assay

Mouse sera collected before immunization (D0) and 1 month after each immunization (D28 and D49) were heat inactivated. MV-specific Ig antibodies were measured by using commercial ELISA kit (Trinity Biotech, USA). Briefly, plates were coated with 50 ng of a solution containing MV antigen and were incubated on night at 4° C. Mouse sera for D28 and D49 were tested in serial dilutions (D28: 1/100, 1/400, 1/600, 1/6400, 1/25600, 1/102400; D49: 1/600, 1/6400, 1/25600, 1/102400, 1/409600, 1/1638400) to determine the end point limit positive dilution. Mouse sera for D0 were used diluted at 1/100 to determine a threshold value (Thr). Diluted sera were incubated 1 h at RT. A secondary anti-mouse antibody-HRP conjugate (Amersham) was used diluted at 1/5000 and was incubated 1 h at RT. The signal was revealed by addition of the TMB substrate and absorbance was measured for each sample. Antibody titers were determined as follows:

$$\text{Titer} = \exp((\ln(\text{high dilution factor}) + (OD_{high \ dilution \ factor} - Thr)/(OD_{high \ dilution \ factor} - OD_{low \ dilution \ factor})) * \ln(\text{low dilution factor/high dilution factor}))$$

The presence of hTERT-specific binding antibodies in mouse sera was performed by Bertin Pharma (France) according a validated qualitative ELISA immunoassay. Samples of test sera were incubated with a recombinant hTERT peptide (184AA, P165-S348) provided by GenWay (San Diego, USA). A secondary goat anti-mouse IgG conjugated to alkaline phosphatase was added. Antigen-Ab complexes were visualized by addition of a chromogenic substrate. Results are expressed as mean ratio (R) where R=OD values/cut off point; cut off point=normalized cut off×mean of eight determination of the negative pool of matrices. Positive or negative results were obtained according the Quality Controls (QC) ratio. IFNAR/CD46: R QC high=7.27-7.67; R QC low=1.46-1.50; cut-off=0.252. HHD/IFNAR/CD46: R QC high=8.30-8.99; R QC low=1.43-1.44; cut-off=0.279.

Cytokine Binding Assay (CBA)

Cytometric Beads Array mouse Th1/Th2/Th17 kit (CBA, BD biosciences) was used to quantify respectively the concentration of IL-2, IFNγ, TNFα, IL-4, IL-6, IL-17a and IL-10 which could be secreted by hTERT specific CD8 T-cells or by MV specific T-cells. The CBA immunoassay was carried out according to the manufacturer's instructions. Briefly, splenocytes (6×10 cells) from immunized IFNAR/CD46 mice were cultured 24 h at 37° C. with H2-K/Db-restricted hTERT derived peptides (429, 660, 1021, 1034) at 5 μg/mL or with MVSchw at MOI=1. Cell supernatants were collected and processed. Flow cytometry acquisition was performed using the FACScan LSRII flow cytometer (BD Biosciences); analyses were performed using the FCAP Array™ Software version 3.0 (BD Biosciences).

Statistical Analysis and Data Handling

GraphPad Prism-6 software was used for data handling, analysis and graphic representations. Data are represented as the mean±standard deviation. Statistical analyses were performed using a Mann Whitney non parametric test. Significance was set at p-value<0.05.

Results

Characterization and Sequence Analysis of pTM-MV-TERT for MV-TERT Rescue pTM-MV-TERT is a cDNA which contains the antigenome of MV and a Ubi-ΔhTERT-Flu-V5 transgene. The transgene was successfully ligated into the ATU of pTM-MVSchw-ATU2 using BsiWI/BssHII site (FIG. 1A).

SEQ ID NO: 3 shows the nucleotide sequence of pTM-MV-TERT plasmid expression vector (22,649 bp). Vector features are detailed in FIG. 1A legend. pTM-MV-TERT is a recombinant cDNA with an ATU encoding hTERT fusion protein (1190 AA). The coding transgene starts at position 3535 (ATG coding for M amino-acid) and ends at 7102 (ACT coding for T amino-acid). The Ubiquitin-ΔhTERT-Flu HLA-A*0201 epitope-V5 transgene was deleted of the 47 first amino-acids (1-47 AA) of hTERT which were replaced by an ubiquitin polypeptide (76 AA). The catalytic site of hTERT was inactivated by a 9 bp deletion (nucleotides 6219-6220) coding for VDD (* in the sequence) and corresponding to AA 867-869 of wild-type human telomerase (hTERT; Accession number NM_198253).

Ubi-ΔhTERT-Flu-V5 Proteins is Correctly Expressed In Vitro

After rescue, Vero cells were infected with MV-TERT for 48 hours in order to assess the expression of Ubi-ΔhTERT-Flu-V5 fusion protein by Western blot assay and verify its stability compared to the empty MVSchw. As expected, only MV-TERT and MVSchw virus express the MV nucleoprotein at the predicted size of 57.7 kDa (FIG. 1B, middle part of membrane). In contrast to MVSchw, the MV-TERT recombinant virus expresses two distinct product of the fusion protein (FIG. 1B, upper part of membrane), a weaker upper product corresponding to the Ubi-ΔhTERT-Flu-V5 fusion protein at the predicted size of 130.9 kDa and a major lower product corresponding probably to ΔhTERT-Flu-V5 protein lacking the ubiquitin sequence (122.5 kDa).

Ubi-ΔhTERT-Flu-V5 fusion protein sequence enters into a rapid proteasome-dependent degradation pathway leading to enhanced MHC class I peptides presentation and improved specific immune responses to a variety of antigens (Wang et al., 2012).

Figure 2C:
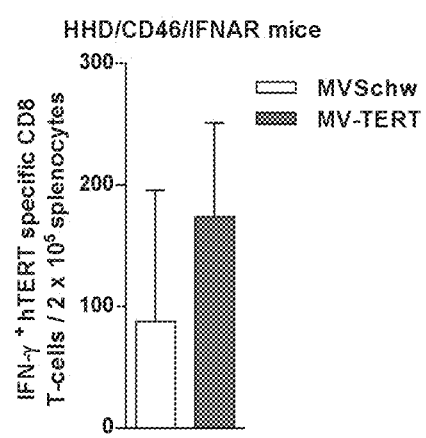
Figure 2B:
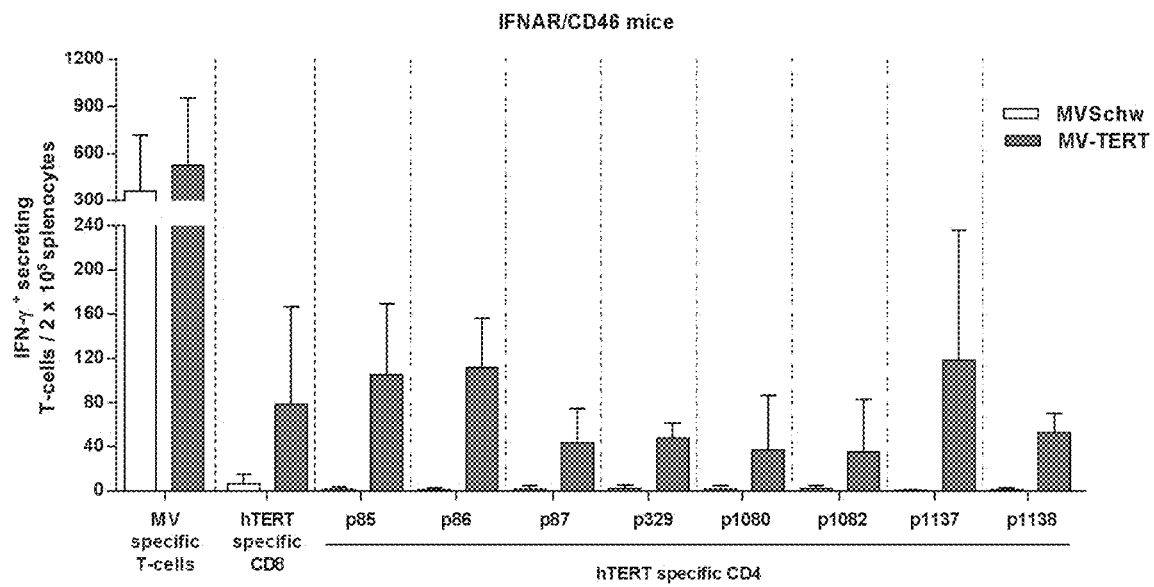

Immunization with MV-TERT Induces Strong hTERT and MV Specific T-Cell Responses in Mice The immunogenicity of MV-TERT recombinant immunogenic composition was assessed in genetically modified IFNAR/CD46 and HHD/IFNAR/CD46 mice susceptible to MV infection. Both MV specific T-cell and hTERT specific T-cell responses were studied in splenocytes collected 7 days or 14 days after immunization via an IFN-γ ELISPOT assay (FIGS. 2A and B) using MSchw virus and hTERT peptides restricted to H2 or HLA-A2. As shown in FIG. 2A, MV-TERT immunized mice generated a significantly higher hTERT specific CD8 T-cell response than MVSchw control mice (p<0.01) 7 and 14 days after last immunization. In the same way, hTERT specific CD4 T-cells were detected in MV-TERT immunized mice in contrast to those immunized with MVSchw (FIG. 2B; minimal mean #spots p1082: 35 and maximum mean #spots p1137: 118).

IFN-γ ELIspot assay to assessed MV-TERT immunogenicity in HHD/IFNAR/CD46 mice was performed after one week of in vitro stimulation with a mix of hTERT specific peptides restricted to HLA-A*0201 on Ficoll-purified-splenocytes. hTERT specific CD8 T-cell responses in mice (FIG. 2C) immunized with MV-TERT were detected higher than MVSchw immunized mice. In addition, it should be noted for both experiments that no significant difference was observed between MV specific T-cell response induced by MVSchw and that induced by MV-TERT (FIGS. 2A and B) indicating that insertion of this transgene does not disturb existing immunogenicity of MV.

MV-TERT Immunization Generates hTERT Specific CTLs Responses

Cytotoxic CD8 T lymphocytes (CTL) have been demonstrated to be the most powerful effector cells involved in cancer cells elimination (Vesely et al., 2011). Thus, it was essential to demonstrate that MV-TERT recombinant virus induces in vivo hTERT specific CD8 T-cells with cytolytic activity. To this aim, in vivo cytotoxicity assay was evaluated in IFNAR/CD46 mice using CFSE-labelled and peptide-pulsed splenocytes as target cells. Target cells were splenocytes from naive congenic mice independently labelled with 3 different concentrations of CFSE and pulsed with hTERT peptide restricted to H2-Db (p660, immunodominant peptide or p1021, sub-dominant peptide) or left unpulsed as an internal control. After 15-18 hours, spleen cells were harvested and the decrease of peptide-pulsed cells in immunized vs. control mice was quantified by flow cytometry. Results show a decrease of high-labelled CFSE cells pulsed with both peptides (p660 and p1021) in MV-TERT immunized mice as compared to MVSchw and control mice (FIG. 3A). Human TERT specific CTLs developed in MV-TERT immunized mice killed significantly ≈50% of p660 pulsed-cells mice and 14% of p1021 pulsed-cells (FIG. 3 B).

Induction of MV Specific Antibodies but No Detection of hTERT Humoral Immune Response to MV-TERT ELISAs were performed to evaluate the immunogenicity of MV-TERT by detection of antiMV and anti-hTERT antibodies in IFNAR/CD46 and HHD/IFNAR/CD46 sera collected at D0, D28 and D49 (FIG. 4). For both mouse strains, one MV-TERT immunization induced a significant high anti-MV antibody titers and a second immunization one month later increased significantly this titers. Indeed, mean of anti-MV antibody titers for MV-TERT immunized INFAR/CD46 mice at D28 were obtained around $8\times10^4$ and at D49 approximately at $3\times10^5$ (FIG. 4A); and mean of anti-MV antibody titers for MV-TERT immunized HHD/INFAR/CD46 mice at D28 were detected at approximately $7\times10^3$ and at D49 at $5\times10^4$ (FIG. 4B).

As expected, no significant difference was observed between the MV-TERT recombinant virus and the empty MVScwh virus for each day (mean IFNAR/CD46 anti-MV titer MVSchw D28≈$10^5$, D49≈$1.5\times10^5$; mean HHD/IFNAR/CD46 anti-MV titer MVSchw D28≈$7.2\times10^3$, D49≈$10^5$).

Figure 4A:
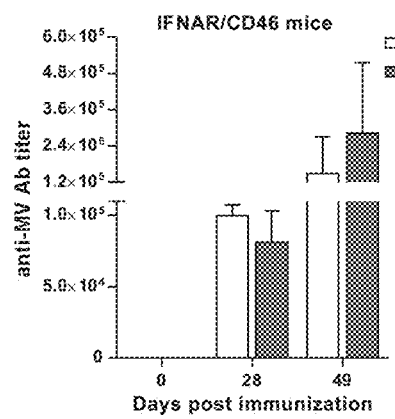
Figure 4B:
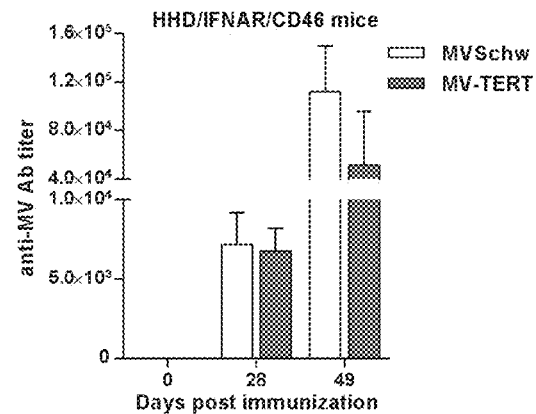
Figure 4C:
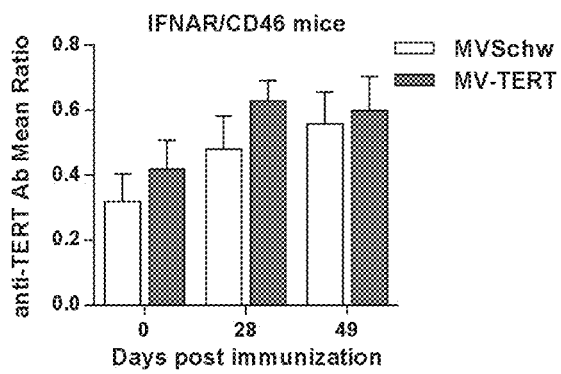
Figure 4D:
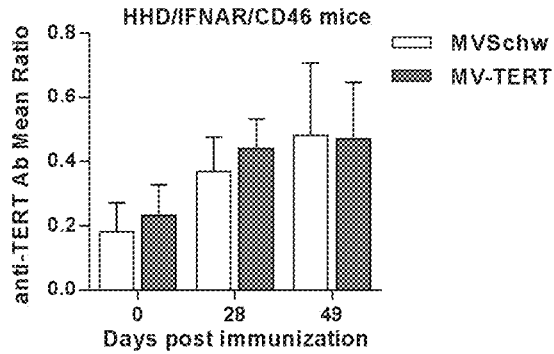

Although all mice respond to MV, anti-hTERT peptide p165-348 antibodies were not detected in both mouse strains after one or two immunizations (FIGS. 4C and D). These results are quite surprising, knowing the potential of natural MV and MV vaccine to induce antibodies persisting 25-30 years after immunization. In addition, numerous studies involving MV recombinant vaccine that encode surface protein of different virus (HIV, WNV, DV, HBV) demonstrate induction of transgene specific humoral response (Brandler et al., 2010; Brandler and Tangy, 2008; Lorin et al., 2004; Singh et al., 1999). However, humoral response against hTERT remains poorly described.

Heterologous Prime-Boost with DNA and MV-TERT Elicited an Enhanced and Multifunctional hTERT Specific T-Cell Responses The impact of the electroporated DNA immunogenic composition encoding Ubi-ΔhTERT combined with the replicating viral vector MV-TERT was evaluated on the induction of hTERT specific CD8 T-cell response.

Figure 5A:
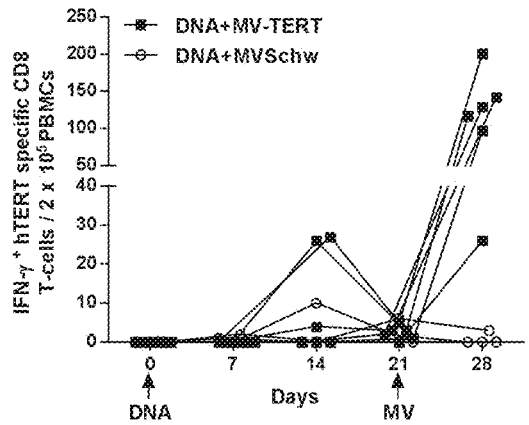

IFNAR/CD46 mice were immunized with DNA at D0 (according to the immunization procedure) and boost 21 days later with MV-TERT or MVSchw (as control; FIG. 5). The hTERT specific CD8 T-cell was monitored in PBMCs overtime (FIG. 5A) and in splenocytes at each end-point (FIG. 5B) by an IFNγ ELISpot assay using hTERT peptides restricted to H2-Kb/Db. Weak or no hTERT specific CD8 T-cell response was observed 14 days after primed with DNA immunization; 2 mice out of ten developed a weak response in blood (FIG. 5A, n=10). However, only the boost with MV-TERT induce high hTERT specific CD8 T-cells in comparison of DNA+MVSchw immunized mice (FIG. 5A, mean #spots: 118.5; n=6). As the same way, in spleen, no hTERT specific CD8 T-cell responses were observed after DNA immunization and significant induction of hTERT specific CD8 T-cells was detected after boost with MV-TERT (FIG. 5B, mean #spots: 453.7; n=6).

Figure 5B:
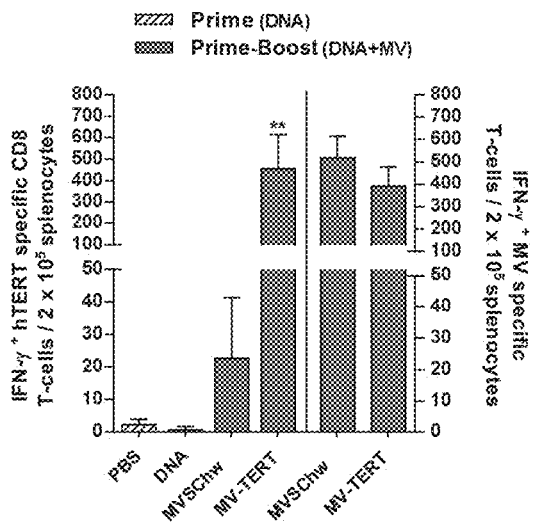
Figure 5C:
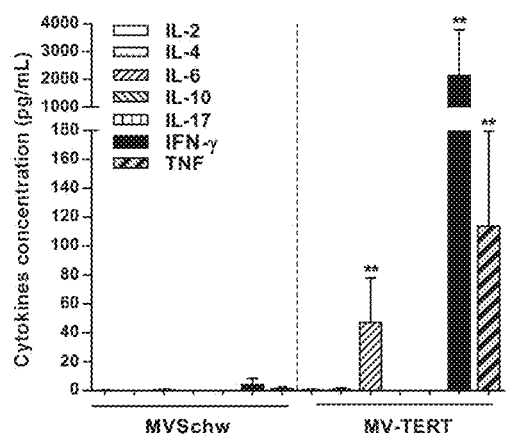
Figure 5D:
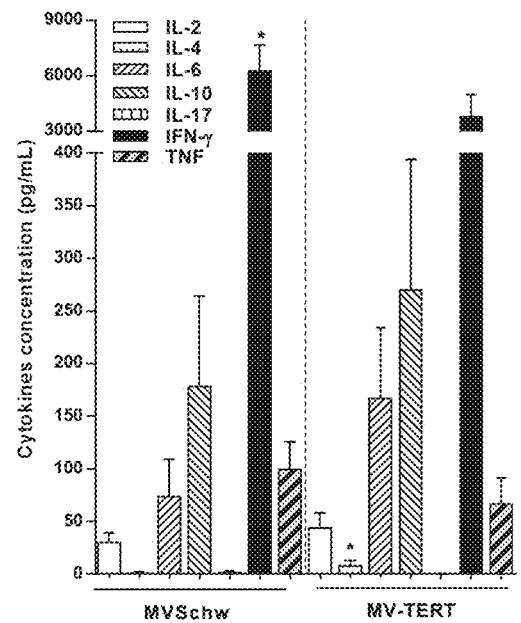

It should be noticed that hTERT specific CD8 T-cell responses induced by heterologous prime-boost was 2 fold higher than the specific response obtained previously with one MV-TERT immunization (FIGS. 5B and 2A). This observation suggests that DNA immunization in IFNAR/CD46 mice might induce the hTERT specific CD8 T-cell repertoire but does not enable its expansion, in contrast to MV-TERT immunization. Indeed, type I IFNs were found to be essential for optimal DNA vaccine immunogenicity and therefore these results appear inherent to IFNAR mice model (Coban et al., 2011; Ishii et al., 2008).

After heterologous prime-boost immunization, the different cytokines secreted by T-cells were assessed in order to demonstrate the functionality of MV specific T-cells and hTERT specific CD8 T cell. Results show (FIG. 5C) that significant concentrations of IL-6, IFN-γ and TNF were detected for hTERT specific CD8 T-cells induced by MV-TERT. These cytokines are characteristic of Tel CD8 T-cell subsets which are described to secrete high level of IFN-γ, TNF, low level of IL-6 and are more cytotoxic than Tc2 cells (Mosmann et al., 1997). In addition, MV CD8 and CD4 specific T-cells induced by MVSchw or MV-TERT secreted the same cytokine, IL-2, IL-6, IL-10, IFN-γ and TNF.

Taken together, these results demonstrated a mixed Tc1/Th1/Th2 polarization of specific T-cells induced by heterologous prime-boost immunization.

REFERENCES

Brandler, S., Ruffle, C., Najburg, V., Frenkiel, M. P., Bedouelle, H., Despres, P., and Tangy, F. (2010). Pediatric measles vaccine expressing a dengue tetravalent antigen elicits neutralizing antibodies against all four dengue viruses. Vaccine 28, 6730-6739.

Brandler, S., and Tangy, F. (2008). Recombinant vector derived from live attenuated measles virus: potential for flavivirus vaccines. Comparative Immunology, Microbiology and Infectious Diseases 31, 271-291.

Cheever, M. A., Allison, J. P., Ferris, A. S., Finn, O. J., Hastings, B. M., Hecht, T. T., Mellman, I., Prindiville, S. A., Viner, J. L., Weiner, L. M., and Matrisian, L. M. (2009). The prioritization of cancer antigens: a national cancer institute pilot project for the acceleration of translational research. Clinical cancer research 15, 5323-5337.

Coban, C., Kobiyama, K., Aoshi, T., Takeshita, F., Horii, T., Akira, S., and Ishii, K. J. (2011). Novel strategies to improve DNA vaccine immunogenicity. Current Gene Therapy 11, 479-484.

Collins, K., and Mitchell, J. R. (2002). Telomerase in the human organism. Oncogene 21, 564-579.

Combredet, C., Labrousse, V., Mollet, L., Lorin, C., Delebecque, F., Hurtrel, B., McClure, H., Feinberg, M. B., Brahic, M., and Tangy, F. (2003a). A molecularly cloned Schwarz strain of measles virus vaccine induces strong immune responses in macaques and transgenic mice. J Virol 77, 11546-11554.

Combredet, C., Labrousse, V., Mollet, L., Lorin, C., Delebecque, F., Hurtrel, B., McClure, H., Feinberg, M. B., Brahic, M., and Tangy, F. (2003b). A molecularly cloned Schwarz strain of measles virus vaccine induces strong immune responses in macaques and transgenic mice. J Virol 77, 11546-11554.

Dosset, M., Godet, Y., Vauchy, C., Beziaud, L., Lone, Y. C., Sedlik, C., Liard, C., Levionnois, E., Clerc, B., Sandoval, F., et al. (2012). Universal cancer peptide-based therapeutic vaccine breaks tolerance against telomerase and eradicates established tumor. Clinical cancer research: an official journal of the American Association for Cancer Research 18, 6284-6295.

Durward, M., Harms, J., and Splitter, G. (2010). Antigen specific killing assay using CFSE labeled target cells. Journal of Visualized Experiments Harley, C. B. (2008). Telomerase and cancer therapeutics. Nature Reviews Cancer 8, 167-179.

Hernandez, J., Garcia-Pons, F., Lone, Y. C., Firat, H., Schmidt, J. D., Langlade-Demoyen, P., and Zanetti, M. (2002). Identification of a human telomerase reverse transcriptase peptide of low affinity for HLA A2.1 that induces cytotoxic T lymphocytes and mediates lysis of tumor cells. Proc Natl Acad Sci USA 99, 12275-12280.

Ishii, K. J., Kawagoe, T., Koyama, S., Matsui, K., Kumar, H., Kawai, T., Uematsu, S., Takeuchi, O., Takeshita, F., Coban, C., and Akira, S. (2008). TANK-binding kinase-1 delineates innate and adaptive immune responses to DNA vaccines. Nature 451, 725-729.

Kim, R., Emi, M., and Tanabe, K. (2007). Cancer immunoediting from immune surveillance to immune escape. Immunology 121, 1-14.

Lorin, C., Delebecque, F., Labrousse, V., Da Silva, L., Lemonnier, F., Brahic, M., and Tangy, F. (2005). A recombinant live attenuated measles vaccine vector primes effective HLA-A0201-restricted cytotoxic T lymphocytes and broadly neutralizing antibodies against HIV-1 conserved epitopes. Vaccine 23, 4463-4472.

Lorin, C., Mollet, L., Delebecque, F., Combredet, C., Hurtrel, B., Charneau, P., Brahic, M., and Tangy, F. (2004). A single injection of recombinant measles virus vaccines expressing human immunodeficiency virus (HIV) type 1 clade B envelope glycoproteins induces neutralizing antibodies and cellular immune responses to HIV. J Virol 78, 146-157.

Mosmann, T. R., Li, L., and Sad, S. (1997). Functions of CD8 T-cell subsets secreting different cytokine patterns. Semin Immunol 9, 87-92.

Mrkic, B., Pavlovic, J., Rulicke, T., Volpe, P., Buchholz, C. J., Hourcade, D., Atkinson, J. P., Aguzzi, A., and Cattaneo, R. (1998). Measles virus spread and pathogenesis in genetically modified mice. J Virol 72, 7420-7427.

Naniche, D., Varior-Krishnan, G., Cervoni, F., Wild, T. F., Rossi, B., Rabourdin-Combe, C., and Gerlier, D. (1993). Human membrane cofactor protein (CD46) acts as a cellular receptor for measles virus. J Virol 67, 6025-6032.

Parks, C. L., Lerch, R. A., Walpita, P., Sidhu, M. S., and Udem, S. A. (1999). Enhanced measles virus cDNA rescue and gene expression after heat shock. J Virol 73, 3560-3566.

Pascolo, S., Bervas, N., Ure, J. M., Smith, A. G., Lemonnier, F. A., and Perarnau, B. (1997). HLA-A2.1-restricted education and cytolytic activity of CD8(+) T lymphocytes from beta2 microglobulin (beta2m) HLA-A2.1 monochain transgenic H-2Db beta2m double knockout mice. J Exp Med 185, 2043-2051.

Radecke, F., and Billeter, M. A. (1997). Reverse Genetics Meets the Nonsegmented Negative-Strand RNA Viruses. Rev Med Virol 7, 49-63.

Radecke, F., Spielhofer, P., Schneider, H., Kaelin, K., Huber, M., Dotsch, C., Christiansen, G., and Billeter, M. A. (1995). Rescue of measles viruses from cloned DNA. EMBO J 14, 5773-5784.

Shay, J. W., and Bacchetti, S. (1997). A survey of telomerase activity in human cancer. European Journal of Cancer. 33, 787-791.

Singh, M., Cattaneo, R., and Billeter, M. A. (1999). A recombinant measles virus expressing hepatitis B virus surface antigen induces humoral immune responses in genetically modified mice. J Virol73, 4823-4828.

Vesely, M. D., Kershaw, M. H., Schreiber, R. D., and Smyth, M. J. (2011). Natural innate and adaptive immunity to cancer. Annu Rev Immunol 29, 235-271.

Wang, Q., Lei, C., Wan, H., and Liu, Q. (2012). Improved cellular immune response elicited by a ubiquitin-fused DNA vaccine against *Mycobacterium tuberculosis*. DNA and Cell Biology. 31, 489-495.

Yang, Y., Chen, Y., Zhang, C., Huang, H., and Weissman, S. M. (2002). Nucleolar localization of hTERT protein is associated with telomerase function. Exp Cell Res 277, 201-209.

Zhu, C. Q., Cutz, J. C., Liu, N., Lau, D., Shepherd, F. A., Squire, J. A., and Tsao, M. S. (2006). Amplification of telomerase (hTERT) gene is a poor prognostic marker in non-small-cell lung cancer. British Journal of Cancer. 94, 1452-1459.

The invention claimed is:

1. A method for preventing or treating a tumor in a patient, the method comprising administering to the patient an immunogenic composition comprising measles viral particles rescued from a recombinant measles virus plasmid in a helper-cell-based rescue system,
   wherein the recombinant measles virus plasmid comprises a recombinant cDNA molecule that encodes the full-length, infectious, antigenomic (+) RNA strand of a measles virus (MV),
   wherein the cDNA molecule further comprises an Additional Transcription Unit (ATU) that contains a heterologous DNA sequence capable of expressing a heterologous amino acid sequence,
   wherein said heterologous amino acid sequence is a human telomerase reverse transcriptase (hTERT) protein devoid of telomerase catalytic activity and of a nucleolar localization signal,
   wherein the hTERT protein is fused at N-terminus with a protein enhancing addressing of the hTERT protein to proteasome, and
   wherein the immunogenic composition is administered to the patient subsequent to an initial administration of a DNA molecule encoding hTERT protein.

2. The method of claim 1, wherein the hTERT protein is devoid of a nucleolar localization signal by deletion of at least amino acids 1-47 of SEQ ID NO: 2.

3. The method of claim 1, wherein the sequence that encodes the hTERT protein contains a mutation that inactivates the catalytic activity of the TERT protein.

4. The method of claim 1, wherein the hTERT protein is devoid of telomerase catalytic activity by deletion of at least one amino acid.

5. The method of claim 1, wherein the hTERT protein is devoid of telomerase catalytic activity by deletion of amino acids 867-869 (VDD) of SEQ ID NO: 2.

6. The method of claim 1, wherein the hTERT protein is devoid of a nucleolar localization signal by deletion of at least amino acids 1-23 of SEQ ID NO: 2.

7. The method of claim 1, wherein the protein enhancing addressing of the hTERT protein to the proteasome is ubiquitin or is a chaperone protein.

8. The method of claim 7, wherein the cDNA molecule encodes SEQ ID NO: 15.

9. The method of claim 1, wherein the ATU is located between the P and M genes of the measles virus.

10. The method of claim 1, wherein the MV originates from the Schwarz strain or the Moraten strain.

11. The method of claim 1, wherein the cDNA molecule is placed under the control of a heterologous expression control sequence appropriate for the transcription of the antigenomic (+)RNA strand starting from the cDNA molecule.

12. The method of claim 11, wherein the heterologous expression control sequence of said cDNA comprises the T7 promoter and T7 terminator sequences; and
   wherein the cDNA molecule optionally further comprises, at its 5'-end, adjacent to the first nucleotide of the nucleotide sequence encoding the full length, infectious antigenomic (+)RNA strand of the MV, a GGG motif followed by a hammerhead ribozyme sequence and which comprises, at its 3'-end, adjacent to the last nucleotide of said nucleotide sequence encoding the full length, infectious anti-genomic (+)RNA strand, the sequence of a hepatitis delta virus ribozyme.

13. The method of claim 1, wherein the cDNA molecule is comprised in a plasmid pTM-MVSchw deposited at the CNCM on Jun. 12, 2002 under n° I-2889.

14. A method for preventing or treating a tumor in a patient, the method comprising administering to the patient an immunogenic composition comprising a recombinant measles virus plasmid,
   wherein the recombinant measles virus plasmid comprises a recombinant cDNA molecule that encodes the full-length, infectious, antigenomic (+) RNA strand of a measles virus (MV),
   wherein the cDNA molecule further comprises an Additional Transcription Unit (ATU) that contains a heterologous DNA sequence capable of expressing a heterologous amino acid sequence,
   wherein said heterologous amino acid sequence is a human telomerase reverse transcriptase (hTERT) protein devoid of telomerase catalytic activity and of a nucleolar localization signal,
   wherein the hTERT protein is fused at N-terminus with a protein enhancing addressing of the hTERT protein to proteasome; and
   wherein the immunogenic composition is administered to the patient subsequent to an initial administration of a DNA molecule encoding hTERT protein.

15. The method of claim 14, wherein the hTERT protein is devoid of a nucleolar localization signal by deletion of at least amino acids 1-47 of SEQ ID NO: 2.

16. The method of claim 14, wherein the sequence that encodes the hTERT protein contains a mutation that inactivates the catalytic activity of the TERT protein.

17. The method of claim 14, wherein the hTERT protein is devoid of telomerase catalytic activity by deletion of at least one amino acid.

18. The method of claim 14, wherein the hTERT protein is devoid of telomerase catalytic activity by deletion of amino acids 867-869 (VDD) of SEQ ID NO: 2.

19. The method of claim 14, wherein the hTERT protein is devoid of a nucleolar localization signal by deletion of at least amino acids 1-23 of SEQ ID NO: 2.

20. The method of claim 14, wherein the protein enhancing addressing of the hTERT protein to the proteasome is ubiquitin or is a chaperone protein.

21. The method of claim 20, wherein the cDNA molecule encodes SEQ ID NO: 15.

22. The method of claim 14, wherein the ATU is located between the P and M genes of the measles virus.

23. The method of claim 14, wherein the MV originates from the Schwarz strain or the Moraten strain.

24. The method of claim 14, wherein the cDNA molecule is placed under the control of a heterologous expression control sequence appropriate for the transcription of the antigenomic (+)RNA strand starting from the cDNA molecule.

25. The method of claim 24, wherein the heterologous expression control sequence of said cDNA comprises the T7 promoter and T7 terminator sequences; and wherein the cDNA molecule optionally further comprises, at its 5'-end, adjacent to the first nucleotide of the nucleotide sequence encoding the full length, infectious antigenomic (+)RNA strand of the MV, a GGG motif followed by a hammerhead ribozyme sequence and which comprises, at its 3'-end, adjacent to the last nucleotide of said nucleotide sequence encoding the full length, infectious anti-genomic (+)RNA strand, the sequence of a hepatitis delta virus ribozyme.

26. The method of claim 14, wherein the cDNA molecule is comprised in a plasmid pTM-MVSchw deposited at the CNCM on Jun. 12, 2002 under n° I-2889.

* * * * *